United States Patent
Bell et al.

(10) Patent No.: US 7,968,540 B2
(45) Date of Patent: Jun. 28, 2011

(54) SPIROHYDANTOIN TRICYCLIC CGRP RECEPTOR ANTAGONISTS

(75) Inventors: Ian M. Bell, Harleysville, PA (US); Craig A. Stump, Pottstown, PA (US); Cory R. Theberge, King of Prussia, PA (US); Steven N. Gallicchio, Wyndmoor, PA (US); C. Blair Zartman, Hatfield, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 554 days.

(21) Appl. No.: 12/085,008

(22) PCT Filed: Nov. 14, 2006

(86) PCT No.: PCT/US2006/044190
§ 371 (c)(1),
(2), (4) Date: May 13, 2008

(87) PCT Pub. No.: WO2007/061694
PCT Pub. Date: May 31, 2007

(65) Prior Publication Data
US 2009/0281080 A1    Nov. 12, 2009

Related U.S. Application Data

(60) Provisional application No. 60/738,332, filed on Nov. 18, 2005.

(51) Int. Cl.
*A61K 31/55* (2006.01)
*C07D 243/04* (2006.01)
*C07D 487/10* (2006.01)

(52) U.S. Cl. ......................... 514/219; 540/555

(58) Field of Classification Search ................ None
See application file for complete search history.

(56) References Cited

U.S. PATENT DOCUMENTS

| | | | |
|---|---|---|---|
| 5,436,261 | A | 7/1995 | Cordi et al. |
| 6,548,710 | B2 | 4/2003 | Woudenberg |
| 7,189,722 | B2 | 3/2007 | Bell et al. |
| 7,192,954 | B2 | 3/2007 | Bell et al. |
| 7,202,251 | B2 | 4/2007 | Bell et al. |
| 7,384,930 | B2 | 6/2008 | Chaturvedula et al. |
| 7,384,931 | B2 | 6/2008 | Chaturvedula et al. |

FOREIGN PATENT DOCUMENTS

| | | |
|---|---|---|
| WO | WO 2004/082605    | 9/2004 |
| WO | WO 2004/082605 A2 | 9/2004 |
| WO | WO 2004/087649 A2 | 10/2004 |
| WO | WO 2006/029153 A2 | 3/2006 |
| WO | WO 2006/031491 A2 | 3/2006 |
| WO | WO 2006/031513 A2 | 3/2006 |
| WO | WO 2006/031606 A2 | 3/2006 |
| WO | WO 2006/031610 A2 | 3/2006 |
| WO | WO 2006/031676 A2 | 3/2006 |
| WO | WO 2006/052378 A1 | 5/2006 |
| WO | WO 2007/061676 A2 | 5/2007 |
| WO | WO 2007/061677 A2 | 5/2007 |
| WO | WO 2007/061692 A2 | 5/2007 |
| WO | WO 2007/061695 A2 | 5/2007 |
| WO | WO 2007/061696 A2 | 5/2007 |

OTHER PUBLICATIONS

Supplementary European Search Report and Search Opinion for counterpart European patent application No. EP 06 82 7801, Aug. 23, 2010.

*Primary Examiner* — Noble Jarrell
(74) *Attorney, Agent, or Firm* — Bernard Devlin; Raynard Yuro

(57) ABSTRACT

Compounds of formula I:

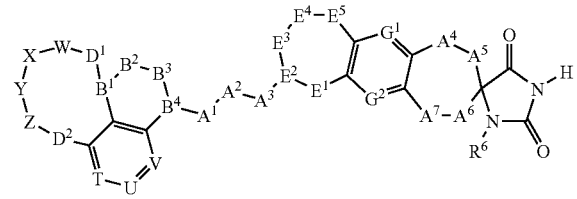

(wherein variables $A^1$, $A^2$, $A^3$, $A^4$, $A^5$, $A^6$, $A^7$, $B^1$, $B^2$, $B^3$, $B^4$, $D^1$, $D^2$, $E^1$, $E^2$, $E^3$, $E^4$, $E^5$, $G^1$, $G^2$, $R^6$, T, U, V, W, X, Y and Z are as described herein) which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

19 Claims, No Drawings

SPIROHYDANTOIN TRICYCLIC CGRP RECEPTOR ANTAGONISTS

CROSS-REFERENCE TO RELATED APPLICATIONS

This application claims priority under 35 U.S.C. §119(e) of U.S. provisional application Ser. No. 60/738,332, filed Nov. 18, 2005.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, asthma (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of the formula I:

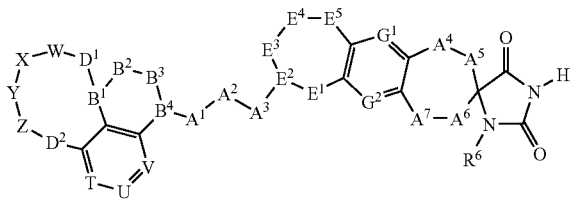

(wherein variables $A^1, A^2, A^3, A^4, A^5, A^6, A^7, B^1, B^2, B^3, B^4, D^1, D^2, E^1, E^2, E^3, E^4, E^5, G^1, G^2, R^1, T, U, V, W, X, Y$ and $Z$ are as described herein) which are antagonists of CGRP receptors and which are useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

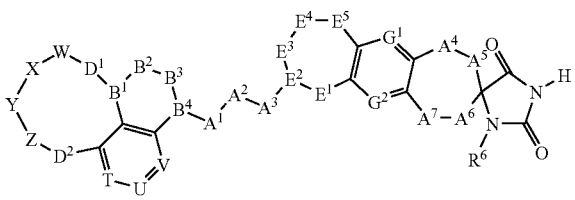

I wherein:
$A^1, A^2$ and $A^3$ are each independently selected from:
(1) a bond,
(2) —$CR^{13}R^{14}$—, wherein $R^{13}$ and $R^{14}$ are each independently selected from:
  (a) hydrogen,
  (b) $C_{1-6}$ alkyl, which is unsubstituted or substituted with 1-5 substituents each independently selected from:
    (i) —$C_{3-6}$cycloalkyl,
    (ii) —O—$C_{1-6}$alkyl,
    (iii) halo,
    (iv) hydroxy, and
    (v) phenyl,
  (c) hydroxy, and
  (d) halo,
(3) —$NR^{10}$—,
(4) —$CR^{13}R^{14}$—$NR^{10}$—,
(5) —$CR^{13}R^{14}$—$CH_2$—,
(6) —$CH_2$—$CR^{13}R^{14}$—,
(7) —O—$CR^{13}R^{14}$—,
(8) —$CR^{13}R^{14}$—O—,
(9) —C≡C—,
(10) —$C(R^{13})$=$C(R^{14})$—, and
(11) —C(=O)—,
where one or two of $A^1, A^2$ and $A^3$ are optionally absent;
0-1 of $A^4, A^5, A^6$ and $A^7$ is selected from:
(1) —O—,
(2) —C(=O)—
(3) —$N(R^{15})$—, wherein $R^{15}$ is selected from:
  (i) hydrogen,
  (ii) $C_{1-6}$ alkyl, which is unsubstituted or substituted with 1-5 substituents where the substituents are each independently selected from:
    (a) hydroxy,
    (b) —O—$C_{1-6}$alkyl,
    (c) halo,
    (d) —$C_{3-6}$cycloalkyl,
    (e) trifluoromethyl, and
    (f) phenyl,
where the remainder of $A^4, A^5, A^6$ and $A^7$ are each independently selected from:
(1) a bond, and
(2) —$CR^{13}R^{14}$—,
where one or both of $A^4$ and $A^7$ are optionally absent;
$B^1$ and $B^4$ are each independently selected from:
(1)

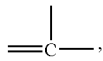

(2)

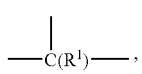

(3)

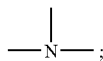

$B^2$ and $B^3$ are each independently selected from:
(1) a bond
(2) =$C(R^1)$—,
(3) —$CR^1R^2$—,
(4) —C(=O)—,
(5) —C(=S)—,
(6) —$C(=NR^1)$—,
(7) —N—,
(8) —$N(R^1)$—,
(9) —O—,
(10) —S—, and
(11) —$SO_2$—,
where one of $B^2$ and $B^3$ is optionally absent;
$D^1$ and $D^2$ are each independently selected from:
(1) =$C(R^1)$—,
(2) —$CR^1R^2$—,
(3) —C(=O)—,
(4) —C(=S)—,
(5) =N—,
(6) —$N(R^1)$—,
(7) —O—,
(8) —S—,
(9) —$SO_2$—, and
(10) —$C(=NR^1)$—;
$E^1$ and $E^5$ are each independently selected from:
(1) =$C(R^4)$—,
(2) —$CR^4R^5$—,
(3) —C(=O)—,
(4) —C(=S)—,
(5) =N—,
(6) =$N^+(O^-)$—,
(7) —$N(R^4)$—, (8) —O—,
(9) —S—, and
(10) —SO$_2$—;

E$^3$ and E$^4$ are each independently selected from:
(1) a bond,
(2) =C(R$^4$)—,
(3) —CR$^4$R$^5$—,
(4) —C(=O)—,
(5) =N—,
(6) =N$^+$(O$^-$)—,
(7) —N(R$^4$)—, and
(8) —O—,
where one or both of E$^3$ and E$^4$ are optionally absent;

E$^2$ is selected from:
(1)

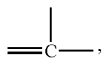

(2)

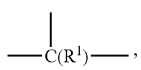

and
(3)

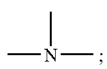

G$^1$ and G$^2$ are each independently selected from:
(1) =C(R$^4$)—,
(2) =N—, and
(3) =N$^+$(O$^-$)—;

T, U and V are each independently selected from:
(1) =C(R$^1$)—, and
(2) =N—, and
(3) =N$^+$(O$^-$)—;
wherein at least one of T, U, and V is =C(R$^1$)—;

W, X, Y, and Z are each independently selected from:
(1) a bond
(2) =C(R$^1$)—,
(3) —CR$^1$R$^2$—,
(4) —C(=O)—,
(5) —C(=S)—,
(6) =N—,
(7) —N(R$^1$)—,
(8) —O—,
(9) —S—,
(10) —S(O)—,
(11) —SO$_2$—, and
(12) —C(=NR$^1$)—
where 1-4 of W, X, Y and Z are optionally absent;

R$^1$ and R$^2$ are each independently selected from:
(1) hydrogen;
(2) —C$_{1-6}$alkyl, which is unsubstituted or substituted with 1-7 substituents each independently selected from:
(a) halo,
(b) hydroxy,
(c) —O—C$_{1-6}$alkyl, which is unsubstituted or substituted with 1-5 halo,
(d) —C$_{3-6}$cycloalkyl,
(e) phenyl or heterocycle, wherein heterocycle is selected from: azetidinyl, azepanyl, imidazolyl, oxazolyl, pyridinyl, pyrimidinyl, pyrazinyl, pyridazinyl, piperidinyl, azepinyl, piperazinyl, pyrazolyl, pyrrolidinyl, thiazolyl, thienyl, triazolyl, tetrazolyl, tetrahydrofuryl, or morpholinyl,
which phenyl or heterocycle is unsubstituted or substituted with 1-5 substituents each independently selected from:
(i) —C$_{1-6}$alkyl, which is unsubstituted or substituted with 1-5 halo,
(ii) —O—C$_{1-6}$alkyl, which is unsubstituted or substituted with 1-5 halo,
(iii) halo,
(iv) hydroxy,
(v) oxo,
(vi) amino
(vii) phenyl, and
(viii) benzyl
(f) —CO$_2$R$^9$, wherein R$^9$ is independently selected from:
(i) hydrogen,
(ii) —C$_{1-6}$alkyl, which is unsubstituted or substituted with 1-6 substituents, substituents each independently selected from:
(I) halo,
(II) hydroxy,
(III) —O—C$_{1-6}$alkyl, which is unsubstituted or substituted with 1-5 halo,
(IV) —C$_{3-6}$cycloalkyl,
(V) phenyl, which is unsubstituted or substituted with 1-5 substituents each independently selected from:
(1) —C$_{1-4}$alkyl,
(2) —O—C$_{1-6}$alkyl,
(3) halo,
(4) trifluoromethyl, and
(5) —OCF$_3$,
(iii) —C$_{3-6}$cycloalkyl, which is unsubstituted or substituted with 1-5 halo, and
(iv) phenyl or heterocycle, wherein heterocycle is selected from: pyridinyl, pyrimidinyl, pyrazinyl, pyridazinyl, thienyl, pyrrolidinyl, thiazolyl, oxazolyl, imidazolyl, triazolyl, tetrazolyl, benzimidazolyl, benzothiazolyl, benzoxazolyl, imidazolinyl, indolinyl, indolyl, quinolinyl, isoquinolinyl, tetrahydroquinolinyl, isoindolinyl, tetrahydroisoquinolinyl, tetrahydrofuryl, quinoxalinyl, piperidinyl, piperazinyl, and morpholinyl, which phenyl or heterocycle is unsubstituted or substituted with 1-5 substituents each independently selected from:
(I) halo,
(II) —C$_{1-6}$alkyl, which is unsubstituted or substituted with 1-5 halo
(III) —O—C$_{1-6}$alkyl, which is unsubstituted or substituted with 1-5 halo
(IV) —C$_{3-6}$cycloalkyl,
(V) oxo,
(VI) —CN,
(VII) hydroxy, and
(VIII) phenyl,
(g) —NR$^{10}$R$^{11}$, wherein R$^{10}$ and R$^{11}$ are each independently selected from:
(i) hydrogen,
(ii) —C$_{1-6}$alkyl, which is unsubstituted or substituted with 1-6 substituents each independently selected from:

(I) —O—$C_{1-6}$alkyl,
(II) halo,
(III) hydroxy,
(IV) —$OCF_3$,
(V) —$C_{3-6}$cycloalkyl, and
(VI) phenyl,
(iii) —$C_{4-6}$cycloalkyl,
(iv) phenyl, which is unsubstituted or substituted with 1-5 substituents where the substituents are independently selected from:
(I) —$C_{1-6}$alkyl,
(II) —O—$C_{1-6}$alkyl,
(III) halo,
(IV) hydroxy,
(V) trifluoromethyl,
(VI) —$OCF_3$, and
(VII) CN, and
(v) benzyl, which is unsubstituted or substituted with 1-5 substituents where the substituents are independently selected from:
(I) —$C_{1-6}$alkyl,
(II) —O—$C_{1-6}$alkyl,
(III) halo, and
(IV) trifluoromethyl,
(vi) —$COR^9$, and
(vii) —$SO_2R^{12}$,
(h) —$SO_2R^{12}$, wherein $R^{12}$ is selected from:
(i) —$C_{1-6}$alkyl, which is unsubstituted or substituted with 1-6 fluoro,
(ii) —$C_{3-6}$cycloalkyl,
(iii) phenyl or heterocycle, wherein heterocycle is selected from: pyridinyl, pyrimidinyl, pyrazinyl, pyridazinyl, piperidinyl, piperazinyl, pyrrolidinyl, thienyl, or morpholinyl, which phenyl or heterocycle is unsubstituted or substituted with 1-5 substituents independently selected from:
(I) —$C_{1-6}$alkyl,
(II) —O—$C_{1-6}$alkyl,
(III) halo,
(IV) hydroxy,
(V) trifluoromethyl,
(VI) —$OCF_3$, and
(VII) CN, and
(iv) benzyl, which is unsubstituted or substituted with 1-5 substituents independently selected from:
(I) —$C_{1-6}$alkyl,
(II) —O—$C_{1-6}$alkyl,
(III) halo, and
(IV) trifluoromethyl,
(i) —$CONR^{10a}R^{11a}$, wherein $R^{10a}$ and $R^{11a}$ are each independently selected from:
(i) hydrogen,
(ii) —$C_{1-6}$alkyl, which is unsubstituted or substituted with 1-6 substituents each independently selected from:
(I) —O—$C_{1-6}$alkyl, which is unsubstituted or substituted with 1-5 halo,
(II) halo,
(III) hydroxy,
(IV) —$OCF_3$,
(V) —$C_{3-6}$cycloalkyl, and
(VI) phenyl,
(iii) —$C_{5-6}$cycloalkyl,
(iv) phenyl, which is unsubstituted or substituted with 1-5 substituents where the substituents are independently selected from:
(I) —$C_{1-6}$alkyl, which is unsubstituted or substituted with 1-5 halo,
(II) —O—$C_{1-6}$alkyl, which is unsubstituted or substituted with 1-5 halo,
(III) halo,
(IV) hydroxy,
(V) trifluoromethyl,
(VI) —$OCF_3$, and
(VII) CN, and
(v) benzyl, which is unsubstituted or substituted with 1-5 substituents where the substituents are independently selected from:
(I) —$C_{1-6}$alkyl, which is unsubstituted or substituted with 1-5 halo,
(II) —O—$C_{1-6}$alkyl, which is unsubstituted or substituted with 1-5 halo,
(III) halo, and
(IV) trifluoromethyl,
or where $R^{10a}$ and $R^{11a}$ join to form a ring selected from azetidinyl, pyrrolidinyl, piperidinyl, azepanyl, piperazinyl, or morpholinyl, which ring is unsubstituted or substituted with 1-5 substituents each independently selected from:
(I) —$C_{1-6}$alkyl, which is unsubstituted or substituted with 1-5 halo,
(II) —O—$C_{1-6}$alkyl, which is unsubstituted or substituted with 1-5 halo,
(III) halo,
(IV) hydroxy,
(V) phenyl,
(VI) benzyl,
(VII) —$COR^9$, and
(VIII) —$SO_2R^{12}$
(j) trifluoromethyl,
(k) —$OCO_2R^9$,
(l) $(NR^{10a})CO_2R^9$,
(m) —$O(CO)NR^{10a}R^{11a}$,
(n) —$(NR^9)(CO)NR^{10a}R^{11a}$,
(O)—O—$C_{3-6}$cycloalkyl,
(p) —$SO_2NR^{10a}R^{11a}$, and
(q) —CN,
(3) —$C_{3-6}$cycloalkyl, which is unsubstituted or substituted with 1-7 substituents each independently selected from:
(a) halo,
(b) hydroxy,
(c) —O—$C_{1-6}$alkyl, which is unsubstituted or substituted with 1-5 halo,
(d) —$C_{1-6}$alkyl, which is unsubstituted or substituted with 1-5 halo,
(e) phenyl, which is unsubstituted or substituted with 1-5 substituents each independently selected from:
(i) —$C_{1-6}$alkyl,
(ii) —O—$C_{1-6}$alkyl,
(iii) halo,
(iv) hydroxy, and
(v) trifluoromethyl,
(4) phenyl or heterocycle, wherein heterocycle is selected from: pyridinyl, pyrimidinyl, pyrazinyl, thienyl, pyridazinyl, pyrrolidinyl, azetidinyl, azepanyl, thiazolyl, isothiazolyl, oxazolyl, isoxazolyl, imidazolyl, triazolyl, tetrazolyl, azepinyl, benzimidazolyl, benzopyranyl, benzofuryl, benzothiazolyl, benzoxazolyl, chromanyl, furyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, 1,3-diox-olanyl, oxadiazolyl, piperidinyl, tetrahydropyranyl, tetrahydrothienyl, tetrahydrothiopyranyl, and morpholinyl, which phenyl or heterocycle is unsubstituted or substituted with 1-5 substituents each independently selected from:
  (a) —$C_{1-6}$alkyl, which is unsubstituted or substituted with 1-5 substituents where the substituents are each independently selected from:
    (i) halo,
    (ii) hydroxy,
    (iii) —O—$C_{1-6}$alkyl, which is unsubstituted or substituted with 1-5 halo,
    (iv) —$C_{3-6}$cycloalkyl,
    (v) phenyl,
    (vi) —$CO_2R^9$, and
    (vii) —$NR^{10}R^{11}$,
  (b) halo,
  (c) hydroxy,
  (d) —O—$C_{1-6}$alkyl, which is unsubstituted or substituted with 1-6 fluoro,
  (e) —$C_{3-6}$cycloalkyl,
  (f) phenyl or heterocycle, wherein heterocycle is selected from: pyrrolidinyl, piperidinyl, piperazinyl, pyridinyl, pyrimidinyl, pyrazinyl, thienyl, or morpholinyl, which phenyl or heterocycle is unsubstituted or substituted with 1-substituents each independently selected from:
    (i) —$C_{1-6}$alkyl, which is unsubstituted or substituted with 1-5 halo,
    (ii) —O—$C_{1-6}$alkyl, which is unsubstituted or substituted with 1-5 halo,
    (iii) halo,
    (iv) hydroxy, and
    (v) trifluoromethyl,
  (g) —$CO_2R^9$,
  (h) —$(CO)R^9$,
  (i) —$NR^{10}R^{11}$,
  (j) —$CONR^{10a}R^{11a}$,
  (k) oxo
  (l) —$SR^{12}$,
  (m) —$S(O)R^{12}$,
  (n) —$SO_2R^{12}$,
  (o) —CN and
  (p) —$SO_2NR^{10a}R^{11a}$,
(5) halo,
(6) oxo,
(7) hydroxy,
(8) —O—$C_{1-6}$alkyl, which is unsubstituted or substituted with 1-5 substituents where the substituents are each independently selected from:
  (a) halo,
  (b) hydroxy,
  (c) —$C_{3-6}$cycloalkyl,
  (d) phenyl,
  (e) —$CO_2R^9$, and
  (f) —$NR^{10}R^{11}$,
(9) —CN,
(10) —$CO_2R^9$,
(11) —$NR^{10}R^{11}$,
(12) —$SR^{12}$,
(13) —$S(O)R^{12}$,
(14) —$SO_2R^{12}$,
(15) —$SO_2NR^{10a}R^{11a}$,
(16) —$CONR^{10a}R^{11a}$,
(17) —$OCO_2R^9$,
(18) $(NR^{10a})CO_2R^9$,
(19) —$O(CO)NR^{10a}R^{11a}$,
(20) —$(NR^9)(CO)NR^{10a}R^{11a}$,
(21) —(CO)—$(CO)NR^{10a}R^{11a}$, and
(22) —(CO)—$(CO)OR^9$;
$R^4$ and $R^5$ are each independently selected from:
  (1) hydrogen;
  (2) —$C_{1-4}$alkyl, which is unsubstituted or substituted with 1-5 substituents each independently selected from:
    (a) halo,
    (b) hydroxy,
    (c) —O—$C_{1-6}$alkyl, which is unsubstituted or substituted with 1-5 halo,
    (d) —$C_{3-6}$cycloalkyl,
    (e) phenyl,
    (f) —$CO_2R^9$,
    (g) —$NR^{10}R^{11}$, and
    (h) —$CONR^{10a}R^{11a}$
  (3) —$C_{3-6}$cycloalkyl,
  (4) phenyl, which is unsubstituted or substituted with 1-3 substituents where the substituents are each independently selected from:
    (a) —$C_{1-4}$alkyl, which is unsubstituted or substituted with 1-3 halo,
    (b) halo,
    (c) hydroxy, and
    (d) —O—$C_{1-4}$alkyl, which is unsubstituted or substituted with 1-6 halo,
  (5) halo,
  (6) hydroxy,
  (7) —O—$C_{1-6}$alkyl, which is unsubstituted or substituted with 1-5 halo,
  (8) —CN,
  (9) —$CO_2R^9$,
  (10) —$NR^{10}R^{11}$,
  (11) —$SO_2R^{12}$,
  (12) —$CONR^{10a}R^{11a}$,
  (13) —$OCO_2R^9$, and
  (14) —$(NR^{10a})CO_2R^9$;
$R^6$ is selected from:
  (1) hydrogen,
  (2) —$C_{1-6}$alkyl or —$C_{3-6}$cycloalkyl which are unsubstituted or substituted with 1-7 substituents each independently selected from:
    (a) halo,
    (b) hydroxy,
    (c) —O—$C_{1-6}$alkyl,
    (d) —$C_{3-6}$cycloalkyl,
    (e) phenyl, which is unsubstituted or substituted with 1-5 substituents each independently selected from:
      (i) —$C_{1-6}$alkyl,
      (ii) —O—$C_{1-6}$alkyl,
      (iii) halo,
      (iv) hydroxy, and
      (v) trifluoromethyl,
    (f) —$CO_2R^9$,
    (g) —$NR^{10}R^{11}$,
    (h) —$CONR^{10}R^{11}$,
    (i) —$SO_2R^{12}$, and
    (j) trifluoromethyl
  (3) phenyl or heterocycle, wherein heterocycle is selected from: pyridinyl, pyrimidinyl, pyrazinyl, thienyl, or morpholinyl, which phenyl or heterocycle is unsubstituted or substituted with 1-5 substituents each independently selected from:
    (a) —$C_{1-6}$alkyl,
    (b) —O—$C_{1-6}$alkyl,
    (c) halo, (d) hydroxy, and (e) trifluoromethyl;

and pharmaceutically acceptable salts thereof and individual enantiomers and diastereomers thereof.

In embodiments of the invention where $R^6$ is methyl, $A^1$ is $CR^{13}R^{14}$—, $A^2$, $A^3$, $A^4$ and $A^7$ are absent, $A^5$ and $A^6$ are $CH_2$—, $G^1$ and $G^2$ are $=C(R^4)$—, $E^1$ is $=N$—, $E^2$ is

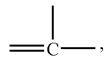

$E^3$ and $E^3$ are $=C(H)$—, and $B^4$ is absent, the following structure forms:

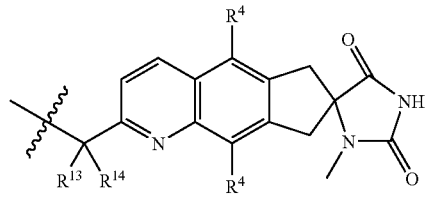

In embodiments of the invention where $R^6$ is methyl, $A^1$ is —C(=O)—, $A^2$, $A^3$, $A^4$ and $A^7$ are absent, $A^5$ and $A^6$ are —$CH_2$—, $G^1$ and $G^2$ are $=C(R^4)$—, $E^1$ is $=N$—, $E^2$ is

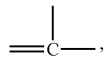

$E^3$ and $E^5$ are $=C(H)$—, and $E^4$ is absent, the following structure forms:

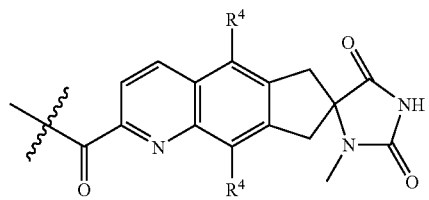

In embodiments of the invention where $R^6$ is methyl, $A^1$ is $CR^{13}R^{14}$, $A^2$, $A^3$, $A^4$ and $A^7$ are absent, $A^5$ and $A^6$ are $CH_2$—, $G^1$ and $G^2$ are $=C(R^4)$—, $E^1$ and $E^5$ are $=N$—, $E^2$ is

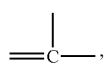

$E^3$ is $=C(H)$—, and $E^4$ is absent, the following structure forms:

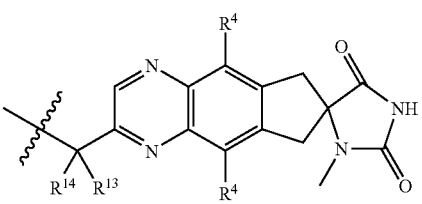

In embodiments of the invention where $R^6$ is methyl, $A^1$ is $CR^{13}R^{14}$, $A^2$, $A^3$, $A^4$ and $A^7$ are absent, $A^5$ and $A^6$ are —$CH_2$—, $G^1$ and $G^2$ are $=C(R^4)$—, $E^1$ is —$N(R^4)$—, $E^2$ is

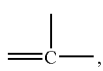

$E^3$ and $E^4$ are absent, and $E^5$ is $=N$—, the following structure forms:

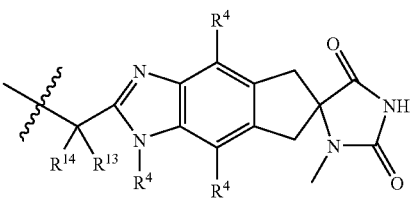

In embodiments of the invention where $R^6$ is methyl, $A^1$ is $CR^{13}R^{14}$—, $A^2$, $A^3$, $A^4$ and $A^7$ are absent, $A^5$ and $A^6$ are $CH_2$—, $G^1$ and $G^2$ are $=C(R^4)$—, $E^1$ is —N(H)—, $E^2$ is

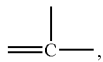

$E^3$ is $=N$—, $E^4$ and $E^5$ are —$CR^4R^5$—, the following structure forms:

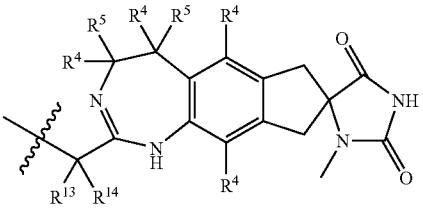

In embodiments of the invention where $B^4$ is

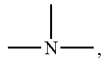

$B^2$ is —C(=O)—, $B^3$ is absent, $B^1$ is

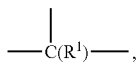

$D^1$ is —$CR^1R^2$—, $D^2$ is —$N(R^1)$—, W is —$C(=O)$—, X, Y and Z are absent, and T, U and V are =$C(R^1)$—, the following structure forms:

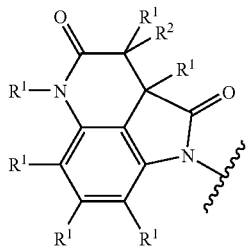

In embodiments of the invention where $B^4$ is

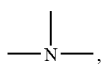

$B^2$ is —$C(=O)$—, $B^3$ is absent, $B^1$ is

$D^1$ is —$CR^1R^2$—, $D^2$ is —$N(R^1)$—, W is $C(=O)$—, X, Y and Z are absent, and T, U and V are =$C(R^1)$—, the following structure forms:

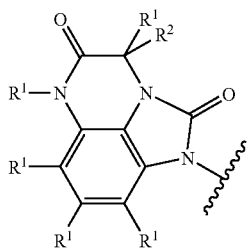

In embodiments of the invention where $B^4$ is

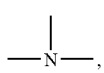

$B^2$ is —$CR^1R^2$—, $B^3$ is absent, $B^1$ is

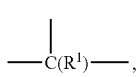

$D^1$ is —$CR^1R^2$—, $D^2$ is —$N(R^1)$—, W is —$C(=O)$—, X, Y and Z are absent, and T, U and V are =$C(R^1)$, the following structure forms:

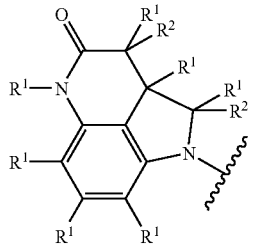

In embodiments of the invention where $B^4$ is

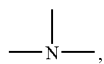

$B^2$ is =$C(R^1)$—, $B^3$ is absent, $B^1$ is

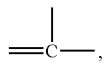

$D^1$ is —$CR^1R^2$—, $D^2$ is —$N(R^1)$—, W is $C(=O)$—, X, Y and Z are absent, and T, U and V are =$C(R^1)$—, the following structure forms:

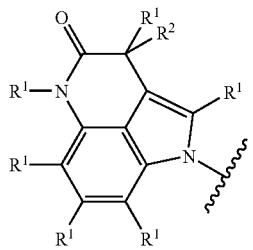

In embodiments of the invention where $B^4$ is

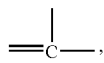

$B^2$ is =$C(R^1)$—, $B^3$ is absent, $B^1$ is

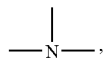

$D^1$ is —$R^1R^2$—, $D^2$ is —$N(R^1)$—, W is $C(=O)$—, X, Y and Z are absent, and T, U and V are =$C(R^1)$—, the following structure forms:

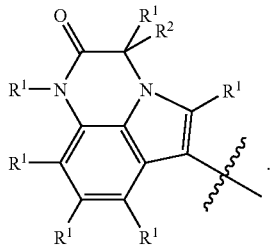

In embodiments of the invention where $B^4$ is

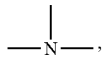

$B^2$ is $=C(R^1)-$, $B^3$ is absent, $B^1$ is

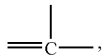

$D^2$ is $-CR^1R^2-$, $D^1$ is $-N(R^1)-$, W is $-C(=O)-$, X, Y and Z are absent, and T, U and V are $=C(R^1)-$, the following structure forms:

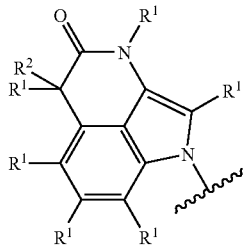

In embodiments of the invention where $B^4$ is

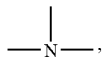

$B^2$ is $-C(=O)-$, $B^3$ is absent, $B^1$ is

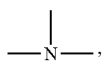

$D^1$ is $-R^1R^2-$, $D^2$ is $-N(R^1)-$, W is $-C(=O)-$, X, Y and Z are absent, and T and V are $=C(R^1)-$, and U is $=N-$, the following structure forms:

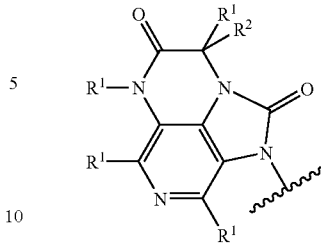

In embodiments of the invention where $B^4$ is

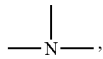

$B^2$ is $-C(O)-$, $B^3$ is absent, $B^1$ is

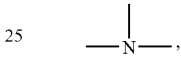

$D^1$ is $-CR^1R^2-$, $D^2$ is $-N(R^1)-$, W is $-C(=O)-$, X, Y and Z are absent, and U and V are $=C(R^1)-$, and T is $=N-$, the following structure forms:

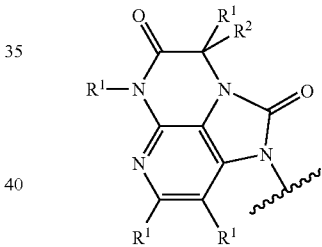

In embodiments of the invention where $B^4$ is

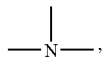

$B^2$ is $C(=O)-$, $B^3$ is absent, $B^1$ is

$D^1$ is $=C(R^1)-$, $D^2$ is $-N(R^1)-$, W is $C(=O)-$, X, Y and Z are absent, and T, U and V are $=C(R^1)-$, the following structure forms:

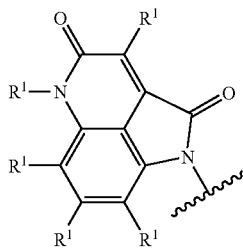

In embodiments of the invention where $B^4$ is

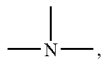

$B^3$ is C(=O)—, $B^2$ is =C($R^1$)—, $B^1$ is

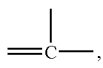

$D^1$ is —C(=O)—, $D^2$ is —N($R^1$)—, W, X, Y and Z are absent, and T, U and V are =C($R^1$)—, the following structure forms:

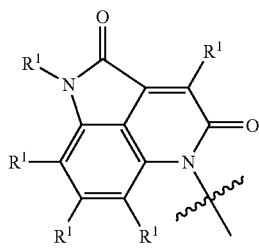

In embodiments of the invention where $B^4$ is

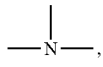

$B^2$ is —C(=O)—, $B^3$ is absent, $B^1$ is

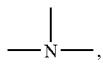

$D^1$ is —$R^1R^2$—, $D^2$ is —N($R^1$)—, W is absent, X and Y are —$R^1R^2$—, Z is —C(=O)—, and T, U and V are =C($R^1$)—, the following structure forms:

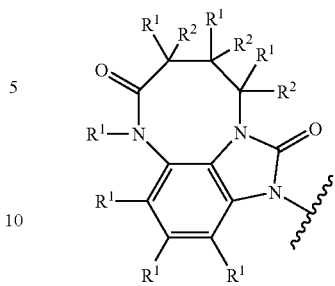

In embodiments of the invention where $B^4$ is

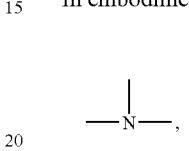

$B^2$ is —$R^1R^2$—, $B^3$ is absent, $B^1$ is

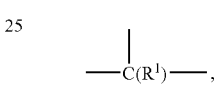

$D^1$ is —$CR^1R^2$—, $D^2$ is —N($R^1$)—, W is absent, X and Y are —$R^1R^2$—, Z is C(=O)—, and T, U and V are =C($R^1$)—, the following structure forms:

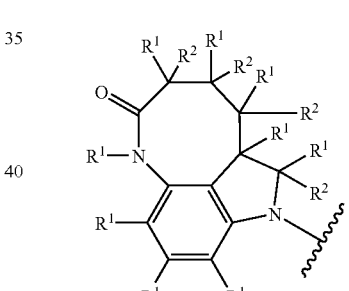

In embodiments of the invention where $B^4$ is

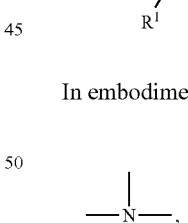

$B^2$ is —$CR^1R^2$—, $B^3$ is absent, $B^1$ is

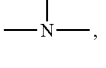

$D^1$ is —$R^1R^2$—, $D^2$ is —N($R^1$)—, W and X are absent, Y is —$CR^1R^2$—, Z is —C(=O)—, and T, U and V are =C($R^1$)—, the following structure forms:

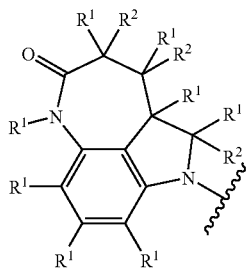

In embodiments of the invention where $B^4$ is

$B^2$ is $=C(R^1)—$, $B^3$ is absent, $B^1$ is

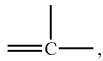

$D^1$ is $CR^1R^2—$, $D^2$ is $—N(R^1)—$, W and X are absent, Y is $—CR^1R^2—$, Z is $C(=O)—$, and T, U and V are $=C(R^1)—$, the following structure forms:

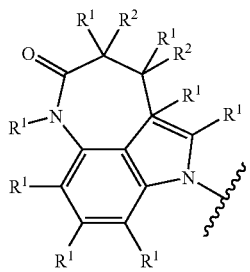

An embodiment of the present invention includes compounds of the formula Ia:

Ia

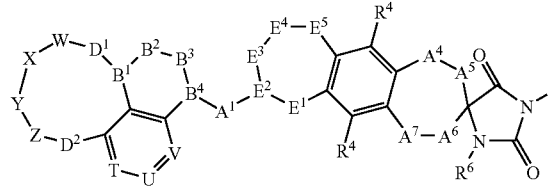

wherein $A^1$, $A^4$, $A^5$, $A^6$, $A^7$, $B^1$, $B^2$, $B^3$, $B^4$, $D^1$, $D^2$, $E^1$, $E^2$, $E^3$, $E^4$, $E^5$, T, U, V, W, X, Y, Z, $R^4$ and $R^6$ are defined herein; and pharmaceutically acceptable salts thereof and individual enantiomers and diastereomers thereof.

Another embodiment of the present invention includes compounds of the formula Ib:

Ib

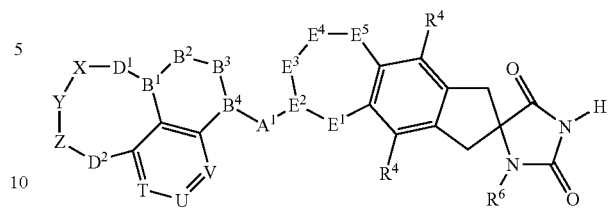

wherein $A^1$, $B^1$, $B^2$, $B^3$, $B^4$, $D^1$, $D^2$, $E^1$, $E^2$, $E^3$, $E^4$, $E^5$, T, U, V, X, Y, Z, $R^4$ and $R^6$ are defined herein; and pharmaceutically acceptable salts thereof and individual enantiomers and diastereomers thereof.

Another embodiment of the present invention includes compounds of the formula Ic:

Ic

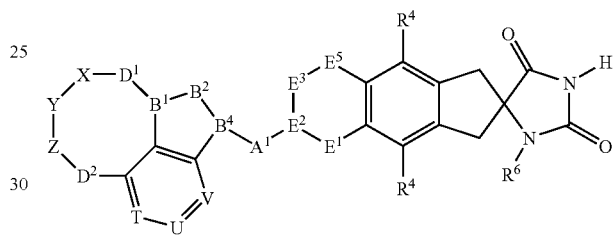

wherein $A^1$, $B^1$, $B^2$, $B^4$, $D^1$, $D^2$, $E^1$, $E^2$, $E^3$, $E^5$, T, U, V, X, Y, Z, $R^4$ and $R^6$ are defined herein; and pharmaceutically acceptable salts thereof and individual enantiomers and diastereomers thereof.

Another embodiment of the present invention includes compounds of the formula Id:

Id

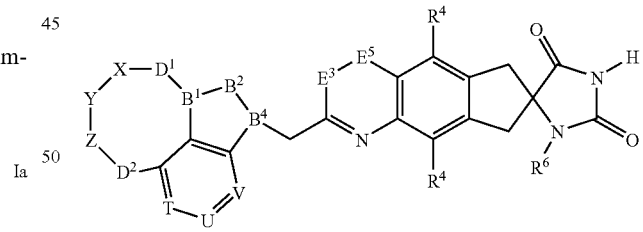

wherein $B^1$, $B^2$, $B^4$, $D^1$, $D^2$, $E^3$, $E^5$, T, U, V, X, Y, Z, $R^4$ and $R^6$ are defined herein;

and pharmaceutically acceptable salts thereof and individual enantiomers and diastereomers thereof.

Another embodiment of the present invention includes compounds of the formula Ie:

Ie

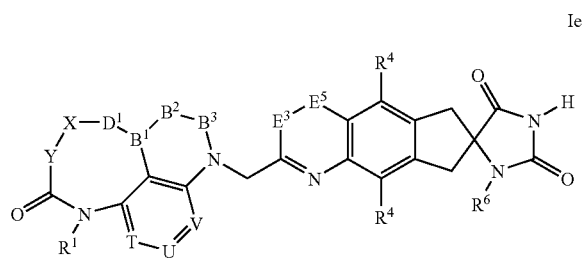

wherein $B^1$, $B^2$, $B^3$, $D^1$, $E^3$, $E^5$, T, U, V, X, Y, $R^1$, $R^4$, and $R^6$ are defined herein; and pharmaceutically acceptable salts thereof and individual enantiomers and diastereomers thereof.

In an embodiment of the present invention $A^1$ is $CH_2$.
In an embodiment of the present invention $A^1$ is $C(=O)$—.
In an embodiment of the present invention $A^2$ is a bond.
In an embodiment of the present invention $A^3$ is a bond.
In an embodiment of the present invention $A^4$ is selected from: $CH_2$; and a bond.
In an embodiment of the present invention $A^4$ is a bond.
In an embodiment of the present invention $A^5$ is $CH_2$.
In an embodiment of the present invention $A^6$ is $CH_2$.
In an embodiment of the present invention $A^7$ is selected from: $CH_2$; and a bond.
In an embodiment of the present invention $A^7$ is a bond.
In an embodiment of the present invention $B^1$ is selected from:

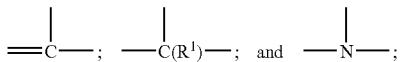

wherein $R^1$ is defined herein.
In an embodiment of the present invention $B^4$ is selected from:

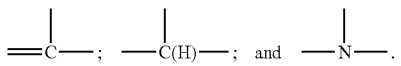

In an embodiment of the present invention $B^4$ is

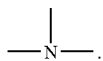

In an embodiment of the present invention $B^2$ is selected from:
=C($R^1$)—; —C$R^1$,$R^2$—; and —C(=O)—; wherein $R^1$ and $R^2$ are defined herein.
In an embodiment of the present invention $B^2$ is selected from:
=C(H)—; —$CH_2$—; and —C(=O)—.
In an embodiment of the present invention $B^3$ is selected from:
=C(H)—; —$CH_2$—; —C(=O)—; and a bond.
In an embodiment of the present invention $B^3$ is a bond.
In an embodiment of the present invention $D^1$ is selected from:
=C($R^1$)—; —C$R^1R^2$—; —C(=O)—; and —N($R^1$)—; wherein $R^1$ and $R^2$ are defined herein.

In an embodiment of the present invention $D^1$ is selected from:
=C(H)—; —$CH_2$—; —C(=O)—; and —N(H)—.
In an embodiment of the present invention $D^1$ is —$CH_2$—.
In an embodiment of the present invention $D^2$ is selected from:
—C$R^1R^2$—; and —N($R^1$)—; wherein $R^1$ and $R^2$ are defined herein.
In an embodiment of the present invention $D^2$ is selected from:
—$CH_2$—; —N(H)—; and —N(Me)—.
In an embodiment of the present invention $D^2$ is —N(H)—.
In an embodiment of the present invention $E^1$ is selected from:
=C($R^4$)—; —C$R^4R^5$—; =N—; and —N($R^4$)—; wherein $R^4$ and $R^5$ are defined herein.
In an embodiment of the present invention $E^1$ is selected from: =N—; and —N(H)—.
In an embodiment of the present invention $E^5$ is selected from:
=C($R^4$)—; —C$R^4R^5$—; =N—; and —N($R^4$)—; wherein $R^4$ and $R^5$ are defined herein.
In an embodiment of the present invention $E^5$ is selected from:
=C(H)—; —$CH_2$—; =N—; and —N(H)—.
In an embodiment of the present invention $E^3$ is selected from:
a bond; =C($R^4$)—; —C$R^4R^5$—; =N—; and —N($R^4$)—; wherein $R^4$ and $R^5$ are defined herein.
In an embodiment of the present invention $E^3$ is selected from:
a bond; =C(H)—; =N—; and —N(H)—.
In an embodiment of the present invention $E^4$ is selected from:
a bond; and —$CH_2$—.
In an embodiment of the present invention $E^4$ is a bond.
In an embodiment of the present invention $E^2$ is selected from:

In an embodiment of the present invention $E^2$ is

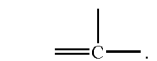

In an embodiment of the present invention $G^1$ is =C($R^4$)—; wherein $R^4$ is defined herein.
In an embodiment of the present invention $G^1$ is =C(H)—.
In an embodiment of the present invention $G^2$ is =C($R^4$)—; wherein $R^4$ is defined herein.
In an embodiment of the present invention $G^2$ is =C(H)—.
In an embodiment of the present invention T is selected from:
=C($R^1$)—; and =N—; wherein $R^1$ is defined herein.
In an embodiment of the present invention T is selected from:
=C(H)—; and =N—.
In an embodiment of the present invention U is selected from:
=C($R^1$)—; and =N—; wherein $R^1$ is defined herein.

In an embodiment of the present invention U is selected from:
=C(H)—; =C(Me)—; and —N—.

In an embodiment of the present invention V is =C(H)—.

In an embodiment of the present invention W is selected from:
a bond; —CR$^1$R$^2$—; and —C(=O)—; wherein R$^1$ and R$^2$ are defined herein.

In an embodiment of the present invention W is selected from:
a bond; —CH$_2$—; and —C(=O)—.

In an embodiment of the present invention W is —C(=O)—.

In an embodiment of the present invention W is a bond.

In an embodiment of the present invention X is selected from:
a bond; —CR$^1$R$^2$—; and —C(=O)—; wherein R$^1$ and R$^2$ are defined herein.

In an embodiment of the present invention X is selected from:
a bond; —CH$_2$—; and —C(=O)—.

In an embodiment of the present invention X is a bond.

In an embodiment of the present invention Y is selected from:
a bond; —CR$^1$R$^2$—; and —C(=O)—; wherein R$^1$ and R$^2$ are defined herein.

In an embodiment of the present invention Y is selected from:
a bond; —CH$_2$—; and —C(=O)—.

In an embodiment of the present invention Y is a bond.

In an embodiment of the present invention Z is selected from:
a bond; —CR$^1$R$^2$—; and —C(=O)—; wherein R$^1$ and R$^2$ are defined herein.

In an embodiment of the present invention Z is —C(=O)—.

In an embodiment of the present invention Z is a bond.

In an embodiment of the present invention R$^1$ and R$^2$ are independently selected from:
(1) hydrogen;
(2) —C$_{1-6}$alkyl, which is unsubstituted or substituted with 1-5 substituents each independently selected from:
   (a) halo,
   (b) hydroxy,
   (c) —O—C$_{1-6}$alkyl, which is unsubstituted or substituted with 1-3 fluoro,
   (d) —C$_{3-6}$cycloalkyl,
   (e) phenyl or heterocycle, wherein heterocycle is selected from: azetidinyl, imidazolyl, oxazolyl, pyridinyl, pyrimidinyl, pyrazinyl, piperidinyl, piperazinyl, pyrrolidinyl, thiazolyl, thienyl, triazolyl, tetrazolyl, tetrahydrofuryl, or morpholinyl, which phenyl or heterocycle is unsubstituted or substituted with 1-3 substituents each independently selected from:
      (i) —C$_{1-4}$alkyl, which is unsubstituted or substituted with 1-3 fluoro,
      (ii) —O—C$_{1-4}$alkyl, which is unsubstituted or substituted with 1-3 fluoro,
      (iii) halo,
      (iv) hydroxy,
      (v) trifluoromethyl, and
      (vi) —OCF$_3$,
   (f) —CO$_2$R$^9$,
   (g) —NR$^{10}$R$^{11}$,
   (h) —CONR$^{10a}$R$^{11a}$,
   (i) —(NR$^{10a}$)CO$_2$R$^9$, and
   (j) —(NR$^9$)(CO)NR$^{10a}$R$^{11a}$;
(3) —C$_{3-6}$cycloalkyl, which is unsubstituted or substituted with 1-3 substituents each independently selected from:
   (a) halo,
   (b) hydroxy,
   (c) —C$_{1-6}$alkyl, and
   (d) —O—C$_{1-6}$alkyl,
(4) phenyl or heterocycle, wherein heterocycle is selected from: pyridinyl, pyrimidinyl, pyrazinyl, thienyl, pyrrolidinyl, azetidinyl, thiazolyl, oxazolyl, isoxazolyl, imidazolyl, triazolyl, tetrazolyl, benzimidazolyl, benzoxazolyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, quinazolinyl, tetrahydrofuryl, naphthyridinyl, quinoxalinyl, 1,3-dioxolanyl, oxadiazolyl, piperidinyl, tetrahydropyranyl, and morpholinyl, which phenyl or heterocycle is unsubstituted or substituted with 1-3 substituents each independently selected from:
   (a) —C$_{1-4}$alkyl, which is unsubstituted or substituted with 1-3 fluoro,
   (b) halo,
   (c) hydroxy,
   (d) —O—C$_{1-4}$alkyl, which is unsubstituted or substituted with 1-6 fluoro,
   (e) —C$_{3-6}$cycloalkyl,
   (g) —CO$_2$R$^9$,
   (h) —NR$^{10}$R$^{11}$, and
   (i) —CONR$^{10a}$R$^{11a}$,
(5) halo,
(6) hydroxy,
(7) —O—C$_{1-4}$alkyl, which is unsubstituted or substituted with 1-3 halo,
(8) —CN,
(9) —CO$_2$R$^9$,
(10) —NR$^{10}$R$^{11}$,
(11) —CONR$^{10a}$R$^{11a}$ and
(12) —(NR$^{10a}$)CO$_2$R$^9$.

In an embodiment of the present invention R$^1$ and R$^2$ are independently selected from:
(1) hydrogen;
(2) —C$_{1-4}$alkyl, which is unsubstituted or substituted with 1-3 substituents each independently selected from:
   (a) halo,
   (b) —O—C$_{1-4}$alkyl,
   (c) phenyl or heterocycle, wherein heterocycle is selected from: azetidinyl, oxazolyl, pyridinyl, pyrimidinyl, pyrazinyl, piperidinyl, piperazinyl, pyrrolidinyl, tetrahydrofuryl, or morpholinyl, which phenyl or heterocycle is unsubstituted or substituted with 1-3 substituents each independently selected from:
      (i) —C$_4$alkyl,
      (ii) —O—C$_{1-4}$alkyl,
      (iii) halo, and
      (iv) hydroxy,
   (d) —CO$_2$R$^9$,
   (e) —NR$^{10}$R$^{11}$,
   (f) —CONR$^{10a}$R$^{11a}$,
(3) —C$_{3-6}$cycloalkyl,
(4) phenyl or heterocycle, wherein heterocycle is selected from: pyridinyl, pyrimidinyl, pyrazinyl, pyrrolidinyl, azetidinyl, oxazolyl, imidazolyl, 2-oxopiperazinyl, 2-oxopiperidinyl, 2-oxopyrrolidinyl, tetrahydrofuryl, oxadiazolyl, piperidinyl, and morpholinyl, which phenyl or heterocycle is unsubstituted or substituted with 1-3 substituents each independently selected from:

(a) —$C_{1-4}$alkyl, which is unsubstituted or substituted with 1-3 fluoro,
(b) halo,
(c) hydroxy,
(d) —O—$C_{1-4}$alkyl,
(e) —$C_{3-6}$cycloalkyl,
(f) —$NR^{10}R^{11}$, and
(g) —$CONR^{10}R^{11}$,
(5) halo,
(6) hydroxy,
(7) —O—$C_{1-4}$alkyl, which is unsubstituted or substituted with 1-3 halo,
(8) —CN,
(9) —$CO_2R^9$,
(10) —$NR^{10}R^{11}$,
(11) —$CONR^{10a}R^{11a}$, and
(12) —$(NR^{10a})CO_2R^9$.

In an embodiment of the present invention $R^4$ and $R^5$ are independently selected from:
(1) hydrogen;
(2) —$C_{1-4}$alkyl, which is unsubstituted or substituted with 1-3 substituents each independently selected from:
 (a) halo,
 (b) hydroxy,
 (c) —O—$C_{1-6}$alkyl,
 (d) —$C_{3-6}$cycloalkyl, and
 (e) phenyl,
(3) —$C_{3-6}$cycloalkyl,
(4) phenyl, which is unsubstituted or substituted with 1-3 substituents each independently selected from:
 (a) —$C_{1-4}$alkyl, which is unsubstituted or substituted with 1-3 fluoro, and
 (b) halo,
(5) halo,
(6) hydroxy,
(7) —O—$C_{1-6}$alkyl, which is unsubstituted or substituted with 1-3 fluoro,
(8) —CN, and
(9) —$NR^{10}R^{11}$;

In an embodiment of the present invention $R^4$ and $R^5$ are independently selected from:
(1) hydrogen;
(2) —$C_{1-4}$alkyl, which is unsubstituted or substituted with 1-3 fluoro,
(3) phenyl,
(5) halo, and
(6) hydroxy;

In an embodiment of the present invention $R^4$ and $R^5$ are independently selected from: hydrogen, halo, and methyl.

In an embodiment of the present invention $R^4$ is hydrogen.

In an embodiment of the present invention $R^5$ is hydrogen.

In an embodiment of the present invention $R^6$ is selected from:
(1) hydrogen,
(2) —$C_{1-4}$alkyl which is unsubstituted or substituted with 1-5 substituents each independently selected from:
 (a) halo,
 (b) hydroxy,
 (c) —$C_{3-6}$cycloalkyl, and
 (d) phenyl,
(3) phenyl or heterocycle, wherein heterocycle is selected from: pyridinyl, pyrimidinyl, or pyrazinyl, In an embodiment of the present invention $R^6$ is selected from:
(1) hydrogen,
(2) —$C_{1-4}$alkyl which is unsubstituted or substituted with 1-3 substituents each independently selected from:
 (a) halo, and
 (b) phenyl.

In an embodiment of the present invention $R^6$ is hydrogen or methyl.

In an embodiment of the present invention $R^6$ is methyl.

In an embodiment of the present invention $R^9$ is selected from:
(i) hydrogen,
(ii) —$C_{1-6}$alkyl, which is unsubstituted or substituted with 1-3 substituents, substituents each independently selected from:
 (I) halo,
 (II) hydroxy,
 (III) —O—$C_{1-4}$alkyl,
 (IV) —$C_{3-6}$cycloalkyl,
 (V) phenyl, which is unsubstituted or substituted with 1-3 substituents each independently selected from:
  (1) —$C_{1-4}$alkyl,
  (2) —O—$C_{1-4}$alkyl, and
  (3) halo,
(iii) —$C_{3-6}$cycloalkyl, and
(iv) phenyl or heterocycle, wherein heterocycle is selected from: pyridinyl, pyrimidinyl, pyrazinyl, thienyl, pyrrolidinyl, thiazolyl, oxazolyl, imidazolyl, triazolyl, tetrazolyl, imidazolinyl, indolinyl, indolyl, quinolinyl, isoquinolinyl, piperidinyl, piperazinyl, and morpholinyl, which phenyl or heterocycle is unsubstituted or substituted with 1-3 substituents each independently selected from:
 (I) halo,
 (II) —$C_{1-4}$alkyl,
 (III) —O—$C_{1-4}$alkyl, and
 (IV) oxo.

In an embodiment of the present invention $R^9$ is selected from:
(i) hydrogen,
(ii) —$C_{1-4}$alkyl, which is unsubstituted or substituted with 1-3 substituents, substituents each independently selected from:
 (I) halo, and
 (II) hydroxy,
(iii) —$C_{3-6}$cycloalkyl, and
(iv) phenyl.

In an embodiment of the present invention $R^{10}$ and $R^{11}$ are each independently selected from:
(i) hydrogen,
(ii) —$C_{1-6}$alkyl, which is unsubstituted or substituted with 1-3 substituents each independently selected from:
 (I) —O—$C_{1-4}$alkyl,
 (II) halo,
 (III) hydroxy,
 (IV) —$C_{3-6}$cycloalkyl, and
 (V) phenyl,
(iii) —$C_{4-6}$cycloalkyl,
(iv) phenyl, which is unsubstituted or substituted with 1-3 substituents where the substituents are independently selected from:
 (I) —$C_{1-4}$alkyl,
 (II) —O—$C_{1-4}$alkyl, and
 (III) halo,
(v) benzyl, which is unsubstituted or substituted with 1-3 substituents where the substituents are independently selected from:
 (I) —$C_{1-4}$alkyl,
 (II) —O—$C_{1-4}$alkyl, and
 (III) halo,
(vi) —$COR^9$, and (vii) —$SO_2R^{12}$.

In an embodiment of the present invention $R^{10}$ and $R^{11}$ are each independently selected from:
(i) hydrogen,
(ii) —$C_{1-4}$alkyl, which is unsubstituted or substituted with 1-3 substituents each independently selected from:
  (I) —O—$C_{1-4}$alkyl, and
  (II) halo,
(iii) —$C_{4-6}$cycloalkyl,
(iv) phenyl,
(v) benzyl,
(vi) —$COR^9$, and
(vii) —$SO_2R^{12}$.

In an embodiment of the present invention $R^{10a}$ and $R^{11a}$ are each independently selected from:
(i) hydrogen,
(ii) —$C_{1-4}$alkyl, which is unsubstituted or substituted with 1-3 substituents each independently selected from:
  (I) —O—$C_{1-4}$alkyl,
  (II) halo,
  (III) hydroxy,
  (IV) —$C_{3-6}$cycloalkyl, and
  (V) phenyl,
(iii) —$C_{5-6}$cycloalkyl,
(iv) phenyl, which is unsubstituted or substituted with 1-3 substituents where the substituents are independently selected from:
  (I) —$C_{1-4}$alkyl,
  (II) —O—$C_{1-4}$alkyl,
  (III) halo,
  (IV) hydroxy, and
  (V) trifluoromethyl,
(v) benzyl, which is unsubstituted or substituted with 1-3 substituents where the substituents are independently selected from:
  (I) —$C_{1-4}$alkyl,
  (II) —O—$C_{1-4}$alkyl,
  (III) halo, and
  (IV) trifluoromethyl,
or where $R^{10a}$ and $R^{11a}$ join to form a ring selected from azetidinyl, pyrrolidinyl, piperidinyl, azepanyl, piperazinyl, or morpholinyl, which ring is unsubstituted or substituted with 1-5 substituents each independently selected from:
  (I) —$C_{1-4}$alkyl, which is unsubstituted or substituted with 1-3 fluoro,
  (II) —O—$C_{1-4}$alkyl, which is unsubstituted or substituted with 1-3 fluoro,
  (III) halo,
  (IV) hydroxy,
  (V) phenyl, and
  (VII) —$COR^9$.

In an embodiment of the present invention $R^{10a}$ and $R^{11a}$ are each independently selected from:
(i) hydrogen,
(ii) —$C_{1-4}$alkyl, which is unsubstituted or substituted with 1-3 halo,
(iii) —$C_{5-6}$cycloalkyl,
(iv) phenyl, and
(v) benzyl,
or where $R^{10a}$ and $R^{11a}$ join to form a ring selected from pyrrolidinyl, piperidinyl, piperazinyl, or morpholinyl, which ring is unsubstituted or substituted with 1-3 substituents each independently selected from:
  (I) —$C_{1-4}$alkyl,
  (II) halo, and
  (III) hydroxy.

In an embodiment of the present invention $R^{12}$ is selected from:
(i) —$C_{1-6}$alkyl, which is unsubstituted or substituted with 1-3 fluoro,
(ii) —$C_{3-6}$cycloalkyl,
(iii) phenyl or heterocycle, wherein heterocycle is selected from: pyridinyl, pyrimidinyl, pyrazinyl, piperidinyl, piperazinyl, pyrrolidinyl, thienyl, or morpholinyl,
  which phenyl or heterocycle is unsubstituted or substituted with 1-3 substituents independently selected from:
    (I) —$C_{1-4}$alkyl,
    (II) —O—$C_{1-4}$alkyl, and
    (III) halo,
(iv) benzyl, which is unsubstituted or substituted with 1-3 substituents independently selected from:
  (I) —$C_{1-4}$alkyl, and
  (II) halo.

In an embodiment of the present invention $R^{12}$ is selected from:
(i) —$C_{1-4}$alkyl,
(ii) —$C_{3-6}$cycloalkyl,
(iii) phenyl, and
(iv) benzyl.

It is to be understood that where one or more of the above recited structures or substructures recite multiple substituents having the same designation each such variable may be the same or different from each similarly designated variable. For example, $R^2$ is recited four times in formula I, and each $R^2$ in formula I may independently be any of the substructures defined under $R^2$. The invention is not limited to structures and substructures wherein each $R^2$ must be the same for a given structure. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^{10}$ and $R^{11}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$alkynyl is defined to identify the group as having 2, 3, 4, 5 or 6 carbons in a linear or branched arrangement, such that $C_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 4- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The terms "bond" and "absent" are in certain instances herein used interchangeably to refer to an atom (or chemical moiety) which is not present in a particular embodiment of the invention. In such embodiments, the atoms adjacent the "bond" or "absent" atom are simply bonded to one another. For example, in certain embodiments of the invention described and claimed herein, where -$A^1$-$A^2$-$A^3$-links $B^4$ to $E^2$, $A^1$ is defined as $CR^{13}R^{14}$ while $A^2$ and $A^3$ are described as "absent". In such a molecule, it is understood that $A^1$ is bonded directly to the moiety adjacent $A^3$, i.e. the moiety $E^2$, resulting in the sub-structure $B^4$-$A^1$-$E^2$. The absence of a specific atom or moiety, particularly an atom or moiety which serves to link or connect other atoms or moieties, does not imply that such other atoms or moieties are not linked.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 µg) were incubated in 1 ml of binding buffer [10 mM HEPES, pH 7.4, 5 mM $MgCl_2$ and 0.2% bovine serum albumin (BSA)] containing 10 pM $^{125}$I-CGRP and antagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 µl) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 µg/ml streptomycin at 37° C., 95% humidity, and 5% $CO_2$. For cAMP assays, cells were plated at $5\times10^5$ cells/well in 96-well poly-D-lysine-coated plates (Becton-Dickinson) and cultured for ~18 h before assay. Cells were washed with phosphate-buffered saline (PBS, Sigma) then pre-incubated with 300 µM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) *Br. J. Pharmacol.* 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 $cm^2$ flasks. CRLR and RAMP expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM $MgCl_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \% I_{max}/100)}{1 + ([Drug]/K_i(1 + [Radiolabel]/K_d)^{nH}} + (Y_{max} - Y_{min})(\% I_{max} - \% I_{min}/100)$$

Where Y is observed CPM bound, $Y_{max}$ is total bound counts, Y min is non specific bound counts, (Y max−Y min) is specific bound counts, % 1 max is the maximum percent inhibition, % 1 min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 μM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 μM. Such a result is indicative of the intrinsic activity of the compounds in use as antagonists of CGRP receptors.

The ability of the compounds of the present invention to act as CGRP antagonists makes them useful pharmacological agents for disorders that involve CORP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a $5\text{-}HT_{1B/1D}$ agonist, for example sumatriptan, naratriptan, zolmitriptan, eletriptan, almotriptan, frovatriptan, donitriptan, and rizatriptan, a $5\text{-}HT_{1D}$ agonist such as PNU-142633 and a $5\text{-}HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lomoxicam, ketorolac, etodolac, mefenamic acid, meclofenamic acid, flufenarmic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5HT$_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 10 milligrams to about 1000 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following schemes and examples. Starting materials are made according to procedures known in the art or as illustrated herein.

The compounds of the present invention can be prepared readily according to the following schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following schemes.

The synthesis of spirohydantoin intermediates may be conducted as described in Schemes 1-9. Spirohydantoin intermediates bearing $R^4$, $R^5$, $R^{13}$, $R^{14}$ and $R^{15}$ may be prepared by employing appropriately substituted starting materials or by derivatization of any intermediates and/or final products as desired by methods known in the art.

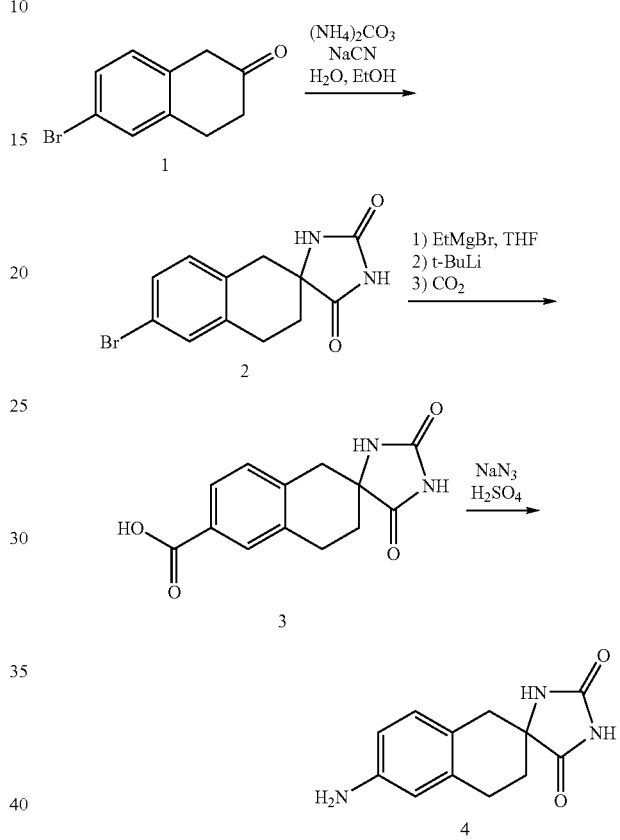

Commercially available 6-bromo-2-tetralone (1) may be readily converted to the spirohydantoin 2 under Bucherer-Bergs conditions, using ammonium carbonate and either sodium cyanide or potassium cyanide. Other 2-tetralones may be readily accessed using a variety of literature methods, such as the Friedel-Crafts reaction of arylacetyl chlorides with ethene as described by Burckhalter and Campbell (*J. Org. Chem.* 1961, 26, 4232) and converted to the corresponding spirohydantoins analogously. In Scheme 1, treatment of spirohydantoin 2 with ethyl magnesium bromide followed by tert-butyllithium effects metal-halogen exchange and the resulting aryllithium species is quenched with carbon dioxide to give acid 3. A Schmidt reaction of 3 with hydrazoic acid may be used to provide aniline 4, as reviewed by Wolff (*Org. React.* 1946, 3, 307). Alternatively, a modified Curtius rearrangement using 3 and diphenylphosphoryl azide according to the procedure of Yamada and coworkers (*Tetrahedron* 1974, 30, 2151) can provide aniline 4 via either its tert-butyl or benzyl carbamate derivatives.

SCHEME 2

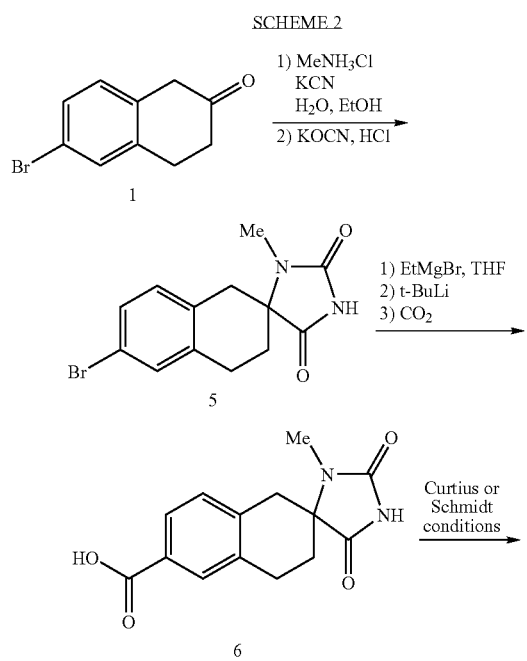

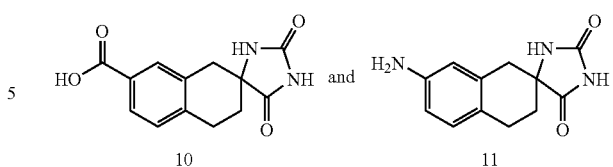

Scheme 4 details the synthesis of the key indane-based spirohydantoin intermediates. 2-Indanone (12) is converted to the spirohydantoin 13 via Bucherer-Bergs chemistry as shown. Treatment of 13 with nitric acid provides the 5-nitroindane derivative 14, which may be reduced to the corresponding aniline 15 under catalytic hydrogenation conditions. Alternatively, a two-step process can be employed to convert 2-indanone (12) into the N-methylspirohydantoin 16. Treatment of 12 with potassium cyanide and methylamine hydrochloride affords an amino nitrile which is converted to the spirohydantoin 16 using potassium cyanate and acetic acid. Subjection of 16 to the nitration-reduction sequence used for 13 leads to the corresponding aniline 18, as detailed in Scheme 4.

In Scheme 2, treatment of 6-bromo-2-tetralone (1) with methylamine hydrochloride and potassium cyanide, followed by potassium cyanate and hydrochloric acid, provides the methylated hydantoin derivative 5. Analogous procedures to those described in Scheme 1 may be used to provide acid 6 and aniline 7.

Scheme 3 illustrates a route to 7-substituted tetralin derivatives 10 and 11. 3-Bromophenylacetic acid is converted to the corresponding acid chloride and this is subjected to Friedel-Crafts reaction with ethene, affording the 7-bromo-2-tetralone 9. This intermediate may be elaborated using the procedures described in Scheme 1 to provide the acid (10) and aniline (11).

SCHEME 3

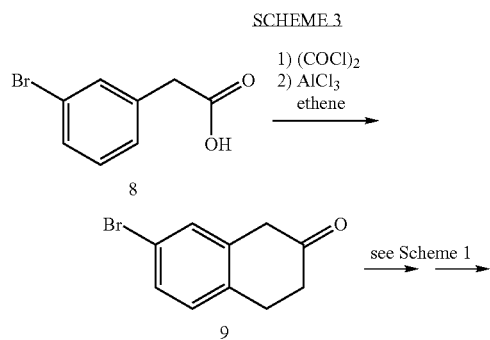

SCHEME 4

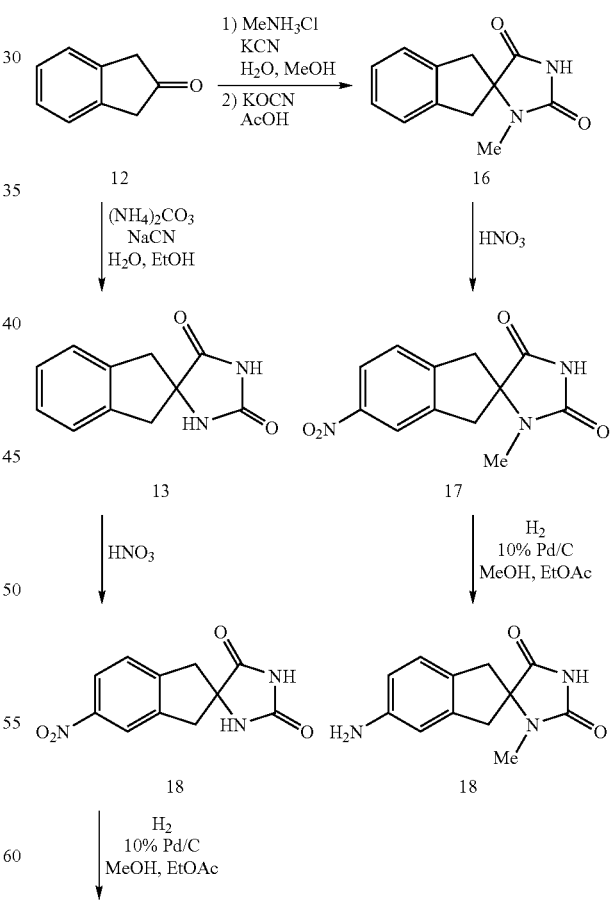

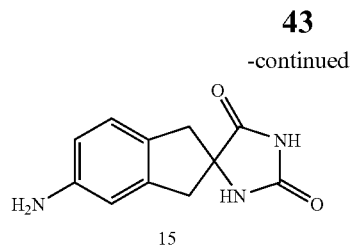

15

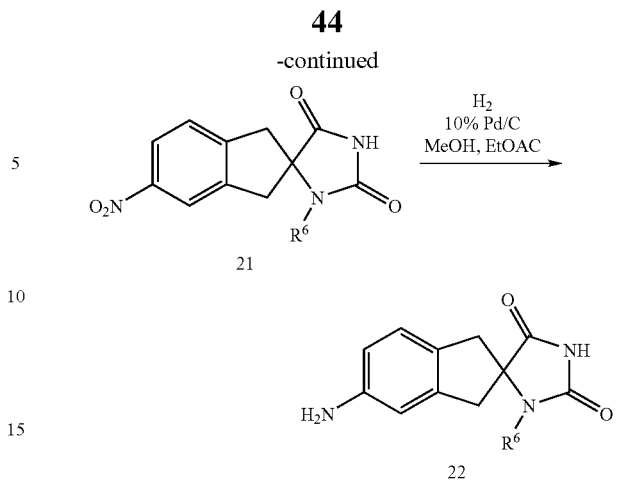

21

22

Spirohydantoin intermediates may be resolved to give pure enantiomers using techniques familiar to those skilled in the art. For example, chromatography of the nitro intermediate 17 on a ChiralPak AD column can be used to provide the individual enantiomers (R)-17 and (S)-17, and these enantiomers may be reduced to the corresponding anilines [(R)-18 and (S)-18] by catalytic hydrogenation. Use of standard coupling procedures using enantiomerically pure anilines affords the individual enantiomers of the final products. Resolution may be effected by other methodologies, such as fractional crystallization of diastereomeric salts, and it may be carried out on other synthetic intermediates or on the final products. Alternatively, an asymmetric synthesis of a key intermediate, such as an amino acid precursor of a spirohydantoin, could be used to provide an enantiomerically enriched final product.

Spirohydantoin compounds containing $R^6$ substituents other than hydrogen or methyl may be prepared by methods analogous to those for the cases where $R^6$ is methyl in Scheme 2 and Scheme 4. Alternatively, a suitably protected spirohydantoin intermediate may be derivatized as shown in Scheme 5.

SCHEME 5

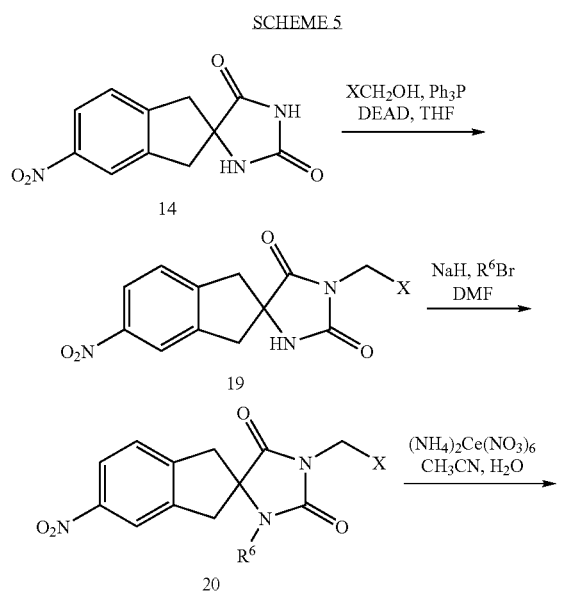

The route illustrated in Scheme 5 uses a Mitsunobu reaction to selectively protect the imide nitrogen of spirohydantoin 14 with, for example, X=4-methoxyphenyl. Other alkylation conditions may also be employed in this protection step. The protected spirobydantoin 19 may be alkylated with a variety of $R^6$ groups using sodium hydride or another base to deprotonate the spirohydantoin. In the example shown, the bromide $R^6Br$ is utilized to effect the alkylation, but a variety of other $R^6$ derivatives, such as chlorides or sulfonates may be used. Other conditions, such as copper or palladium promoted arylation or heteroarylation reactions may also be employed to install aryl or heteroaryl $R^6$ groups. The spirohydantoin product 20 is then deprotected to give 21. In Scheme 5, ammonium cerium (IV) nitrate is used to remove the 4-methoxybenzyl protecting group but the choice of deprotection conditions may vary depending on the nature of X. Finally, hydrogenation conditions may be used to provide intermediate 22, in analogy with the previous schemes.

Aniline intermediates, such as those described in Schemes 1-5, may be converted to a variety of other key intermediates that are useful in the synthesis of the compounds of the present invention. For example, Scheme 6 illustrates methodology for conversion of a representative aniline into several quinoline intermediates.

SCHEME 6

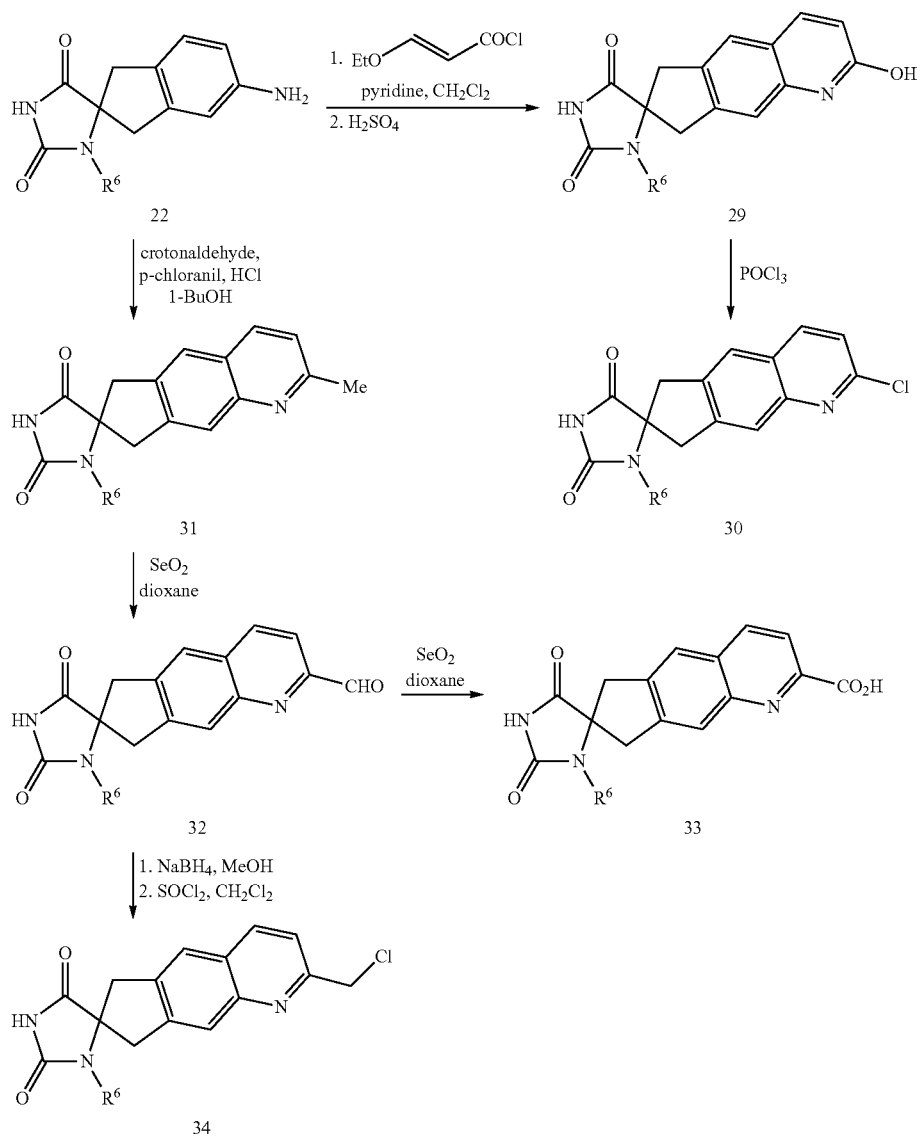

Aniline 22 may be acylated with (E)-3-ethoxyacryloyl chloride and treatment of the resulting amide with sulfuric acid leads to hydroxyquinoline 29, which can be converted to the corresponding chloride 30 by heating in phosphorus oxychloride. Condensation of aniline 22 with crotonaldehyde in the presence of acid and an oxidant affords the 2-methylquinoline 31. The use of other aldehydes under similar conditions can lead to alternatively substituted quinolines. Oxidation of quinoline 31 with selenium dioxide can provide either aldehyde 32 or carboxylic acid 33, depending on the amount of oxidant used and the duration of the reaction. Reduction of aldehyde 32 with sodium borohydride provides the corresponding alcohol, and treatment of this with thionyl chloride may be used to give the chloride 34. Intermediates such as 30, 32, 33 and 34 may be converted to compounds of the present invention using a variety of known methodology. While the methodology shown in Scheme 6 is exemplified using aniline 22, it is understood that it may be applied to a variety of aniline substrates, such as those described herein, in order to provide various quinoline intermediates.

SCHEME 7

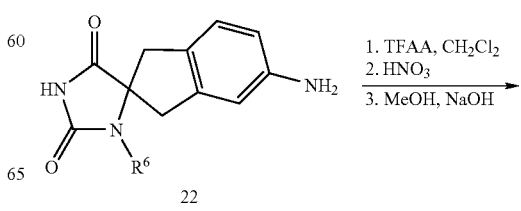

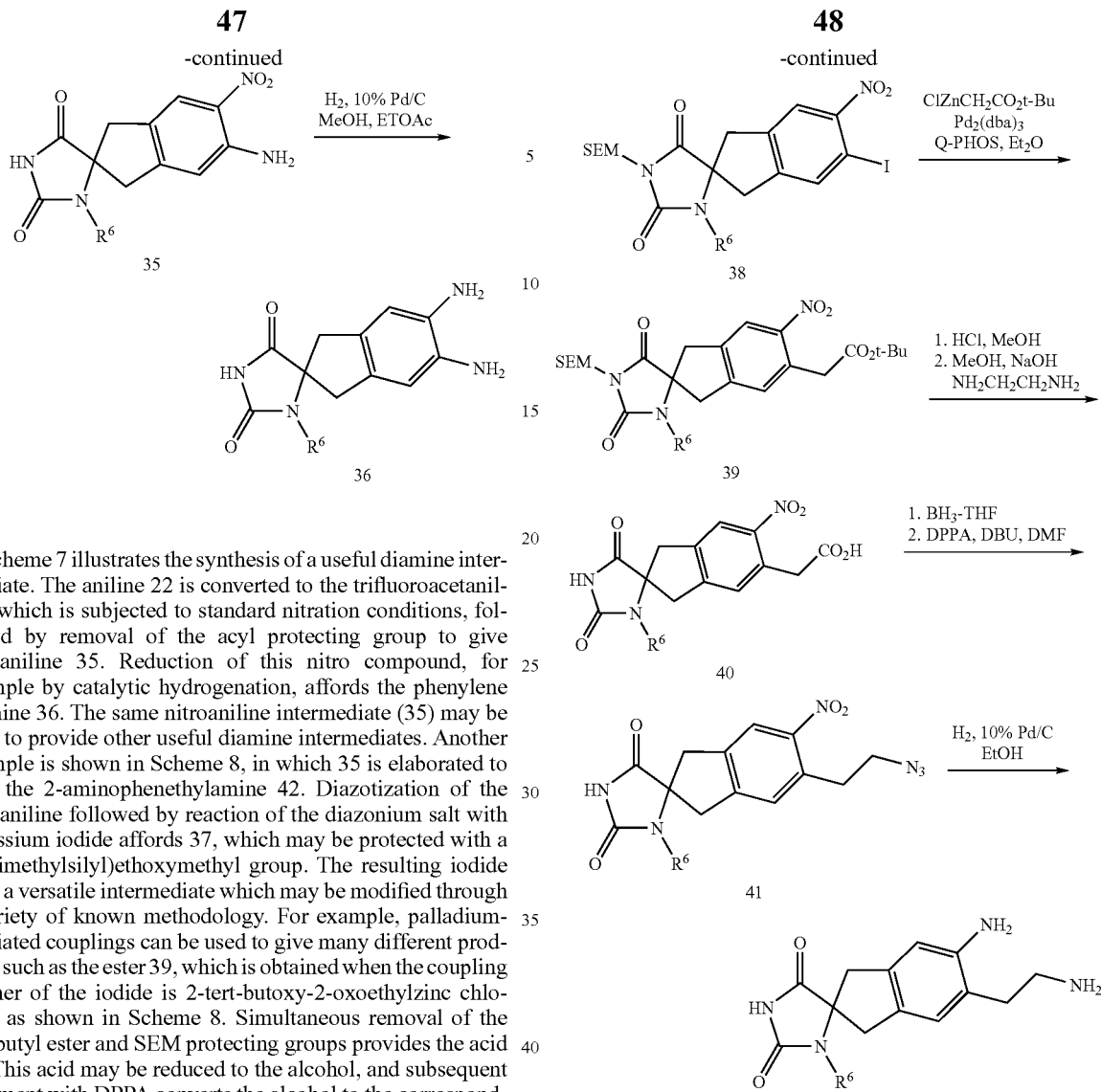

Scheme 7 illustrates the synthesis of a useful diamine intermediate. The aniline 22 is converted to the trifluoroacetanilide, which is subjected to standard nitration conditions, followed by removal of the acyl protecting group to give nitroaniline 35. Reduction of this nitro compound, for example by catalytic hydrogenation, affords the phenylene diamine 36. The same nitroaniline intermediate (35) may be used to provide other useful diamine intermediates. Another example is shown in Scheme 8, in which 35 is elaborated to give the 2-aminophenethylamine 42. Diazotization of the nitroaniline followed by reaction of the diazonium salt with potassium iodide affords 37, which may be protected with a 2-(trimethylsilyl)ethoxymethyl group. The resulting iodide 38 is a versatile intermediate which may be modified through a variety of known methodology. For example, palladium-mediated couplings can be used to give many different products, such as the ester 39, which is obtained when the coupling partner of the iodide is 2-tert-butoxy-2-oxoethylzinc chloride, as shown in Scheme 8. Simultaneous removal of the tert-butyl ester and SEM protecting groups provides the acid 40. This acid may be reduced to the alcohol, and subsequent treatment with DPPA converts the alcohol to the corresponding azide 41. Catalytic hydrogenation, or a number of other known methodologies, can be employed to reduce both the nitro and azido moieties to give the corresponding diamine 42.

SCHEME 8

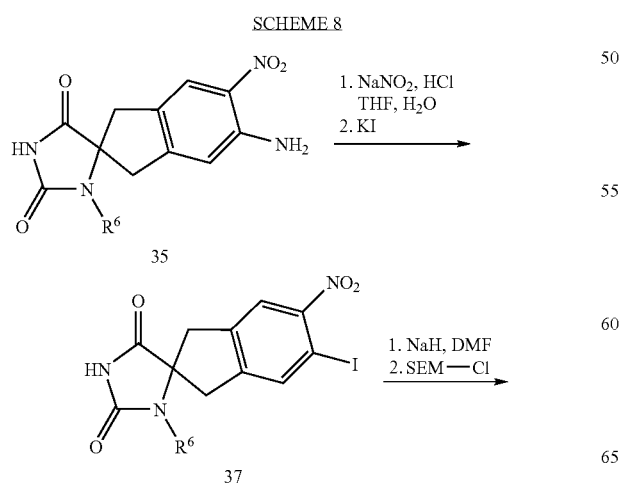

The methodology illustrated in the foregoing Schemes 6-8 describes the synthesis of some intermediates that are useful for making the compounds of the present invention. While the examples shown involve analogues of aniline 22, those skilled in the art will appreciate that such methodology may be extended to a variety of other anilines to give other useful intermediates. For example, Scheme 9 illustrates the synthesis of heterocyclic intermediates that are analogous to those in Scheme 6 but of a more general structure.

SCHEME 9

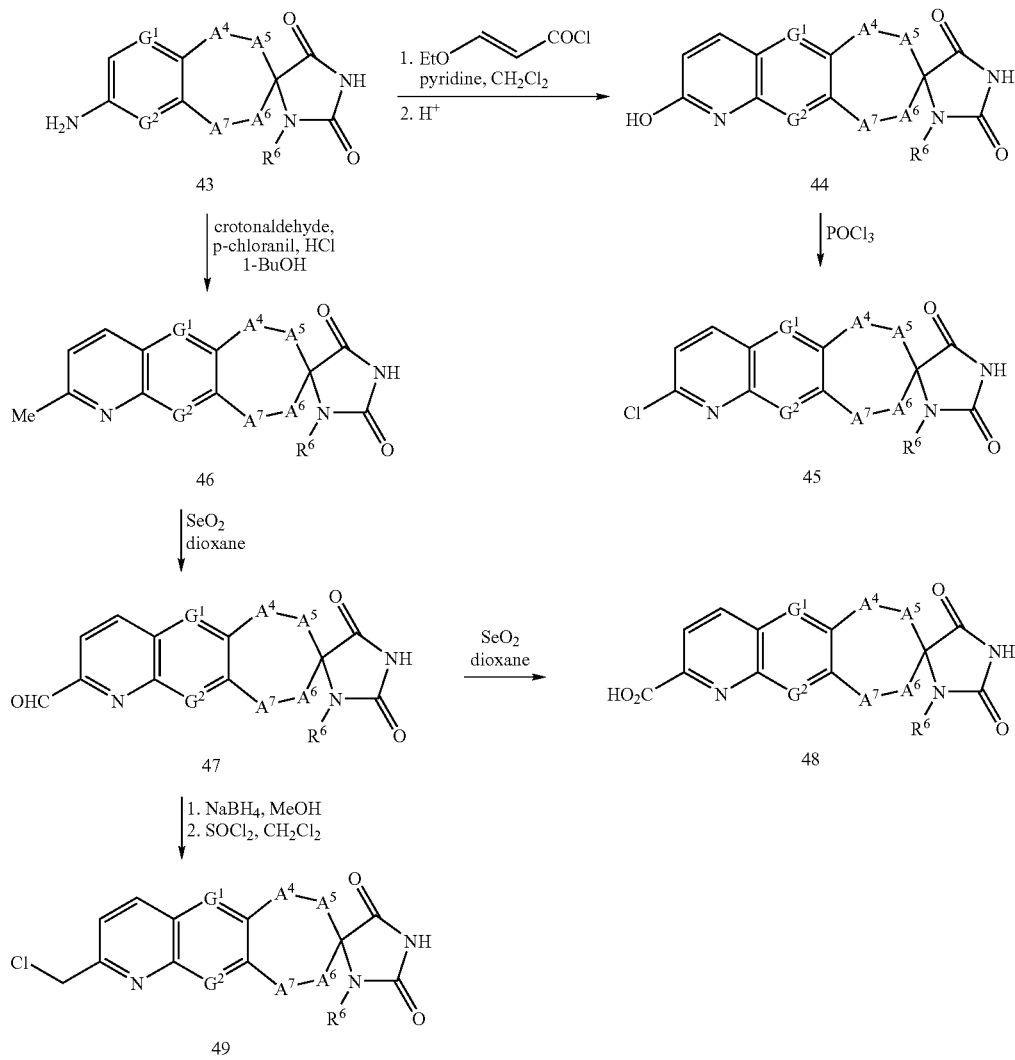

It is understood by those skilled in the art that in some cases alternative reagents or conditions may be used to effect the transformations in Scheme 9. In some cases, additional chemical steps may be required to obtain the compounds of interest, or various protecting group strategies may be employed.

The intermediates described in Schemes 6-9 may be used to synthesize the compounds of the present invention using a variety of known methodologies. Some of these methodologies are illustrated in Scheme 10. Standard reductive amination of an aldehyde like 47 with a suitable amine (RR'NH) may be used to obtain a final product of interest (50). Similarly, a standard coupling reaction may be used to convert carboxylic acid 48 to amide 51, which may be another example of the present invention when R and R' are selected appropriately.

SCHEME 10

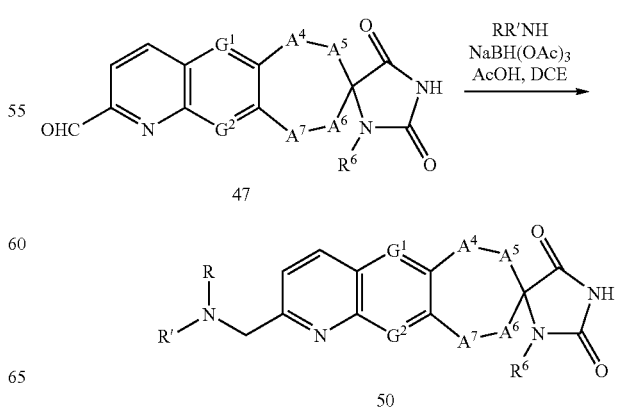

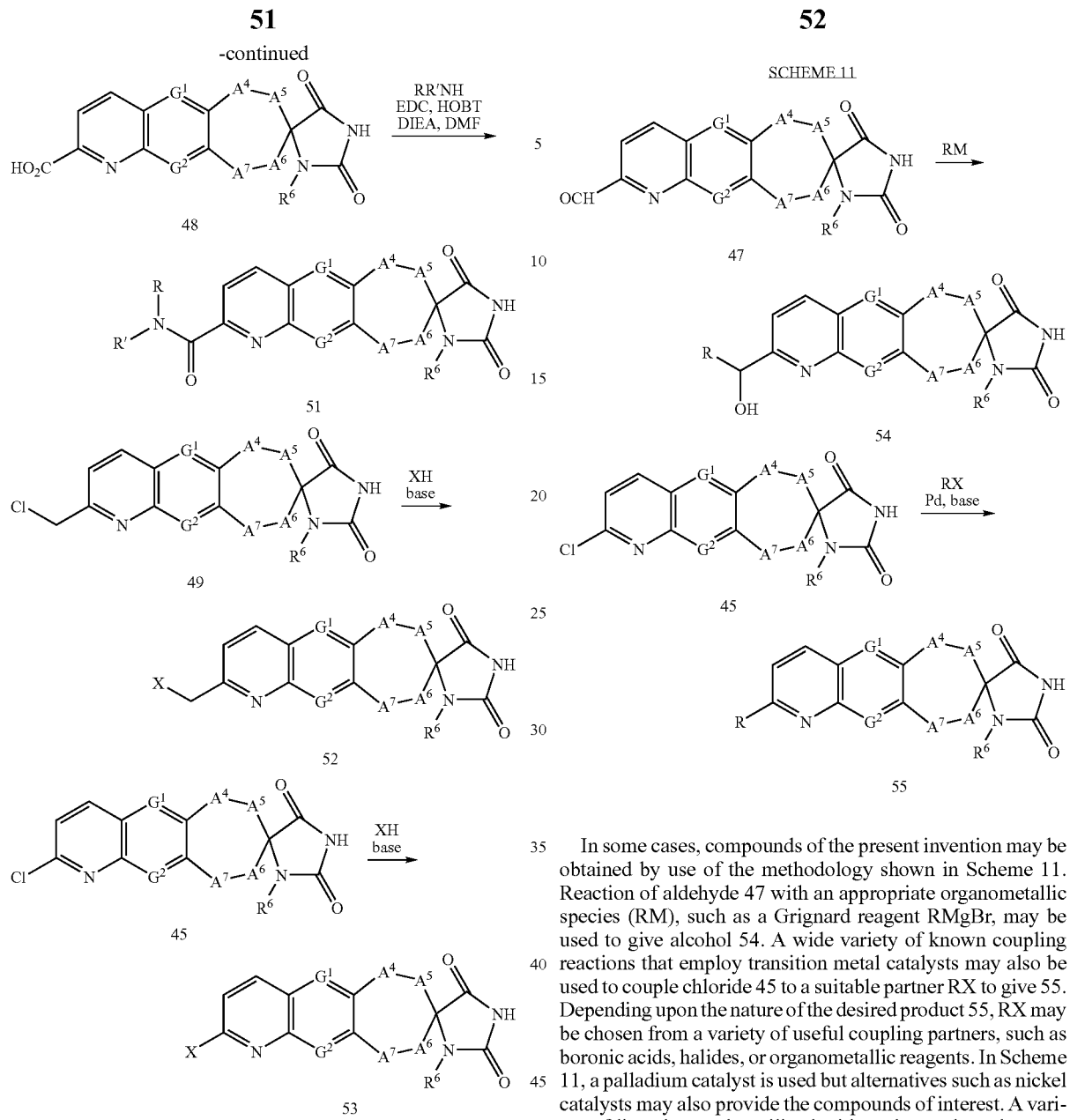

Scheme 10 also illustrates the coupling of chlorides 45 and 49 with a suitable partner (XH), usually under basic conditions, to give other compounds of the present invention (52 and 53). The precise nature of RR'NH or XH not only determines the identity of the final compound of interest, but also influences the choice of conditions under which the reaction is performed. For example, reductive amination of 47 may be performed using alternative conditions to those shown in Scheme 10, such as sodium cyanoborohydride in MeOH, depending on the exact natures of 47 and the amine. Similarly, the coupling of RR'NH and acid 48 may be carried out under a variety of known conditions, such as use of an alternative coupling reagent like PyBOP, or activation of the carboxylic acid as an acid anhydride or acid chloride. One skilled in the art will infer from precedent in the chemical literature, and from those examples given herein, suitable conditions for reaction of either 45 or 49 with XH, which is usually an amine, lactam or similar compound.

In some cases, compounds of the present invention may be obtained by use of the methodology shown in Scheme 11. Reaction of aldehyde 47 with an appropriate organometallic species (RM), such as a Grignard reagent RMgBr, may be used to give alcohol 54. A wide variety of known coupling reactions that employ transition metal catalysts may also be used to couple chloride 45 to a suitable partner RX to give 55. Depending upon the nature of the desired product 55, RX may be chosen from a variety of useful coupling partners, such as boronic acids, halides, or organometallic reagents. In Scheme 11, a palladium catalyst is used but alternatives such as nickel catalysts may also provide the compounds of interest. A variety of ligands may be utilized with such metal catalysts, as described in the literature.

Scheme 12 demonstrates how some other heterocyclic structures may be obtained from diamine precursors. The phenylenediamine 56 can be coupled to an acid $RCO_2H$ using well-known coupling reagents, such as BOP, to give an anilide intermediate which may be cyclized in situ under acidic conditions to give the benzimidazole 57. The same starting material 56 can be condensed with a suitable ketoaldehyde, as shown in Scheme 12, to give the quinoxaline product 58. The required ketoaldehyde may be synthesized using known methodology. It may be a derivative of one of the coupling partners described herein, or subsequent functionalization after quinoxaline formation may be required to provide the desired compound of the present invention. Other ring sizes may also be obtained. For example, diamine 59 reacts readily with a variety of imidate esters to afford dihydrobenzodiazepine products of structure 60. The requisite imidate ester intermediate may be obtained using known methodology, such as treatment of the corresponding nitrile with an alcohol under acidic conditions.

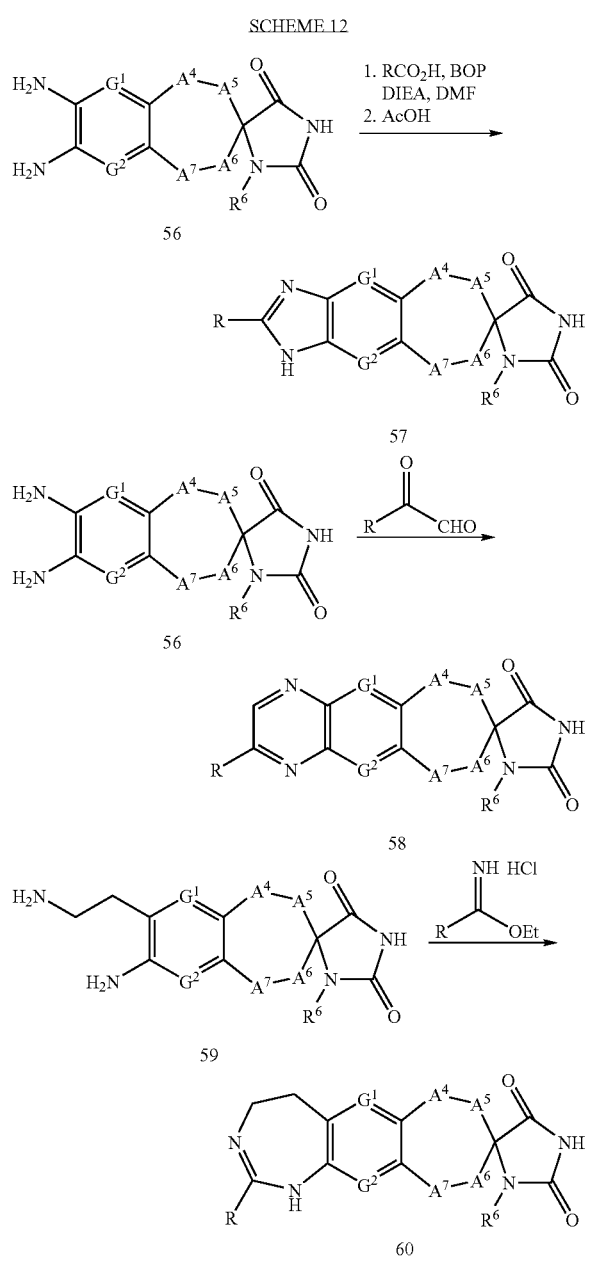

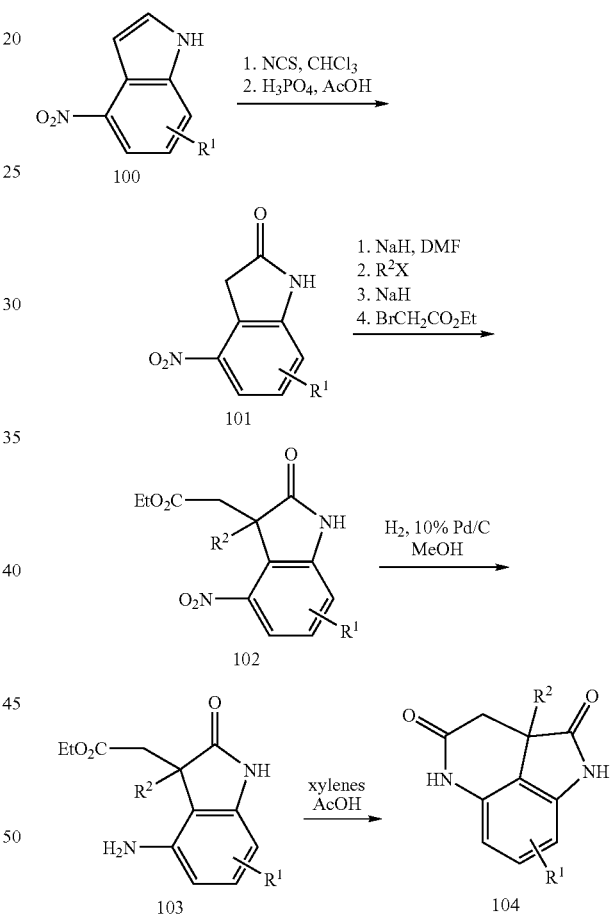

In Schemes 10-12, a number of strategies for assembling the compounds of the present invention are illustrated. It is understood that alternative methodologies may also be employed in the synthesis of compounds of interest. The exact choice of reagents, solvents, temperatures, and other reaction conditions, depends upon the nature of the intended product. In some cases, appropriate protecting group strategies may be used. In other cases, further elaboration of the product shown in Schemes 10-12 may be required to obtain the compound of the present invention. As previously stated, the identity of the coupling partner (e.g. RR'NH, XH, or $RCO_2H$) in Schemes 10-12 must be chosen appropriately to give the compounds of the present invention. Some representative examples of the synthesis of such coupling partners are shown in the following Schemes.

Scheme 13 illustrates a route to the tricyclic oxindole 104. The 4-nitroindole 100 may be oxidized using N-chlorosuccinimide, followed by treatment with phosphoric acid in acetic acid to give the corresponding oxindole 101. A one-pot dialkylation procedure in DMF, using sodium hydride as base, can be used to provide the ester intermediate 102. A variety of $R^2$ substituents may be incorporated using this method. For example, when $R^2X$ is iodomethane the 3-methyloxindole derivative (102; $R^2$=Me) is obtained. Reduction of the nitro group via catalytic hydrogenation provides the aniline 103. This nitro reduction may also be effected using a wide range of conditions that are well known to those skilled in the art, including use of zinc, iron, or tin under acidic conditions or reduction with Raney nickel. Cyclization of 103, usually carried out by heating in xylenes in the presence of acid, affords the tricyclic oxindole 104.

Scheme 14 describes the conversion of ester 102 (from Scheme 13) into a tricyclic indoline. Treatment with Lawesson's reagent transforms 102 into the corresponding thioamide 105. This intermediate may be reduced using, for example, nickel boride or activated Raney nickel to give the aminoindoline 106, which is converted to the tricyclic 107 upon heating in xylenes in the presence of acid.

SCHEME 14

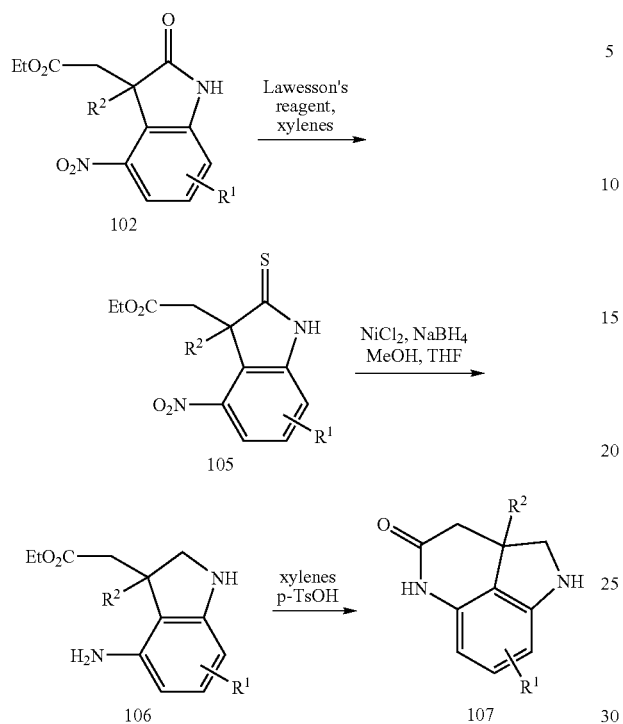

An alternative tricyclic oxindole is described in Scheme 15. The methodology is very similar to that shown in Scheme 13, with the exception that the oxindole 101 is monoalkylated instead of being dialkylated in the initial alkylation reaction. The resulting ester 108 is advanced using identical methodology to that previously described to give the tricyclic oxindole 109. Aromatization of 109 can be accomplished using a variety of mild oxidation reagents, such as $MnO_2$ in toluene, to give the tricyclic intermediate 110.

SCHEME 15

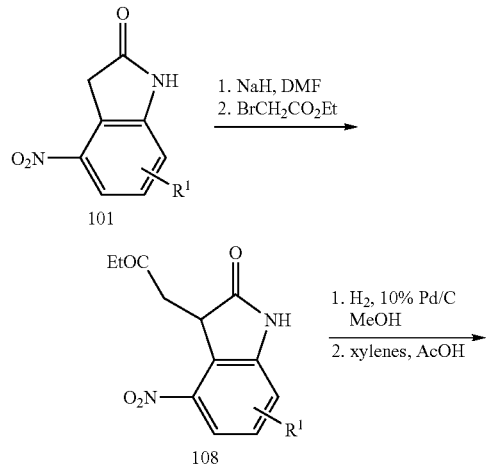

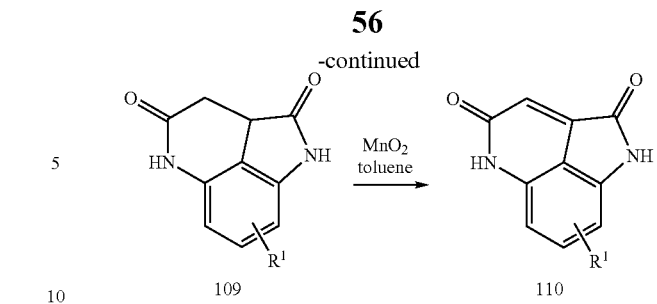

In some cases, it is desirable to perform the couplings shown in Schemes 10-12 with a non-tricyclic intermediate and convert the product of this coupling to a tricyclic compound in a subsequent step. A representative example of such an intermediate is shown in Scheme 16. 2-Choro-3-nitrobenzoic acid 111 is reacted with methyl glycinate in tert-butanol to give the anthranilic acid derivative 112. Treatment of 112 with diphenylphosphoryl azide under basic conditions initially gives the corresponding acyl azide, which undergoes a Curtius rearrangement that leads to the benzimidazolone 113. Intermediate 113 may be coupled with a number of the spirohydantoins described herein. Subsequent reduction of the nitro group and cyclization, in analogy with other examples in these schemes, may yield a compound of the present invention.

SCHEME 16

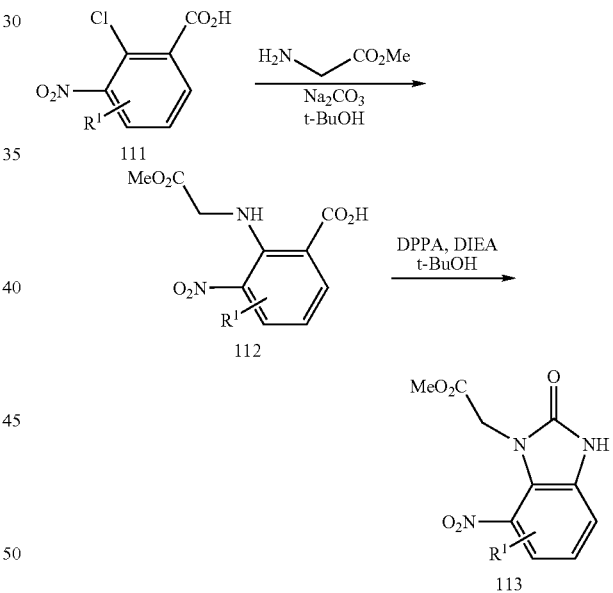

A route to other benzimidazolone intermediates is shown in Scheme 17. The starting material is the 3-nitro-1,2-phenylenediamine 114, which may be obtained from a variety of published routes and known methodologies (for example *Leibigs Ann. Chem.* 1989, 539-544; *J Med. Chem.* 1995, 38, 4367-4379). In this scheme, 114 is treated with p-toluenesulfonyl chloride, followed by triphosgene, to give the protected nitrobenzimidazolone 115. Elaboration of 115 is carried out in analogy with previous schemes to provide the tricyclic benzimidazolone 117, which may be alkylated on the anilide nitrogen to give a number of possible products. In the example shown, alkylation with iodomethane is carried out in DMF to provide the N-methylated analogue. Deprotection may be effected with sulfuric acid to provide the tricyclic intermediate 118.

SCHEME 17

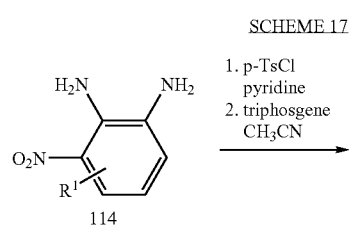
114

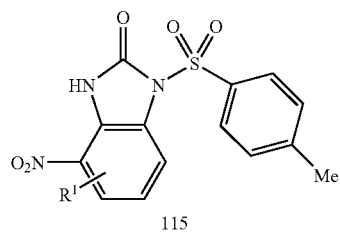
115

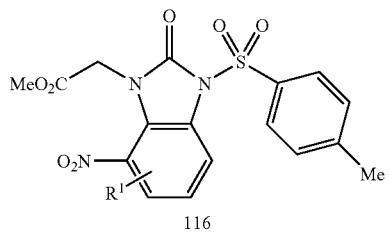
116

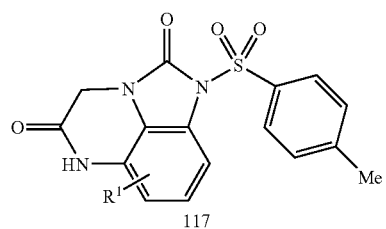
117

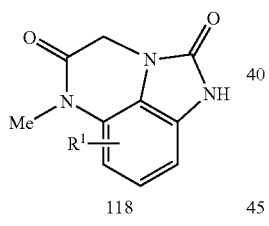
118

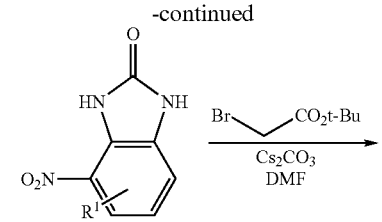
119

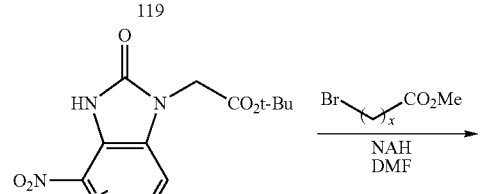
120

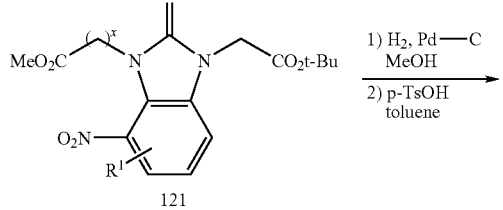
121

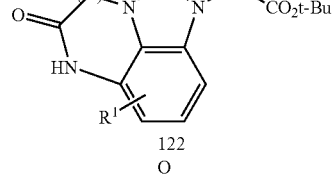
122

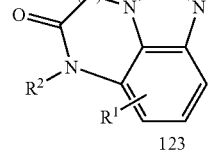
123

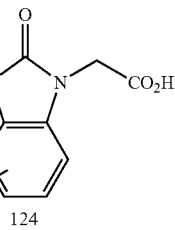
124

Scheme 18 illustrates a general route to substituted benzimidazolone tricyclic carboxylic acid 124. Starting with the appropriately substituted 3-nitro-1,2-phenylenediamine starting material 114, the nitrobenzimidazolone 119 may be synthesized by treatment with phosgene or one of a number of carbonylation reagents, including carbonyldiimidazole and urea. Alternatively, a substituted benzimidazolone may be nitrated in order to provide 119 (*J. Org. Chem.* 1995, 60, 1565-1582).

SCHEME 18

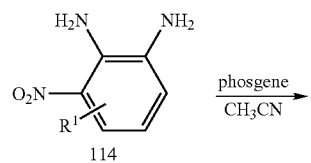
114

Alkylation of the nitrobenzimidazolone 119 under basic conditions with a suitable bromoacetate, such as tert-butyl bromoacetate, can afford the monoacetyl derivative 120. Further alkylation of the benzimidazolone is accomplished using, for example, sodium hydride as base followed by a suitable bromide to give the benzimidazolone 121. In the example shown, bromo esters with different chain lengths may be used to provide a number of different products. In some cases, depending upon the selection of $R^1$, these alkylations may result in mixtures of regioisomers, and the mixtures of 120 or 121 may be separable by chromatography. Reduction of the nitro compound 121 to the corresponding aniline may be accomplished via a number of standard methods, such as catalytic hydrogenation, and the aniline may be cyclized to give anilide 122 under acidic conditions. In Scheme 18, the resultant anilide is N-alkylated to give 123. For example, when R²X is iodomethane, the N-methyl analogue is obtained. Alternatively, the anilide nitrogen may be arylated using well-precedented methodology, such as treatment with an aryl bromide and a copper or palladium catalyst (*Org. Lett.* 2000, 2, 1101-1104; *J. Am. Chem. Soc.* 2001, 123, 7727-7729). Hydrolysis of the ester to reveal the acid functionality in 124 can be accomplished using either acidic or basic conditions, depending upon the nature of the ester intermediate 123. In Scheme 18, the tert-butyl ester is removed using trifluoroacetic acid.

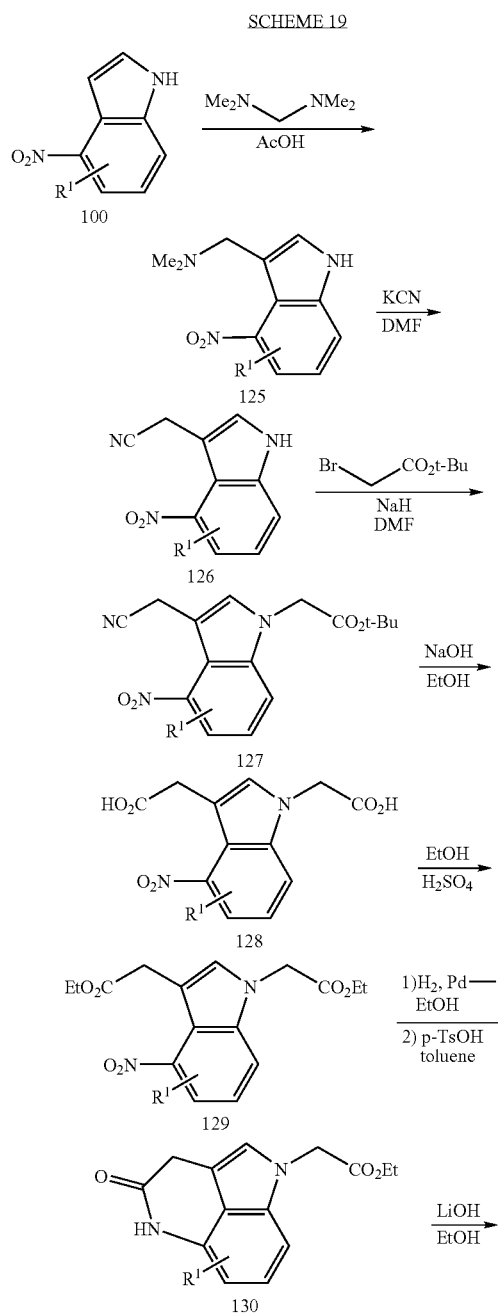

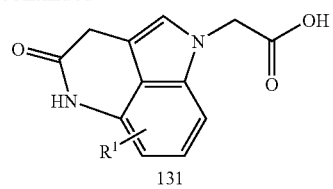

Scheme 19 illustrates a general route to substituted indole tricyclic derivative 131. The nitroindole 100 can be converted to the nitrite 126 via a two-step sequence: a Mannich reaction with N,N,N',N'-tetramethyldiaminomethane followed by treatment with potassium cyanide. Alternatively, the dimethylamine derivative 125 can be formed by reaction of the nitroindole 100 with dimethylamine and formaldehyde in a microwave reactor. N-alkylation of 126 can be accomplished by treatment with an appropriate alkylating agent under basic conditions to give esters of the general form 127. Treatment of 127 with excess sodium hydroxide may be used to hydrolyze both the nitrite and ester groups, to afford the diacid 128. Subjection of this diacid to classical esterification using EtOH and $H_2SO_4$ converts it to the corresponding diester 129. The nitro moiety may be reduced under a variety of conditions, such as catalytic hydrogenation, and the resulting aniline can be heated under acidic conditions to afford the tricyclic indole 130. Saponification of the ester is thereafter accomplished under standard conditions to provide the acid intermediate 131.

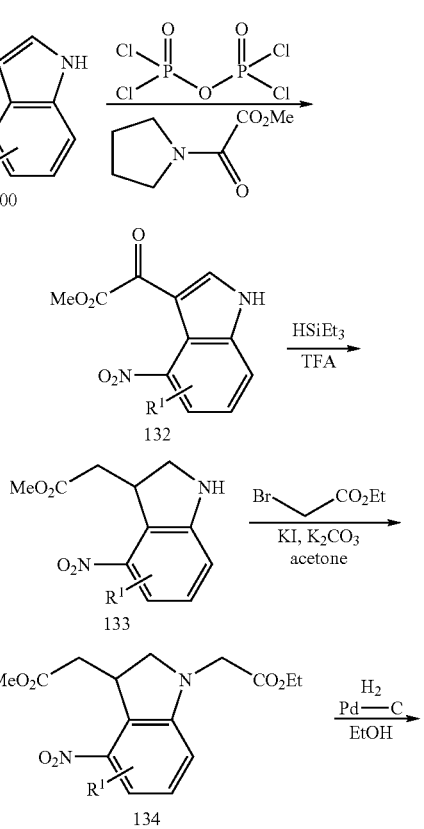

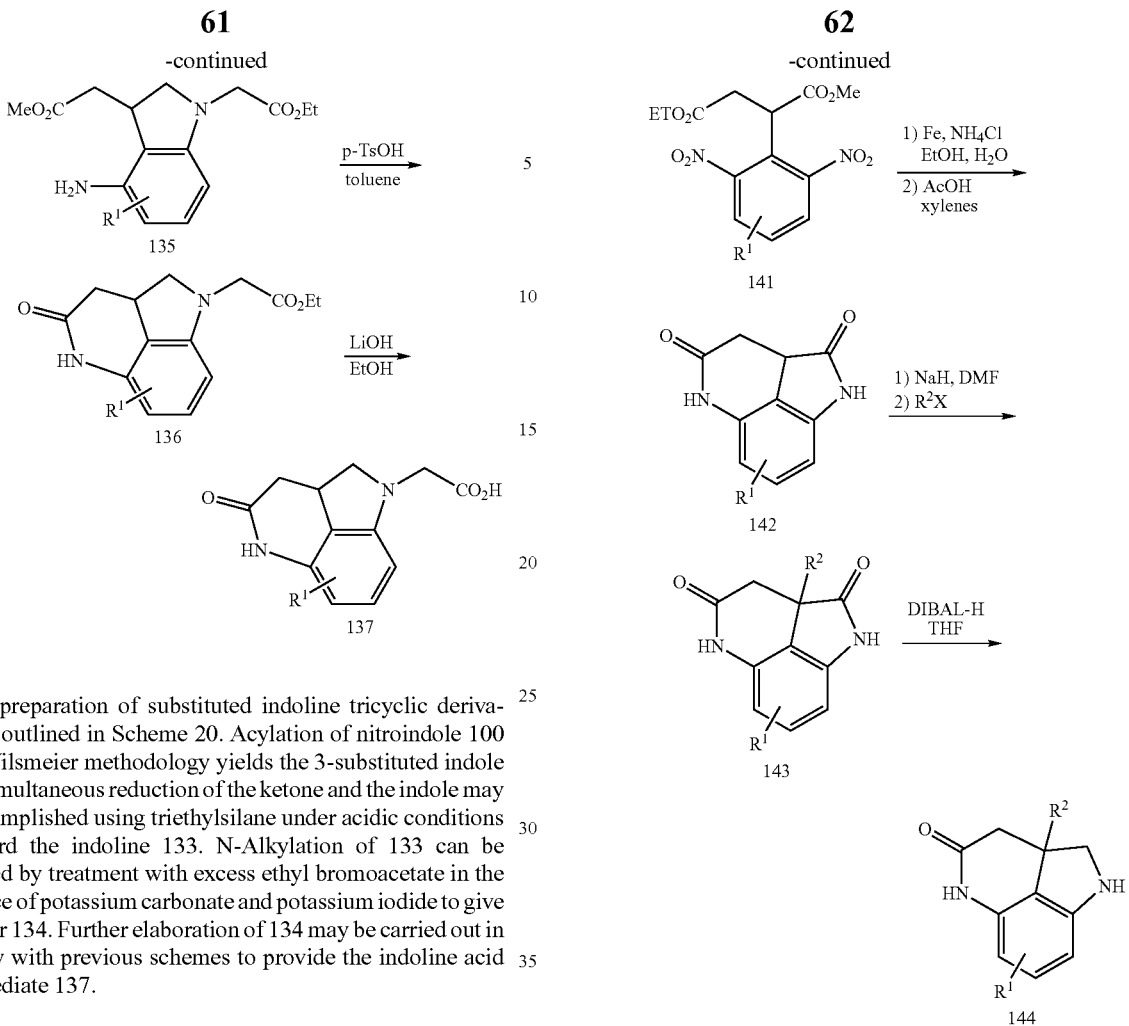

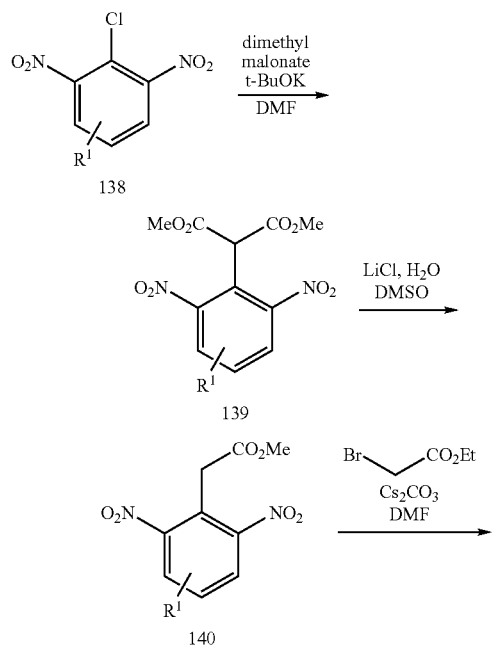

The preparation of substituted indoline tricyclic derivatives is outlined in Scheme 20. Acylation of nitroindole 100 using Vilsmeier methodology yields the 3-substituted indole 132. Simultaneous reduction of the ketone and the indole may be accomplished using triethylsilane under acidic conditions to afford the indoline 133. N-Alkylation of 133 can be achieved by treatment with excess ethyl bromoacetate in the presence of potassium carbonate and potassium iodide to give the ester 134. Further elaboration of 134 may be carried out in analogy with previous schemes to provide the indoline acid intermediate 137.

Another route to substituted indoline tricyclic derivatives is shown in Scheme 21. Following condensation of dimethyl malonate with dinitrochlorobenzene 138, treatment of the product 139 with LiCl in wet DMSO provides the phenylacetate derivative 140. Alkylation of compound 140 with ethyl bromoacetate affords the succinate 141, and sequential nitro reduction and acid-catalyzed cyclization affords the tricycle 142. Treatment of 142 with base followed by an electrophile $R^2X$ provides the substituted derivative 143, which may be selectively reduced to the indoline 144 using DIBAL-H. Simple modifications of these routes, including different protecting group strategies, application of well-precedented methodology, and the use of starting materials and reagents other than those described in the foregoing schemes, may be used to provide other acids of interest.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

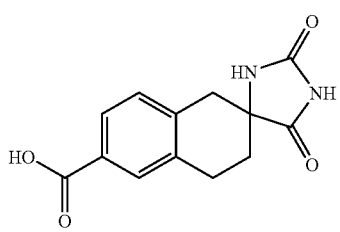

(±)-6'-Carboxy-3',4'-dihydro-1'H-spiro[imidazolidine-4,2'-naphthalene]-2,5-dione Step A. (±)-6'-Bromo-3',4'-dihydro-1'H-spiro[imidazolidine-4,2'-naphthalene]-2,5-dione A stirred mixture of 6-bromo-2-tetralone (17.6 g, 78.2 mmol), sodium cyanide (9.58 g, 195 mmol), and ammonium carbonate (97.7 g, 1.02 mol) in $H_2O$ (100 mL) and EtOH (100 mL) was heated to 70° C. for 3 h, then allowed to cool to ambient temperature. The precipitate was collected by filtration and washed with $H_2O$ (5×200 mL). Drying in vacuo afforded the title compound. MS: m/z 297 (M+1).

Step B. (±)-6'-Carboxy-3',4'-dihydro-1'H-spiro[imidazolidine-4,2'-naphthalene]-2,5-dione To a stirred suspension of (±)-6'-bromo-3',4'-dihydro-1'H-spiro[imidazolidine-4,2'-naphthalene]-2,5-dione (14.9 g, 50.5 mmol) in THF (1.2 L), at −70° C., was added dropwise ethyl magnesium bromide (3.0 M in THF, 51 mL, 152 mmol). The resulting mixture was stirred for 10 min, then tert-butyllithium (1.7 M in pentane, 180 mL, 305 mmol) was added dropwise over 30 min. Stirring was continued at −70° C. for 20 min, then additional tert-butyllithium (1.7 M in pentane, 60 mL, 102 mmol) was added dropwise over 10 min. After a further 30 min, $CO_2$ (g) was bubbled into the reaction mixture until LCMS analysis indicated complete reaction. The mixture was allowed to warm slowly to ambient temperature and the THF was removed in vacuo. The residue was suspended in $H_2O$ and the solution was adjusted to pH=1-2 by the addition of conc. hydrochloric acid, to a final volume of about 500 mL. The mixture was filtered and the isolated solid was washed with $H_2O$ (4×100 mL) then dried in vacuo. Trituration of this crude solid with EtOH provided the title compound. MS: m/z=261 (M+1).

INTERMEDIATE 2

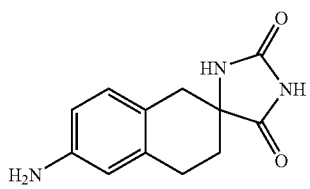

(±)-6'-Amino-3',4'-dihydro-1'H-spiro[imidazolidine-4,2'-naphthalene]-2,5-dione

Step A. (±)-6'-Amino-3',4'-dihydro-1'H-spiro[imidazolidine-4,2'-naphthalene]-2,5-dione A stirred mixture of (±)-6'-carboxy-3',4'-dihydro-1'H-spiro[imidazolidine-4,2'-naphthalene]-2,5-dione (described in Intermediate 1) (1.50 g, 5.76 mmol), and sodium azide (749 mg, 11.53 mmol) in conc. $H_2SO_4$ (30 mL) was heated to 50° C. for 2 h, then allowed to cool to ambient temperature. The mixture was adjusted to pH 8 by addition of 6 N aqueous NaOH and concentrated in vacuo to precipitate a solid. The precipitate was collected by filtration and washed extensively with $H_2O$. Drying in vacuo afforded the title compound. MS: m/z=232 (M+1).

INTERMEDIATE 3

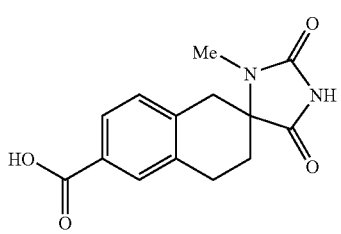

(±)-6'-Carboxy-3-methyl-3',4'-dihydro-1'H-spiro[imidazolidine-4,2'-naphthalene]-2,5-dione Step A. (±)-6'-Bromo-3-methyl-3',4'-dihydro-1'H-spiro[imidazolidine-4,2'-naphthalene]-2,5-dione A mixture of 6-bromo-2-tetralone (1.00 g, 4.44 mmol) and methylamine hydrochloride (300 mg, 4.44 mol) in $H_2O$ (1 mL) and EtOH (1.5 mL) was stirred at ambient temperature for 20 min. Potassium cyanide (289 mg, 4.44 mmol) was added and stirring was continued for 18 h. The mixture was added dropwise to a stirred solution of 1.0 N aqueous HCl (4.5 mL) at 0° C., then potassium cyanate (360 mg, 4.44 mmol) was added portionwise. The stirred mixture was heated to 95° C. and conc. hydrochloric acid (0.44 mL) was added dropwise. The reaction mixture was heated at this temperature for 1 h, allowed to cool, and extracted with $CH_2Cl_2$ (80 mL). The organic extract was dried over $Na_2SO_4$, filtered, and concentrated to dryness. The crude product was purified by silica gel chromatography, eluting with a gradient of $CH_2Cl_2$:MeOH—100:0 to 90:10, to provide a crude sample of the title compound (ca. 70% pure). Trituration with EtOH afforded the title compound. MS: m/z=311 (M+1).

Step B. (±)-6'-Carboxy-3-methyl-3',4'-dihydro-1'H-spiro[imidazolidine-42'-naphthalene]-2,5-dione To a stirred suspension of (±)-6'-bromo-3-methyl-3',4'-dihydro-1'H-spiro[imidazolidine-4,2'-naphthalene]-2,5-dione (211 mg, 0.682 mmol) in THF (30 mL), at −70° C., was added dropwise ethyl magnesium bromide (1.0 M in THF, 1.37 mL, 1.37 mmol). The resulting mixture was stirred for 15 min, then tert-butyllithium (1.7 M in pentane, 1.61 mL, 2.73 mmol) was added dropwise. After a further 30 min, $CO_2$ (g) was bubbled into the reaction mixture until LCMS analysis indicated complete reaction. The mixture was allowed to warm slowly to ambient temperature and the THF was removed in vacuo. The residue was suspended in $H_2O$ (20 mL) and the solution was adjusted to pH=1-2 by the addition of 1.0 N hydrochloric acid, then it was saturated with NaCl (s). The mixture was filtered and the isolated solid was washed with $H_2O$ then dried in vacuo. Trituration of this crude solid with EtOH provided the title compound. MS: m/z=275 (M+1).

INTERMEDIATE 4

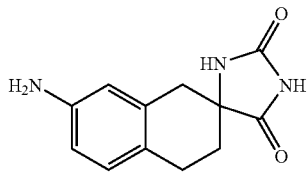

(±)-7'-Amino-3',4'-dihydro-1'H-spiro[imidazolidine-4,2'-naphthalene]-2,5-dione

Step A. 7-Bromo-2-tetralone

A solution of 3-bromophenylacetic acid (10.4 g, 48.4 mmol) in oxalyl chloride (50 mL, 0.57 mol) was stirred at ambient temperature for 5 min then at reflux for 5 h. The oxalyl chloride was removed in vacuo and the residue was dissolved in anhydrous $CH_2Cl_2$ (100 mL). This solution was added dropwise to a rapidly stirred, ice-cooled solution of $AlCl_3$ (23.2 g, 174.2 mmol) in $CH_2Cl_2$ (500 mL). A stream of ethylene gas was blown into the vortex of the stirred solution during the addition and the reaction temperature was kept at <5° C. The reaction mixture was allowed to warm to ambient temperature and then poured onto ice and stirred vigorously. The organic portion was removed and the aqueous layer extracted with $CH_2Cl_2$ (2×200 mL). The combined $CH_2Cl_2$ fractions were passed through a 2" pad of silica and concentrated to give a thick, red oil. The crude product was purified by silica gel chromatography, eluting with a gradient of hexane:EtOAc—100:0 to 75:25, to provide the title compound. MS: m/z=226 (M+1).

(±)-7'-Amino-3',4'-dihydro-1'H-spiro[imidazolidine-4,2'-naphthalene]-2,5-dione Essentially following the procedures described for Intermediate 1 and Intermediate 2, but using 7-bromo-2-tetralone in place of 6-bromo-2-tetralone, (±)-7'-amino-3',4'-dihydro-1'H-spiro[imidazolidine-4,2'-naphthalene]-2,5-dione was prepared. MS: m/z=232 (M+1).

INTERMEDIATE 5

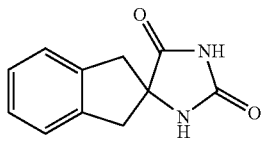

(±)Spiro[imidazolidine-4,2'-indane]-2,5-dione

Step A. (±)-Spiro[imidazolidine-4,2'-indane]-2,5-dione

A stirred mixture of 2-indanone (3.0 g, 22.6 mmol), sodium cyanide (3.3 g, 67.3 mmol), and ammonium carbonate (22 g, 228 mol) in $H_2O$ (50 mL) and EtOH (50 mL) was heated to 70° C. for 3 h, then allowed to cool to ambient temperature. The precipitate was collected by filtration and washed with $H_2O$ (5×100 mL). Drying in vacuo afforded the title compound. MS: m/z=202 (M+1).

INTERMEDIATE 6

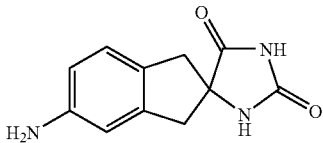

(±)-5'-Amino-spiro[imidazolidine-4,2'-indane]-2,5-dione

Step A. (±)-5'-Nitro-spiro[imidazolidine-4,2'-indane]-2,5-dione

A solution of (±)-spiro[imidazolidine-4,2'-indane]-2,5-dione (3.0 g, 14.8 mmol, described in Intermediate 5) in conc. nitric acid (33 mL) was stirred at ambient temperature for 1 h. The reaction was then poured onto crushed ice and the resultant solid was isolated by filtration. The crude material was recrystallized from ethanol to give the title compound. MS: m/z=248 (M+1).

Step B. (±)-5'-Amino-spiro[imidazolidine-4,2'-indane]-2,5-dione

To a suspension of (±)-5'-nitro-spiro[imidazolidine-4,2'-indane]-2,5-dione (1.77 g, 7.16 mmol) in EtOAc (100 mL) and MeOH (100 mL) was added 10% Pd/C (400 mg) and the reaction stirred vigorously under hydrogen (ca. 1 atm). After 1 h, the catalyst was filtered off and the filtrate was concentrated to yield the title compound. MS: m/z=218 (M+1).

INTERMEDIATE 7

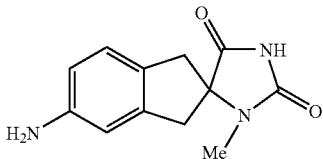

(±)-5'-Amino-3-methyl-spiro[imidazolidine-4,2'-indane]-2,5-dione

Step A. 2-(Methylamino)indane-2-carbonitrile Hydrochloride

To a mixture of 2-indanone (20.0 g, 151 mmol) in MeOH (20 mL) was added methylamine hydrochloride (10.2 g, 151 mmol). To the stirred mixture was added $H_2O$ (20 mL) and a fine homogenous slurry developed. The reaction mixture was cooled to 0° C. and KCN (9.84 g, 151 mmol) in $H_2O$ (20 mL) was added slowly over 30 min, such that the temperature did not exceed 10° C., then stirring was continued at ambient temperature for 18 h. The reaction mixture was extracted with $Et_2O$ (250 mL) and the organic extract was washed with brine (50 mL) then dried over $MgSO_4$. HCl (g) was bubbled through the vigorously stirred solution for 10 minutes and a solid precipitated. The solid was filtered, washed with $Et_2O$, and dried to yield the title compound. MS: m/z=173 (M+1).

Step B. (±)-3-Methyl-spiro[imidazolidine-4,2'-indane]-2,5-dione

To a stirred mixture of 2-(methylamino)indane-2-carbonitrile hydrochloride from Step A (6.0 g, 28.8 mmol) in AcOH (45 mL) was added a solution of potassium cyanate (4.65 g, 57 mmol) in H₂O (6 mL) and the reaction mixture was stirred for 1 h. The mixture was poured into cold H₂O (150 mL) and the precipitate was isolated by filtration, washed with H₂O and air dried. The crude solid was suspended in 1 N HCl (30 mL) and stirred to 50° C. for 2 h. The reaction mixture was cooled, filtered, and the isolated solid washed with H₂O and dried in vacuo to yield the title compound. MS: m/z=217 (M+1).

Step C. (±)-3-Methyl-5'-nitro-spiro[imidazolidine-4,2'-indane]-2,5-dione

To stirred fuming (90%) nitric acid (100 mL) was slowly added (±)-3-methyl-spiro[imidazolidine-4,2'-indane]-2,5-dione (4.5 g, 20.9 mmol) in portions over 30 min. The reaction mixture was diluted with H₂O (200 mL) and the precipitate was collected by filtration, washed with H₂O and dried in vacuo to give the title compound. MS: m/z=262 (M+1).

(±)-5'-Amino-3-methyl-spiro[imidazolidine-4,2'-indane]-2,5-dione

Essentially following the procedures described for Intermediate 6, but using (±)-3-methyl-5'-nitro-spiro[imidazolidine-4,2'-indane]-2,5-dione in place of (±)-5'-nitro-spiro[imidazolidine-4,2'-indane]-2,5-dione, the title compound was prepared. MS: m/z=232 (M+1).

INTERMEDIATE 8

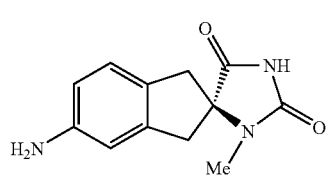

(R)-5'-Amino-3-methyl-spiro[imidazolidine-4,2'-indane]-2,5-dione

Step A. (R)-3-Methyl-5'-nitro-spiro[imidazolidine-4,2'-indane]-2,5-dione (±)-3-Methyl-5'-nitro-spiro[imidazolidine-4,2'-indane]-2,5-dione (described in Intermediate 7) was dissolved in a mixture of MeOH, CH₃CN and diethylamine and the enantiomers were resolved by HPLC, utilizing a ChiralPak AD column and eluting with CH₃CN:MeOH—90:10. The first major peak to elute was (S)-3-methyl-5'-nitro-spiro[imidazolidine-4,2'-indane]-2,5-dione and the second major peak to elute was (R)-3-methyl-5'-nitro-spiro[imidazolidine-4,2'-indane]-2,5-dione, the title compound. MS: m/z=262 (M+1).

(R)-5'-Amino-3-methyl-spiro[imidazolidine-4,2'-indane]-2,5-dione

Essentially following the procedures described for Intermediate 6, but using (R)-3-methyl-5'-nitro-spiro[imidazolidine-4,2'-indane]-2,5-dione in place of (±)-5'-nitro-spiro[imidazolidine-4,2'-indane]-2,5-dione, the title compound was prepared. MS: m/z=232 (M+1).

INTERMEDIATE 9

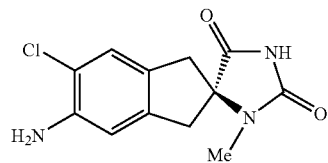

(S)-5'-Amino-6'-chloro-3-methyl-spiro[imidazolidine-4,2'-indane]-2,5-dione

Step A. (S)-5'-Amino-6'-chloro-3-methyl-spiro[imidazolidine-4,2'-indane]-2,5-dione (R)-5'-Amino-3-methyl-spiro[imidazolidine-4,2'-indane]-2,5-dione (265 mg, 1.15 mmol, described in Intermediate 8) was dissolved in AcOH (7 mL) and N-chlorosuccinimide (145 mg, 1.09 mmol) was added in one portion. The mixture was stirred at ambient temperature for 5 h, then the solvent was removed in vacuo. The residue was partitioned between saturated aqueous NaHCO₃ (20 mL) and CH₂Cl₂ (70 mL). The organic layer was dried (Na₂SO₄), filtered, and concentrated under reduced pressure. The crude product was purified by silica gel chromatography, eluting with a gradient of CH₂Cl₂:EtOAc—100:0 to 0:100, to give (R)-5'-amino-4'-chloro-3-methyl-spiro[imidazolidine-4,2'-indane]-2,5-dione, which eluted first, and the title compound, which eluted second. MS: m/z=266 (M+1).

INTERMEDIATE 10

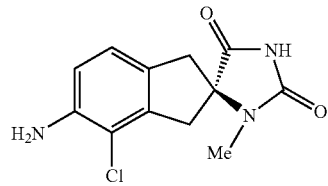

(R)-5'-Amino-4'-chloro-3-methyl-spiro[imidazolidine-4,2'-indane]-2,5-dione

Step A. (R)-5'-Amino-4'-chloro-3-methyl-spiro[imidazolidine-4,2'-indane]-2,5-dione The title compound was obtained from the same reaction as Intermediate 9. The crude product was purified by silica gel chromatography, eluting with a gradient of CH₂Cl₂:EtOAc—100:0 to 0:100, to give the title compound, which eluted first, and (S)-5'-amino-6'-chloro-3-methyl-spiro[imidazolidine-4,2'-indane]-2,5-dione, which eluted second. MS: m/z 266 (M+1).

INTERMEDIATE 11

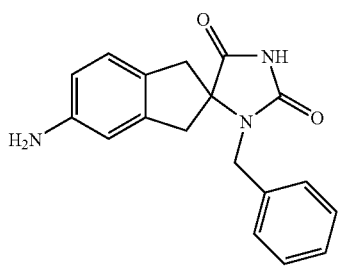

(±)-5'-Amino-3-(benzyl)-spiro[imidazolidine-4,2'-indane]-2,5-dione

Step A. (±)-1-(4-Methoxybenzyl)-5'-nitro-spiro[imidazolidine-4,2'-indane]-2,5-dione A mixture of (±)-5'-nitro-spiro[imidazolidine-4,2'-indane]-2,5-dione (1.4 g, 5.66 mmol, described in Intermediate 6), 4-methoxybenzyl alcohol (0.94 g, 6.80 mmol), diethyl azodicarboxylate (1.48 g, 8.49 mmol), and triphenylphosphine (2.23 g, 8.49 mmol) in THF (15 mL) was stirred at ambient temperature for 3 days. The solvent was removed under reduced pressure and the residue was partitioned between saturated aqueous NaHCO$_3$ (15 mL) and CH$_2$Cl$_2$ (50 mL). The organic layer was dried (Na$_2$SO$_4$), filtered, and concentrated under reduced pressure. The crude product was purified by silica gel chromatography, eluting with a gradient of hexane:EtOAc—90:10 to 60:40, to give the title compound. MS: m/z=368 (M+1).

Step B. (±)-3-Benzyl-1-(4-methoxybenzyl)-5'-nitro-spiro[imidazolidine-4,2'-indane]-2,5-dione To a solution of (±)-1-(4-methoxybenzyl)-5'-nitro-spiro[imidazolidine-4,2'-indane]-2,5-dione from Step A (165 mg, 0.45 mmol) in DMF (1 mL) was added sodium hydride (18 mg of a 60% dispersion in mineral oil, 0.45 mmol). The mixture was stirred for 5 min at ambient temperature and benzyl bromide (230 mg, 1.35 mmol) was added. After 30 min, the mixture was partitioned between saturated aqueous NaHCO$_3$ (3 mL) and CHCl$_3$ (5 mL). The aqueous phase was extracted further with CHCl$_3$ (5 mL) and the combined organic layers were dried (Na$_2$SO$_4$), filtered, and concentrated under reduced pressure. The crude product was purified by silica gel chromatography, eluting with hexane:EtOAc—75:25, to give the title compound. MS: m/z=458 (M+1).

Step C. (±)-3-Benzyl-5'-nitro-spiro[imidazolidine-4,2'-indane]-2,5-dione

To a stirred solution of (±)-3-benzyl-1-(4-methoxybenzyl)-5'-nitro-spiro[imidazolidine-4,2'-indane]-2,5-dione from Step B (110 mg, 0.24 mmol) in acetonitrile (1.5 mL) was added dropwise a solution of ammonium cerium (IV) nitrate (395 mg, 0.72 mmol) in H$_2$O (1 mL). After 3 h at ambient temperature, the precipitate was isolated by filtration and dried in vacuo to afford the title compound. MS: m/z=338 (M+1).

Step D. (±)-5'-Amino-3-benzyl-spiro[imidazolidine-4,2'-indane]-2,5-dione

To a solution of (±)-3-benzyl-5'-nitro-spiro[imidazolidine-4,2'-indane]-2,5-dione from Step C (80 mg, 0.24 mmol) in EtOAc (1.5 mL) and MeOH (1.5 mL) was added 10% Pd/C (5 mg) and the reaction mixture was stirred vigorously under hydrogen (ca. 1 atm). After 18 h, the catalyst was filtered off and the filtrate was concentrated to yield the title compound. MS: m/z=308 (M+1).

INTERMEDIATE 12

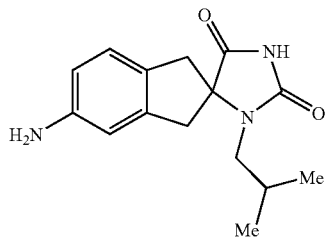

(±)-5'-Amino-3-(2-methylprop-1-yl)-spiro[imidazolidine-4,2'-indane]-2,5-dione

Essentially following the procedures described for Intermediate 11, but using 1-bromo-2-methylpropane in place of benzyl bromide, the title compound was prepared. MS: m/z 274 (M+1).

INTERMEDIATE 13

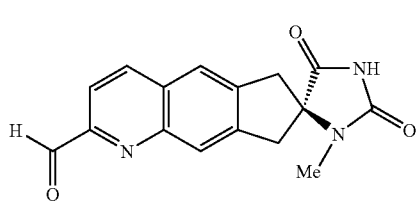

(7R)-3'-Methyl-2',5'-dioxo-6,8-dihydrospiro[cyclopenta[g]quinoline-7,4'-imidazolidine]-2-carbaldehyde Step A. (7R)-2,3'-Dimethyl-6,8-dihydro-2'H,5'H-spiro[cyclopenta[g]quinoline-7,4'-imidazolidine]-2',5'-dione (R)-5'-Amino-3-methyl-spiro[imidazolidine-4,2'-indane]-2,5-dione (3.00 g, 13.0 mmol, described in Intermediate 8) and p-chloranil (3.19 g, 13.0 mmol) were suspended in a mixture of 1-BuOH (3.2 mL) and conc. hydrochloric acid (3.2 mL, 39 mmol), and the mixture was heated to reflux. Crotonaldehyde (1.09 g, 15.6 mmol) in 1-BuOH (3 mL) was added dropwise over 20 min. After a further 20 min at reflux, the mixture was allowed to cool to ambient temperature, 10 N NaOH (3.9 mL, 39 mmol) was added, and the neutralized mixture was concentrated in vacuo to give a brown residue. The crude product was purified by silica gel chromatography, eluting with a gradient of CH$_2$Cl$_2$:MeOH—100:0 to 90:10, to give the title compound. MS: m/z=282 (M+1).

Step B. (7R)-3'-Methyl-2',5'-dioxo-6,8-dihydrospiro[cyclopenta[g]quinoline-7,4'-imidazolidine]-2-carbaldehyde A mixture of (7R)-2,3'-dimethyl-6,8-dihydro-2'H,5'H-spiro[cyclopenta[g]quinoline-7,4'-imidazolidine]-2',5'-dione from Step A (1.70 g, 6.04 mmol), selenium dioxide (1.01 g, 9.06 mmol) and powdered molecular sieves, 4 Å, (680 mg) in dioxane (60 mL) was heated at reflux for 90 min. The reaction mixture was filtered through a pad of Celite, washing with CH$_2$Cl$_2$-MeOH, and the filtrate was concentrated under reduced pressure. The residue was partitioned between saturated aqueous NaHCO$_3$ (400 mL) and EtOAc (1.5 L) containing MeOH (30 mL). The organic layer was extracted and the aqueous layer was washed with EtOAc (400 mL). The combined organic layers were washed with brine, dried over Na$_2$SO$_4$, filtered, and concentrated in vacuo to give the title compound. MS: m/z=296 (M+1).

INTERMEDIATE 14

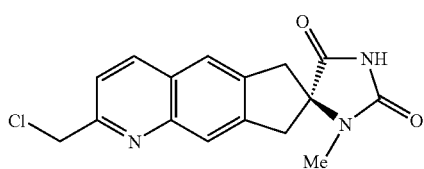

(7R)-2-(Chloromethyl)-3'-methyl-6,8-dihydro-2'H, 5'H-spiro[cyclopenta[g]quinoline-7,4'-imidazolidine]-2',5'-dione Step A. (7R)-2-(Hydroxymethyl)-3'-methyl-6,8-dihydro-2'H,5'H-spiro[cyclopenta[g]quinoline-7,4'-imidazolidine]-2',5'-dione To a stirred solution of (7R)-3'-methyl-2',5'-dioxo-6,8-dihydrospiro[cyclopenta[g]quinoline-7,4'-imidazolidine]-2-carbaldehyde (2.62 g, 8.89 mmol, described in Intermediate 13) in MeOH (20 mL) was added NaBH$_4$ (672 mg, 17.8 mmol) and the mixture was stirred at ambient temperature for 1 h, then concentrated to dryness in vacuo. The crude product was purified by silica gel chromatography, eluting with a gradient of CH$_2$Cl$_2$:MeOH:NOH—100:0:0 to 90:9:1, to give the title compound. MS: m/z=298 (M+1).

Step B. (7R)-2-(Chloromethyl)-3'-methyl-6,8-dihydro-2'H5'H-spiro[cyclopenta[g]quinoline-7,4'-imidazolidine]-2',5'-dione To a stirred solution of (7R)-2-(hydroxymethyl)-3'-methyl-6,8-dihydro-2'H,5'H-spiro[cyclopenta[g]quinoline-7,4'-imidazolidine]-2',5'-dione from Step A (200 mg, 0.67 mmol) in CH$_2$Cl$_2$ (5 mL) was added thionyl chloride (0.98 mL, 13.5 mmol) dropwise. The reaction mixture was stirred for 30 min and the precipitate was isolated by filtration. The filtrate was poured into saturated aqueous NaHCO$_3$ (20 mL) and this mixture was extracted with CH$_2$Cl$_2$ (3×30 mL). The combined organic extracts were dried over Na$_2$SO$_4$, filtered, and concentrated in vacuo to give a solid, which was combined with the filtered solid to give the title compound, which was of sufficient purity for use in subsequent steps. MS: m/z=316 (M+1).

INTERMEDIATE 15

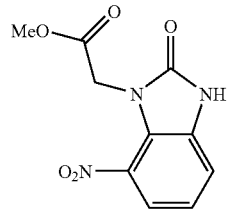

Methyl (7-nitro-2-oxo-2,3-dihydro-1H-benzimidazol-1-yl)acetate

Step A. Methyl N-(6-carboxy-2-nitrophenyl)glycinate

A mixture of methyl glycinate (15.9 g, 127 mmol), 2-chloro-3-nitrobenzoic acid (6.07 g, 30.1 mmol) and Na$_2$CO$_3$ (22.9 g, 216 mmol) in tert-BuOH (40 mL) was heated at reflux for 18 h. The cooled mixture was concentrated under reduced pressure and the residue was partitioned between H$_2$O (200 mL) and EtOAc (200 mL). The aqueous layer was acidified to pH 2 and the organic layer was extracted. The aqueous layer was extracted further with EtOAc (2×200 mL). The combined organic extracts were washed with brine, dried over Na$_2$SO$_4$, filtered, and concentrated in vacuo to give the title compound in sufficient purity for use in the next step. MS: m/z=255 (M+1).

Step B. Methyl (7-nitro-2-oxo-2,3-dihydro-1H-benzimidazol-1-yl)acetate

A mixture of methyl N-(6-carboxy-2-nitrophenyl)glycinate from Step A (6.08 g, 23.9 mmol), diphenyl phosphoryl azide (7.90 g, 28.7 mmol) and N,N-diisopropylethylamine (12.5 mL, 71.8 mmol) in tert-BuOH (40 mL) was heated at 90° C. for 90 min, then solvent was removed in vacuo. The residue was purified by silica gel chromatography, eluting with a gradient of CH$_2$Cl$_2$:MeOH—100:0 to 90:10, to give the title compound in sufficient purity for use in subsequent steps. MS: m/z=252 (M+1).

INTERMEDIATE 16

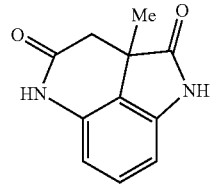

2a-Methyl-2a,5-dihydropyrrolo[4,3,2-de]quinoline-2,4(1H,3H)-dione, enantiomer B

Step A. 4-Nitro-1,3-dihydro-2H-indol-2-one

A mixture of 4-nitroindole (12.2 g, 75.2 mmol) and N-chlorosuccinimide (6.07 g, 30.1 mmol) in CHCl$_3$ (500 mL) was heated at reflux for 30 h, then concentrated under reduced pressure to give an orange solid. The solid was dissolved in AcOH (200 mL) and the resulting solution was warmed to 70° C., then 85% H$_3$PO$_4$ (80 mL) was added over 2 min. The mixture was heated to reflux for 90 min then cooled on ice.

The cooled mixture was adjusted to pH 6 by addition of 10 N NaOH (450 mL), followed by aqueous NaHCO$_3$, keeping the temperature below 30° C. The mixture was extracted with EtOAc (3×1 L) and the combined organic extracts were dried over Na$_2$SO$_4$, filtered, and concentrated in vacuo. The crude product was partially purified by silica gel chromatography, eluting with a gradient of hexane:EtOAc—100:0 to 0:100, and then triturated with MeOH to give the title compound. MS: m/z 179 (M+1).

Step B. (L)-Ethyl (3-methyl-4-nitro-2-oxo-2,3-dihydro-1H-indol-3-yl)acetate

To a stirred solution of 4-nitro-1,3-dihydro-2H-indol-2-one from Step A (6.95 g, 39.0 mmol) in DMF (180 mL) at 0° C. was added sodium hydride (60% dispersion in mineral oil; 1.72 g, 42.9 mmol) and the resulting mixture was stirred for 30 min. Iodomethane (2.43 mL, 39.0 mmol) in DMF (20 mL) was added dropwise over 20 min, and the mixture was stirred at 0° C. for 1 h. A further equivalent of sodium hydride (60% dispersion in mineral oil; 1.56 g, 39.0 mmol) was added and stirring was continued for 1 h. Ethyl bromoacetate (3.46 mL, 31.2 mmol) in DMF (20 mL) was added dropwise over 20 min. The reaction mixture was stirred at 0° C. for 1 h, then quenched with saturated aqueous NH$_4$Cl (500 mL). The mixture was extracted with EtOAc (3×500 mL) and the combined organic extracts were washed with brine (100 mL), then dried over Na$_2$SO$_4$, filtered, and concentrated in vacuo. The crude product was purified by silica gel chromatography, eluting with a gradient of hexane:EtOAc—100:0 to 0:100, to give the title compound. MS: m/z=279 (M+1).

Step C. (L)-Ethyl (4-amino-3-methyl-2-oxo-2,3-dihydro-1H-indol-3-yl)acetate

A mixture of (±)-ethyl (3-methyl-4-nitro-2-oxo-2,3-dihydro-1H-indol-3-yl)acetate from Step B (2.66 g, 9.56 mmol) and 10% Pd/C (500 mg) was stirred vigorously in MeOH (50 mL) under an atmosphere of hydrogen (ca. 1 atm). After 3 h, the mixture was filtered through a pad of Celite, washing with MeOH, and the filtrate was concentrated in vacuo to give the title compound. MS: m/z=249 (M+1).

Step D. 2a-Methyl-2a,5-dihydropyrrolo[4,3,2-de]quinoline-2,4(1H,3H)-dione, enantiomer B A mixture of (±)-ethyl (4-amino-3-methyl-2-oxo-2,3-dihydro-1H-indol-3-yl)acetate from Step C (2.37 g, 9.56 mmol) and AcOH (1 mL) was heated in xylenes (10 mL) at reflux for 24 h, then concentrated to dryness under reduced pressure. The crude product was partially purified by silica gel chromatography, eluting with a gradient of CH$_2$Cl$_2$:MeOH:NH$_4$H—100:0:0 to 90:9:1, to give a crude sample of the title compound. Further purification by silica gel chromatography, eluting with a gradient of CH$_2$Cl$_2$:EtOAc—100:0 to 0:100, gave the racemic title compound. The enantiomers were resolved by HPLC, utilizing a ChiralPak AS column and eluting with hexane:EtOH—70:30. The first major peak to elute was 2a-methyl-2a,5-dihydropyrrolo[4,3,2-de]quinoline-2,4(1H,3H)-dione, enantiomer A, and the second major peak to elute was 2a-methyl-2a,5-dihydropyrrolo[4,3,2-de]quinoline-2,4(1H,3H)-dione, enantiomer B, the title compound. MS: m/z=203 (M+1).

INTERMEDIATE 17

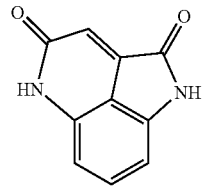

Pyrrolo[4,3,2-de]quinoline-2,4(1H,5H)-dione

Step A. (±)-Ethyl (4-nitro-2-oxo-2,3-dihydro-1H-indol-3-yl)acetate

To a stirred solution of 4-nitro-1,3-dihydro-2H-indol-2-one (3.00 g, 16.8 mmol, described in Intermediate 16) in DMF (100 mL) at 0° C. was added sodium hydride (60% dispersion in mineral oil; 740 mg, 18.5 mmol) and the resulting mixture was stirred for 30 min. Ethyl bromoacetate (1.87 mL, 16.8 mmol) in DMF (10 mL) was added dropwise over 10 min. The reaction mixture was stirred at 0° C. for 2 h, then quenched with H$_2$O (200 mL). The mixture was extracted with EtOAc (5×200 mL) and the combined organic extracts were washed with brine (100 mL), then dried over Na$_2$SO$_4$, filtered, and concentrated in vacuo. The crude product was purified by silica gel chromatography, eluting with a gradient of hexane:EtOAc—100:0 to 0:100, followed by crystallization from hexane:EtOAc to give the title compound. MS: m/z=265 (M+1).

Step B. (±)-Ethyl (4-amino-2-oxo-2,3-dihydro-1H-indol-3-yl)acetate

A mixture of (±)-ethyl (4-nitro-2-oxo-2,3-dihydro-1H-indol-3-yl)acetate from Step A (2.56 g, 9.69 mmol) and 10% Pd/C (500 mg) was stirred vigorously in MeOH (50 mL) under an atmosphere of hydrogen (ca. 1 atm). After 16 h, the mixture was filtered through a pad of Celite, washing with MeOH, and the filtrate was concentrated in vacuo to give the title compound. MS: m/z=235 (M+1).

Step C. (±)-2a,5-Dihydropyrrolo[4,3,2-de]quinoline-2,4(1H,3H)-dione

A mixture of (±)-ethyl (4-amino-2-oxo-2,3-dihydro-1H-indol-3-yl)acetate from Step B (2.40 g, 10.2 mmol), p-toluenesulfonic acid (195 mg, 1.03 mmol) and AcOH (1 mL) was heated in xylenes (10 mL) at reflux for 24 h, then concentrated to dryness under reduced pressure. The crude product was partially purified by silica gel chromatography, eluting with a gradient of CH$_2$Cl$_2$:MeOH:NH$_4$OH—100:0:0 to 90:9:1, to give a crude sample of the title compound. Further purification was achieved by trituration with CH$_2$Cl$_2$ to give the title compound. MS: m/z=189 (M+1).

Step D. Pyrrolo[4,3,2-de]quinoline-2,4(1H,5H)-dione

A mixture of (±)-2a,5-dihydropyrrolo[4,3,2-de]quinoline-2,4(1H,3H)-dione from Step C (200 mg, 1.06 mmol), and activated manganese (IV) oxide (185 mg, 2.13 mmol) was heated in toluene (3 mL) at 110° C. for 1 h. The mixture was filtered through a pad of Celite, washing with CH$_2$Cl$_2$:MeOH, and the filtrate was concentrated in vacuo to give the title compound. MS: m/z=187 (M+1).

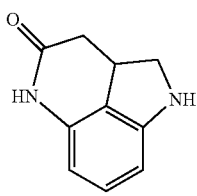

INTERMEDIATE 18

1,2,2a,5-Tetrahdropyrrolo[4,3,2-de]quinolin-4(3H)-one, enantiomer B

Step A. Ethyl(4-nitro-1H-indol-3 yl)(oxo)acetate

Diphosphoryl chloride (23.5 mL, 170 mmol) was added dropwise to a stirred mixture of 4-nitroindole (25.0 g, 154 mmol) and ethyl 1-piperidineglyoxylate (29.0 g, 170 mmol) at 0° C. The mixture was allowed to warm slowly to ambient temperature and stirring was continued for 18 h. The reaction mixture was cooled to 0° C. and quenched carefully by addition of EtOH (50 mL), followed by saturated aqueous NaBCO$_3$ until no further effervescence was observed. The precipitated yellow solid was isolated by filtration, washed with H$_2$O, and dried in vacuo to give the title compound. MS: m/z=263 (M+1).

Step B. Ethel (4-nitro-2,3-dihydro-1H-indol-3-yl)acetate enantiomer B

Triethylsilane (80 mL, 493 mmol) was added dropwise to a solution of ethyl (4-nitro-1H-indol-3-yl)(oxo)acetate from Step A (6.46 g, 24.6 mmol) in TFA (100 mL). After 3 h, the reaction mixture was concentrated in vacuo and the residue was purified by silica gel chromatography, eluting with a gradient of CH$_2$Cl$_2$:MeOH—100:0 to 99:1, to give the racemic product. The enantiomers were resolved by HPLC, utilizing a Chiralcel OD column and eluting with hexane:i-PrOH—70:30. The first major peak to elute was ethyl (4-nitro-2,3-dihydro-1H-indol-3-yl)acetate, enantiomer A, and the second major peak to elute was ethyl (4-nitro-2,3-dihydro-1H-indol-3-yl)acetate, enantiomer B, the title compound. MS: m/z=251 (M+1).

Step C. 1,2,2a,5-Tetrahydropyrrolo[4,3,2-de]quinolin-4(3H)-one, enantiomer B

To a stirred solution of ethyl (4-nitro-2,3-dihydro-1H-indol-3-yl)acetate, enantiomer B, from Step B (1.50 g, 5.99 mmol) in H$_2$O (50 mL) and EtOH (42 mL) was added sodium hydrosulfite (ca. 85%; 4.91 g, 24 mmol). The reaction mixture was stirred at ambient temperature for 1 h, then 3 N hydrochloric acid (14 mL, 42 mmol) was added and the solution was heated to 100° C. for 3 h. The cooled mixture was adjusted to pH 8 with saturated aqueous NaHCO$_3$, then extracted with CH$_2$Cl$_2$ (6×200 mL). The combined organic extracts were dried over Na$_2$SO$_4$, filtered, and concentrated in vacuo to give the title compound. MS: m/z=175 (M+1).

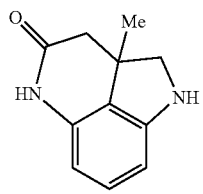

INTERMEDIATE 19

2a-Methyl-1,2,2a,5-tetrahydropyrrolo[4,3,2-de]quinolin-4(3H-one, enantiomer A

Step A. (±)-Ethyl(3-methyl-4-nitro-2-thioxo-2,3-dihydro-1H-indol-3-yl)acetate

A mixture of (±)-ethyl (3-methyl-4-nitro-2-oxo-2,3-dihydro-1H-indol-3-yl)acetate (1.08 g, 3.88 mmol, described in Intermediate 16) and Lawesson's reagent (942 mg, 2.33 mmol) was heated at reflux in xylenes (30 mL) for 90 min. The reaction mixture was concentrated in vacuo and the residue was purified by silica gel chromatography, eluting with a gradient of CH$_2$Cl$_2$:EtOAc—100:0 to 90:10, to give the title compound. MS: m/z=295 (M+1).

Step B. (±)-Ethyl (4-amino-3-methyl-2,3-dihydro-1H-indol-3-yl)acetate

To a solution of (±)-ethyl (3-methyl-4-nitro-2-thioxo-2,3-dihydro-1H-indol-3-yl)acetate from Step A (3.65 g, 12.4 mmol) and nickel (II) chloride hexahydrate (23.6 g, 99.2 mmol) in MeOH (30 mL) and THF (30 mL), at 0° C., was added NaBH$_4$ (11.3 g, 298 mmol) in portions over 1 h. The resulting mixture was stirred for 10 min, then filtered through a pad of Celite, washing with MeOH, and the filtrate was concentrated in vacuo. The residue was purified by silica gel chromatography, eluting with CH$_2$Cl$_2$:MeOH—90:10, to give the title compound. MS: m/z=235 (M+1).

Step C. 2a-Methyl-1,2,2a,5-tetrahydropyrrolo[4,3,2-de]quinolin-4(3H)-one, enantiomer A A mixture of (±)-ethyl (4-amino-3-methyl-2,3-dihydro-1H-indol-3-yl)acetate from Step B (2.50 g, 10.7 mmol) and p-toluenesulfonic acid (2 mg, 0.01 mmol) was heated in xylenes (50 mL) at reflux for 13 h, then concentrated to dryness under reduced pressure. The crude product was purified by silica gel chromatography, eluting with a gradient of CH$_2$Cl$_2$:MeOH:N$_4$OH—100:0:0 to 90:4.5:0.5, to give the racemic title compound. The enantiomers were resolved by HPLC, utilizing a ChiralPak AD column and eluting with hexane:i-PrOH:Et$_2$NH—75:25:0.1. The first major peak to elute was 2a-methyl-1,2,2a,5-tetrahydropyrrolo[4,3,2-de]quinolin-4(3H)-one, enantiomer A, the title compound, and the second major peak to elute was 2a-methyl-1,2,2a,5-tetrahydropyrrolo[4,3,2-de]quinolin-4(3H)-one, enantiomer B. MS: m/z=189 (M+1).

INTERMEDIATE 20

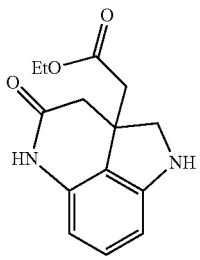

Ethyl (4-oxo-1,2,4,5-tetrahydropyrrolo[4,3,2-de]quinolin-2a (3H-yl)acetate, enantiomer A

Step A. Diethyl 2,2'-(4-nitro-2-oxo-2,3-dihydro-1H-indol-3,3-diyl)diacetate

To a stirred solution of 4-nitro-1,3-dihydro-2H-indol-2-one (5.25 g, 29.5 mmol, described in Intermediate 16) in DMF (200 mL) at 0° C. was added sodium hydride (60% dispersion in mineral oil; 1.24 g, 30.9 mmol) and the resulting mixture was stirred for 30 min. Ethyl bromoacetate (3.60 mL, 32.4 mmol) was added dropwise and the mixture was stirred at 0° C. for 1 h. A further equivalent of sodium hydride (60% dispersion in mineral oil; 1.24 g, 30.9 mmol) was added, stirring was continued for 1 h, then ethyl bromoacetate (3.00 mL, 27.1 mmol) was added dropwise. The reaction mixture was stirred for 1 h, then quenched with saturated aqueous NH$_4$Cl (125 mL) and H$_2$O (500 mL). The mixture was extracted with EtOAc (3×300 mL) and the combined organic extracts were washed with brine (100 mL), then dried over Na$_2$SO$_4$, filtered, and concentrated in vacuo. The crude product was purified by silica gel chromatography, eluting with a gradient of hexane:EtOAc—100:0 to 50:50, to give the title compound. MS: m/z=351 (M+1).

Ethyl (4-oxo-1,2,4,5-tetrahydropyrrolo[4,3,2-de]quinolin-2a(3H)-yl)acetate, enantiomer A Essentially following the procedures described for Intermediate 19, but using diethyl 2,2'-(4-nitro-2-oxo-2,3-dihydro-1H-indol-3,3-diyl)diacetate from Step A in place of (±)-ethyl (3-methyl-4-nitro-2-oxo-2,3-dihydro-1H-indol-3-yl)acetate, the racemic title compound was prepared. The enantiomers were resolved by HPLC, utilizing a ChiralPak AD column and eluting with hexane:EtOH:Et$_2$NH—75:25:0.1. The first major peak to elute was ethyl (4-oxo-1,2,4,5-tetrahydropyrrolo[4,3,2-de]quinolin-2a(3H)-yl)acetate, enantiomer A, the title compound, and the second major peak to elute was ethyl (4-oxo-1,2,4,5-tetrahydropyrrolo[4,3,2-de]quinolin-2a(3H)-yl)acetate, enantiomer B. MS: m/z=261 (M+1).

INTERMEDIATE 21

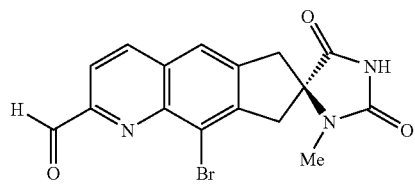

(7R)-9-Bromo-3'-methyl-2',5'-dioxo-6,8-dihydrospiro[cyclopenta[g]quinoline-7,4'-imidazolidine]-2-carbaldehyde

Step A. (7R)-9-Bromo-2,3'-dimethyl-6,8-dihydro-2'H5'H-spiro[cyclopenta[g]quinoline-7,4'-imidazolidine]-2',5'-dione To a stirred solution of (7R)-2,3'-dimethyl-6,8-dihydro-2'H,5'H-spiro[cyclopenta[g]quinoline-7,4'-imidazolidine]-2',5'-dione (250 mg, 0.89 mmol, described in Intermediate 13) in conc. sulfuric acid (1 mL) was added N-bromosuccinimide (206 mg, 1.16 mmol). The reaction mixture was stirred for 6 h, poured onto ice, neutralized with saturated aqueous NaHCO$_3$, and extracted with EtOAc (2×100 mL). The combined organic extracts were dried over Na$_2$SO$_4$, filtered, and concentrated in vacuo. The crude product was purified by HPLC, utilizing a Chiralcel OJ column and eluting with MeOH. The first major peak to elute was the title compound. MS: m/z=362 (M+1).

(7R)-9-Bromo-3'-methyl-2',5'-dioxo-6,8-dihydrospiro[cyclopenta[g]quinoline-7,4'-imidazolidine]-2-carbaldehyde Essentially following the procedures described for Intermediate 13, but using (7R)-9-bromo-2,3'-dimethyl-6,8-dihydro-2'H,5'H-spiro[cyclopenta[g]quinoline-7,4'-imidazolidine]-2',5'-dione from Step A in place of (7R)-2,3'-dimethyl-6,8-dihydro-2'H,5'H-spiro[cyclopenta[g]quinoline-7,4'-imidazolidine]-2',5'-dione, the title compound was prepared. MS: m/z=376 (M+1).

INTERMEDIATE 22

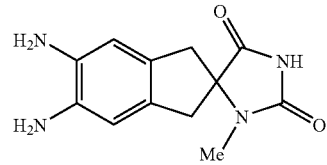

5'6'-Diamino-3-methyl-spiro[imidazolidine-4,2'-indane]-2,5-dione

Step A. (±)-5'-Amino-6'-nitro-3-methyl-spiro[imidazolidine-4,2'-indane]-2,5-dione To (±)-5'-amino-3-methyl-spiro[imidazolidine-4,2'-indane]-2,5-dione (100 mg, 0.432 mmol, described in Intermediate 7) at 0° C. were added 70% HNO$_3$ (1 mL) followed by conc. H$_2$SO$_4$ (1 mL). The resulting mixture was allowed to warm to ambient temperature and stirred for 18 h, then poured onto ice and the precipitate was removed by filtration. The aqueous filtrate was purified by HPLC using a reversed phase C18 column and eluting with a gradient of H$_2$O:CH$_3$CN:CF$_3$CO$_2$H—90:10:0.1 to 5:95:0.1. Lyophilization provided the title compound. MS: m/z=277 (M+1).

Step B. 5',6'-Diamino-3-methyl-spiro[imidazolidine-4,2'-indane]2,5-dione

To a solution of (±)-5'-amino-6'-nitro-spiro[imidazolidine-4,2'-indane]-2,5-dione from Step A (15 mg, 0.054 mmol) in MeOH (5 mL) was added 10% Pd/C (5 mg) and the reaction mixture was stirred vigorously under hydrogen (ca. 1 atm).

After 2 h, the catalyst was filtered off and the filtrate was concentrated in vacuo to yield the title compound. MS: m/z=247 (M+1).

INTERMEDIATE 23

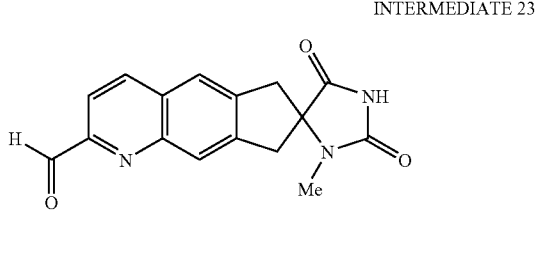

(±)-3'-Methyl-2',5'-dioxo-6,8-dihydrospiro[cyclopenta[g]quinoline-7,4'-imidazolidine]-2-carbaldehyde Essentially following the procedures described for Intermediate 13, but using (±)-5'-amino-3-methyl-spiro[imidazolidine-4,2'-indane]-2,5-dione (described in Intermediate 7) in place of (R)-5'-amino-3-methyl-spiro[imidazolidine-4,2'-indane]-2,5-dione, the title compound is prepared.

INTERMEDIATE 24

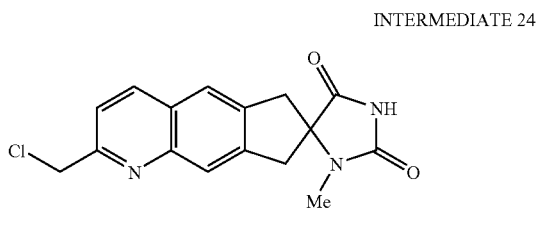

(±)-2-(Chloromethyl)-3'-methyl-6,8-dihydro-2'H,5'H-spiro[cyclopenta[g]quinoline-7,4'-imidazolidine]-2',5'-dione Essentially following the procedures described for Intermediate 14, but using (±)-3'-methyl-2',5'-dioxo-6,8-dihydrospiro[cyclopenta[g]quinoline-7,4'-imidazolidine]-2-carbaldehyde (described in Intermediate 23) in place of (7R)-3'-methyl-2',5'-dioxo-6,8-dihydrospiro[cyclopenta[g]quinoline-7,4'-imidazolidine]-2-carbaldehyde, the title compound is prepared.

INTERMEDIATE 25

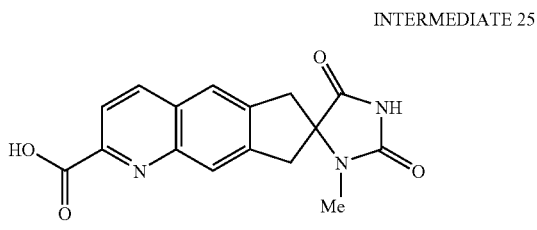

(±)-3'-Methyl-2',5'-dioxo-6,8-dihydrospiro[cyclopenta[g]quinoline-7,4'-imidazolidine]-2-carboxylic acid A mixture of (±)-2,3'-dimethyl-6,8-dihydro-2'H,5'H-spiro[cyclopenta[g]quinoline-7,4'-imidazolidine]-2',5'-dione (500 mg, 1.78 mmol, described in Intermediate 23) and selenium dioxide (592 mg, 5.33 mmol) in dioxane (30 mL) and $H_2O$ (3 mL) are heated at reflux for 18 h. The reaction mixture is allowed to cool, filtered through a pad of Celite, and the filtrate is concentrated in vacuo to give the title compound.

INTERMEDIATE 26

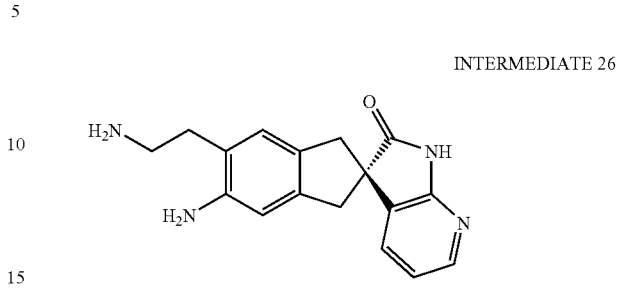

(2S)-5-Amino-6-(2-aminoethyl)-1,3-dihydrospiro[indene-2,3'-pyrrolo[2,3-b]pyridin]-2'(1'H)-one Step A. 1-{[2-Trimethylsilyl)ethoxy]methyl}-1H-pyrrolo[2,3-b]pyridine Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with $H_2O$ (500 mL) and the mixture was extracted with $CH_2Cl_2$ (5×300 mL). The combined organic layers were washed with brine, dried over $MgSO_4$, filtered, concentrated and dried under high vacuum to give the title compound. MS: m/z=249 (M+1).

Step B. 3,3-Dibromo-1-{[2-(trimethyl silyl)ethoxy]methyl}-1,3-dihydro-2H-pyrrolo[2,3-h]pyridin-2-one A solution of 1-{[2-(trimethylsilyl)ethoxy]methyl}-1H-pyrrolo[2,3-b]pyridine from Step A (43.1 g, 0.174 mol) in dioxane (300 mL) was added dropwise over 30 min to a suspension of pyridine hydrobromide perbromide (277 g, 0.868 mol) in dioxane (300 mL). The reaction was stirred at ambient temperature using an overhead mechanical stirrer. After 60 min, the biphasic reaction mixture was quenched with $H_2O$ (300 mL) and extracted with EtOAc. The aqueous layer was washed with EtOAc (2×300 mL) and the combined organic layers were washed with $H_2O$ (4×300 mL; the final wash was pH 5-6), then brine (300 mL), then dried over $MgSO_4$, filtered and concentrated under reduced pressure. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one from Step B (65 g, 0.154 mol) in THF (880 mL) and saturated aqueous ammonium chloride (220 mL). After 3 h, the reaction was filtered and concentrated in vacuo. The residue was partitioned between EtOAc and H₂O which resulted in the formation of a white precipitate. Both layers were filtered through a Celite pad and the layers were separated. The aqueous layer was washed with EtOAc (2×) and the combined organic layers were washed with H₂O, dried over MgSO₄, filtered, and concentrated. The crude product was filtered through a plug of silica gel eluting with EtOAc:CH₂Cl₂—1:9 and the eluant was concentrated under reduced pressure to provide the title compound. MS: m/z=265 (M+1).

Step D. (4-Nitro-1,2-phenylene)dimethanol

4-Nitrophthalic acid (40 g, 189.5 mmol) in tetrahydrofuran (500 mL) was added dropwise over 1.5 h to a solution of borane-THF complex (1 M, 490 mL, 490 mmol), keeping the reaction temperature between 0° C. and 5° C. After the addition, the reaction was allowed to warm slowly to ambient temperature and stirred for 18 h. Methanol (100 mL) was added carefully and the precipitated solid dissolved. The mixture was concentrated in vacuo to about 500 mL, cooled to 0° C., and 10 N sodium hydroxide was added to adjust the pH to 10-11. This mixture was extracted with EtOAc (3×600 mL) and the combined organic layers were washed with brine, dried over Na₂SO₄, filtered, and concentrated in vacuo to give the title compound. MS: m/z=207 (M−OH+CH₃CN).

Step E. 1,2-Bis(bromomethyl)-4-nitrobenzene

Phosphorus tribromide (3.9 mL, 41.1 mmol) in ether (50 mL) was added dropwise over 1.5 h to a solution of (4-nitro-1,2-phenylene)dimethanol from Step D (6.85 g, 37.4 mmol) in ether (150 mL). After 18 h, the reaction mixture was cooled to 0° C. and quenched with H₂O (25 mL). The layers were separated and the organic layer was washed with H₂O, then saturated aqueous NaHCO₃, dried over Na₂SO₄, filtered, and concentrated in vacuo to give the title compound as a pale solid. MS: m/z=309 (M+1).

Step F. (±)-5-Nitro-1'-{[2-(trimethylsilyl)ethoxy]methyl}-1,3-dihydrospiro[indene-2,3'-pyrrolo[2,3-b]pyridin]-2'(1'H)-one To a solution of 1,2-bis(bromomethyl)-4-nitrobenzene from Step E (40.9 g, 132 mmol) and 1-{[2-(trimethylsilyl)ethoxy]methyl}-1,3-dihydro-2H-pyrrolo[2,3-b]pyridin-2-one from Step C (31.5 g, 119 mmol) in DMF (2 L) was added cesium carbonate (129 g, 397 mmol), portionwise, over 5 min. After 18 h, acetic acid (7.6 mL) was added and the mixture was concentrated to a volume of about 500 mL, then partitioned between EtOAc (1.5 L) and H₂O (1 L). The organic layer was washed with H₂O (1 L), then brine (500 mL), then dried over Na₂SO₄, filtered, and concentrated in vacuo. The crude product was purified by silica gel chromatography, eluting with a gradient of hexane:EtOAc—100:0 to 0:100, to give the title compound. MS: m/z=412 (M+1).

Step G. (R)-5-Amino-1'-{[2-(trimethylsilyl)ethoxy]methyl}-1,3-dihydrospiro[indene-2,3'-pyrrolo[2,3-b]pyridin]-2'(1'H)-one A mixture of 10% Pd/C (3 g) and (±)-5-nitro-1'-{[2-(trimethylsilyl)ethoxy]methyl}-1,3-dihydrospiro[indene-2,3'-pyrrolo[2,3-b]pyridin]-2'(1'H)-one from Step F (19.1 g, 46.4 mmol) was stirred vigorously in EtOH (400 mL) under an atmosphere of hydrogen (ca. 1 atm). After 18 h, the mixture was filtered through a pad of Celite, washing extensively with MeOH, and the filtrate was concentrated in vacuo to give the crude racemic compound. The enantiomers were resolved by HPLC, utilizing a Chiralcel OD column and eluting with MeOH. The first major peak to elute was (S)-5-amino-1'-{[2-(trimethylsilyl)ethoxy]methyl}-1,3-dihydrospiro[indene-2,3'-pyrrolo[2,3-b]pyridin]-2'(1')-one, and the second major peak to elute was (R)-5-amino-1'-{[2-(trimethylsilyl)ethoxy]methyl}-1,3-dihydrospiro[indene-2,3'-pyrrolo[2,3-b]pyridin]-2'(1'H)-one, the title compound. MS: m/z=382 (M+1).

Step H. (S)-5-Amino-6-nitro-1,3-dihydrospiro[indene-2,3')pyrrolo[2,3-b]pyridin]-2'(1'H)-one To a suspension of (R)-5-amino-1'-{[2-(trimethylsilyl)ethoxy]methyl}-1,3-dihydrospiro[indene-2,3'-pyrrolo[2,3-b]pyridin]-2'(1'H)-one from Step G (28.7 g, 75.2 mmol) in CH₂Cl₂ (100 mL) was added trifluoroacetic anhydride (106 mL, 752 mmol). The mixture was stirred for 10 min, after which time the aniline had been converted to the corresponding trifluoroacetanilide. The resulting mixture was cooled in an ice-salt bath and 15.8 M nitric acid (5.0 mL, 79 mmol) was added dropwise over 15 min, keeping the reaction temperature at 10-12° C. After the addition, the reaction mixture was stirred for 30 min, then H₂O (12 mL) was carefully added, followed by trifluoroacetic acid (100 mL) and CH₂Cl₂ (100 mL). The mixture was allowed to warm to ambient temperature and stirring was continued for 2 h, followed by concentration to dryness in vacuo. The residue was dissolved in MeOH (200 mL) and the solution was adjusted to pH 10 by addition of 10 N NaOH. Ethylene diamine (5 mL, 75 mmol) was added and the mixture was stirred at ambient temperature for 18 h, then diluted with H₂O (200 mL). The resulting solid was isolated by filtration, washed with H₂O, and dried in vacuo to give the title compound. MS: m/z=297 (M+1).

Step I. (2R)-5-Iodo-6-nitro-1,3-dihydrospiro[indene-2,3'-pyrrolo[2,3-b]pyridin]-2'(1'H)-one To a suspension of (S)-5-amino-6-nitro-1,3-dihydrospiro[indene-2,3'-pyrrolo[2,3-b]pyridin]-2'(1'H)-one from Step H (6.14 g, 20.7 mmol) in 3 N hydrochloric acid (50 mL) and THF (20 mL), at −5° C., was added NaNO₂ (1.60 g, 23.2 mmol) in H₂O (10 mL) dropwise at such a rate that the reaction temperature was maintained below 0° C. After a further 15 min, KI (9.2 g, 55 mmol) in H₂O (9 mL) was added dropwise over 30 min, keeping the reaction temperature below 0° C. After a further 15 min, the mixture was extracted with CH₂Cl₂ (3×300 mL), and the combined organic layers were dried over Na₂SO₄, decanted, and concentrated in vacuo. The crude product was purified by silica gel chromatography, eluting with a gradient of CH₂Cl₂:MeOH—100:0 to 90:10, to give the title compound, which was of sufficient purity for use in the next step. MS: m/z=408 (M+1).

Step J. (2R)-5-Iodo-6-nitro-1'-{[2-(trimethylsilyl)ethoxy]methyl}-1,3-dihydrospiro[indene-2,3'-pyrrolo[2,3-b]pyridin]-2'(1'H)-one Sodium hydride (60% dispersion in mineral oil; 525 mg, 13.1 mmol) was added to a solution of (2R)-5-iodo-6-nitro-1,3-dihydrospiro[indene-2,3'-pyrrolo[2,3-b]pyridin]-2'(1'H)-one from Step I (5.14 g, 12.6 mmol) in DMF (40 mL) at 0° C. and the mixture was stirred for 5 min. 2-(Trimethylsilyl)ethoxymethyl chloride (2.23 mL, 12.6 mmol) was then added dropwise, and the reaction mixture was stirred at 0° C. for 2 h. The reaction was quenched with dilute aqueous NaHCO₃ (200 mL) and the mixture was extracted with EtOAc (3×200 mL). The combined organic layers were washed with brine, dried over MgSO$_4$, filtered, and concentrated under reduced pressure. The crude product was purified by silica gel chromatography, eluting with a gradient of hexane:EtOAc—100:0 to 0:100, to give the title compound, which was of sufficient purity for use in the next step. MS: m/z=538 (M+1).

Step K. tert-Butyl((2S)-6-nitro-2'-oxo-1'-{[2-(trimethylsilyl)ethoxy]methyl}-1,1',2',3-tetrahydrospiro[indene-2,3'-pyrrolo[2,3-b]pyridin]-5-yl)acetate To a flask containing (2R)-5-iodo-6-nitro-1'-{[2-(trimethylsilyl)ethoxy]methyl}-1,3-dihydrospiro[indene-2,3'-pyrrolo[2,3-b]pyridin]-2'(1'H)-one from Step J (4.02 g, 7.48 mmol), tris(dibenzylideneacetone)dipalladium (349 mg, 0.38 mmol), and 1,2,3,4,5-pentaphenyl-1'-(di-tert-butylphosphino)ferrocene (532 mg, 0.75 mmol) was added 2-tert-butoxy-2-oxoethylzinc chloride (Rieke, 0.5 M in Et$_2$O; 15.7 mL, 7.85 mmol) and the resulting solution was heated to 40° C. for 1 h. The reaction was quenched with dilute aqueous NaHCO$_3$ (100 mL) and the mixture was extracted with EtOAc (200 mL). The organic layer was washed with brine, dried over Na$_2$SO$_4$, filtered, and concentrated under reduced pressure. The crude product was purified by silica gel chromatography, eluting with a gradient of hexane:EtOAc—100:0 to 0:100, to give the title compound, which was of sufficient purity for use in the next step. MS: m/z=526 (M+1).

Step L. [(2S)-6-Nitro-2'-oxo-1,1',2',3-tetrahydrospiro[indene-2,3'-pyrrolo[2,3-b]pyridin]-5-yl]acetic acid A solution of tert-butyl((2S)-6-nitro-2'-oxo-1'-{[2-(trimethylsilyl)ethoxy]methyl}-1,1',2',3-tetrahydrospiro[indene-2,3'-pyrrolo[2,3-b]pyridin]-5-yl)acetate from Step K (2.01 g, 3.83 mmol) in MeOH (25 mL) was saturated with HCl (g) and stood at ambient temperature for 18 h. The mixture was concentrated to dryness in vacuo, then redissolved in MeOH (25 mL). This stirred solution was adjusted to pH 10 with 10 N NaOH and ethylene diamine (0.26 mL, 3.83 mmol) was added. The resulting mixture was stirred for 3 h, then concentrated to dryness in vacuo. The residue was dissolved in THF (25 mL) and 1 N NaOH (25 mL, 25 mmol) was added. The mixture was stirred at ambient temperature for 18 h, then the THF was removed under reduced pressure. The residual mixture was partitioned between saturated aqueous NaHCO$_3$ (50 mL) and EtOAc (100 mL). The organic layer was discarded and the aqueous layer was adjusted to pH 2 with aqueous HCl, then extracted with EtOAc (3×200 mL). The combined organic layers were dried over Na$_2$SO$_4$, filtered, and concentrated under reduced pressure to give the title compound. MS: m/z=340 (M+1).

Step M. (21)-5-(2-Hydroxyethyl)-6-nitro-1,3-dihydrospiro[indene-2,3'-pyrrolo[2,3-b]pyridin]-2'(1)-one To a stirred solution of [(2S)-6-nitro-2'-oxo-1,1',2',3-tetrahydrospiro[indene-2,3'-pyrrolo[2,3-b]pyridin]-5-yl]acetic acid from Step L (753 mg, 2.22 mmol) in THF (15 mL), at −78° C., was added borane (1 M in TH; 9.1 mL, 9.1 mmol) dropwise. After 5 min, the mixture was warmed to 0° C. and stirring was continued at this temperature for 3 h. The reaction was quenched carefully with 1 N HCl and stirring was continued at ambient temperature. The mixture was adjusted to pH 8 with saturated aqueous NaHCO$_3$ and extracted with EtOAc (2×100 mL). The combined organic layers were dried over Na$_2$SO$_4$, filtered, and concentrated under reduced pressure. The crude product was purified by silica gel chromatography, eluting with a gradient of CH$_2$Cl$_2$:MeOH—100:0 to 80:20, to give the title compound. MS: m/z=326 (M+1).

Step N. (2S)-5-(2-Azidoethyl)-6-nitro-1,3-dihydrospiro[indene-23'-pyrrolo[2,3'-b]pyridin]-2'(1'H)-one To a stirred solution of (2S)-5-(2-hydroxyethyl)-6-nitro-1,3-dihydrospiro[indene-2,3'-pyrrolo[2,3-b]pyridin]-2'(1'H)-one from Step M (174 mg, 0.54 mmol) in DMF (4 mL) were added diphenyl phosphoryl azide (177 mg, 0.64 mmol) and DBU (0.096 mL, 0.64 mmol). The mixture was heated at 100° C. for 6 h, then quenched with H$_2$O (20 mL) and extracted with EtOAc (50 mL). The organic layer was dried over Na$_2$SO$_4$, filtered, and concentrated under reduced pressure. The crude product was purified by silica gel chromatography, eluting with a gradient of CH$_2$Cl$_2$:MeOH—100:0 to 80:20, to give the title compound. MS: m/z=351 (M−1).

Step O. (2S)-5-Amino-6-(2-aminoethyl)-1,3-dihydrospiro[indene-2,3'-pyrrolo[2,3-b]pyridin]-2'(1'H)-one To a solution of (2S)-5-(2-azidoethyl)-6-nitro-1,3-dihydrospiro[indene-2,3'-pyrrolo[2,3-b]pyridin]-2'(1H)-one from Step N (236 mg, 0.67 mmol) in EtOH (15 mL) was added 10% Pd/C (172 mg). The reaction mixture was stirred under a hydrogen atmosphere (ca. 1 atm) for 5 h, then filtered through a Celite pad, washing with MeOH, and the filtrate was concentrated under reduced pressure to give the title compound. MS: m/z=295 (M+1).

INTERMEDIATE 27

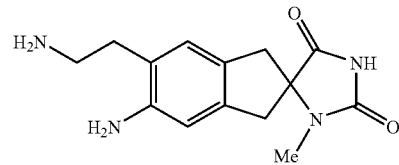

(±)-5'-Amino-6'-(2-aminoethyl)-3-methyl-1',3'-dihydro-2H,5H-spiro[imidazolidine-4,2'-indene]-2,5-dione Essentially following the procedures described for Intermediate 26, but using (±)-5'-amino-6'-nitro-spiro[imidazolidine-4,2'-indane]-2,5-dione (described in Intermediate 22) in place of (S)-5-amino-6-nitro-1,3-dihydrospiro[indene-2,3'-pyrrolo[2,3-b]pyridin]-2'(1'H)-one, the title compound is prepared.

INTERMEDIATE 28

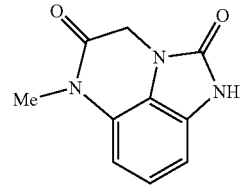

6-Methyl-4H-imidazo[1,5,4-de]quinoxaline-2,5(1H,6H-dione

Step A. N-(2-Amino-3-nitrophenyl)-4-methylbenzenesulfonamide

A stirred mixture of 3-nitro-1,2-phenylenediamine (1.00 g, 6.53 mmol) and p-toluenesulfonyl chloride (1.25 g, 6.53 mmol) in pyridine (50 ml) was heated at reflux for 1 h, then concentrated to dryness in vacuo to give the title compound in sufficient purity for use in the next step. MS: m/z=308 (M+1).

Step B. 1-[(4-Methylphenyl)sulfonyl]-4-nitro-1,3-dihydro-2H-benzimidazol-2-one To a stirred solution of N-(2-amino-3-nitrophenyl)-4-methylbenzenesulfonamide from Step A (2.00 g, 6.51 mmol) in $CH_3CN$ (100 mL) was added triphosgene (966 mg, 3.25 mmol) and the mixture was stirred at ambient temperature for 30 min. The precipitate was isolated by filtration and dried in vacuo to give the title compound. MS: m/z=334 (M+1).

Step C. Methyl {3-[(4-methylphenyl)sulfonyl]-7-nitro-2-oxo-2,3-dihydro-1H-benzimidazol-1-yl}acetate To a stirred solution of 1-[(4-methylphenyl)sulfonyl]-4-nitro-1,3-dihydro-2H-benzimidazol-2-one from Step B (500 mg, 1.50 mmol) in DMF (50 mL) was added potassium carbonate (207 mg, 1.50 mmol) and the resulting mixture was stirred at ambient temperature for 10 min. Methyl bromoacetate (252 mg, 1.65 mmol) was added dropwise and the reaction mixture was stirred for 1 h, then poured into $H_2O$ (50 mL). The resulting precipitate was isolated by filtration, washed with $H_2O$, and dried in vacuo to give the title compound. MS: m/z=406 (M+1).

Step D. 1-[(4-Methylphenyl)sulfonyl]-4H-imidazo[1,5,4-de]quinoxaline-2,5(1H,6H)-dione A mixture of methyl {3-[(4-methylphenyl)sulfonyl]-7-nitro-2-oxo-2,3-dihydro-1H-benzimidazol-1-yl}acetate from Step C (1.00 g, 2.47 mmol) and 10% Pd/C (100 mg) was stirred vigorously in EtOAc (100 mL) under an atmosphere of hydrogen (ca. 1 atm). After 4 h, the mixture was filtered through a pad of Celite, washing with EtOAc (300 mL). To the filtrate was added AcOH (2 mL) and this solution was heated at 80° C. for 1 h, then concentrated in vacuo to give the title compound. MS: m/z=344 (M+1).

Step E. 1-[(4-Methylphenyl)sulfonyl]-6-methyl-4H-imidazo[1,5,4-de]quinoxaline-2,5(1H,6H-dione To a stirred solution of 1-[(4-methylphenyl)sulfonyl]-4H-imidazo[1,5,4-de]quinoxaline-2,5(1H,6H)-dione from Step D (1.16 g, 3.38 mmol) in DMF (40 mL) was added potassium carbonate (467 mg, 3.38 mmol) and the resulting mixture was stirred at ambient temperature for 10 min. Iodomethane (480 mg, 3.38 mmol) was added dropwise and the reaction mixture was stirred for 18 h, then poured into $H_2O$ (50 mL). The resulting precipitate was isolated by filtration, washed with $H_2O$, and dried in vacuo to give the title compound. MS: m/z=358 (M+1).

Step F. 6-Methyl-4H-imidazo[1,5,4-de]quinoxaline-2,5(1H,6H)-dione

A solution of 1-[(4-methylphenyl)sulfonyl]-6-methyl-4H-imidazo[1,5,4-de]quinoxaline-2,5(1H,6H)-dione (600 mg, 1.68 mmol) in conc. $H_2SO_4$ (3 mL) was heated at 50° C. for 30 min, then poured into $H_2O$ at 0° C. (25 mL). The resulting precipitate was isolated by filtration, washed with $H_2O$, and dried in vacuo to give the title compound. MS: m/z=204 (M+1).

INTERMEDIATE 29

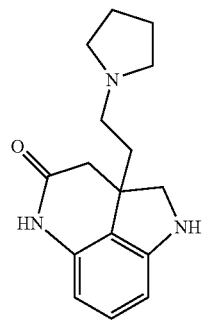

2a-(2-Pyrrolidin-1-ylethyl)-1,2,2a,5-tetrahydropyrrolo[4,3,2-de]quinolin-4(3H)-one, enantiomer A

Step A. tert-Butyl 2a-(2-ethoxy-2-oxoethyl)-4-oxo-2a,3,4,5-tetrahydropyrrolo[4,3,2-de]quinolin-1(2H)-carboxylate, enantiomer A To a stirred solution of ethyl (4-oxo-1,2,4,5-tetrahydropyrrolo[4,3,2-de]quinolin-2a(3H)-yl)acetate, enantiomer A, (158 mg, 0.607 mmol, described in Intermediate 20) and triethylamine (0.127 mL, 0.91 mmol) in $CH_2Cl_2$ (5 mL) was added di-tert-butyl dicarbonate (199 mg, 0.91 mmol). The mixture was stirred at ambient temperature for 19 h, then additional di-tert-butyl dicarbonate (100 mg, 0.46 mmol) and triethylamine (0.060 mL, 0.43 mmol) were added and stirring was continued for 72 h. The reaction mixture was quenched with saturated aqueous $NaHCO_3$ (10 mL) and extracted with $CH_2Cl_2$ (3×20 mL). The combined organic extracts were dried over $Na_2SO_4$, filtered, and concentrated in vacuo to give the title compound in sufficient purity for use in the next step. MS: m/z=305 (M—$C_4H_7$).

Step B. tert-Butyl 4-oxo-2a-(2-oxoethyl)-2a,3,4,5-tetrahydropyrrolo[4,3,2-de]quinolin-1(2H)-carboxylate, enantiomer A To a stirred solution of tert-butyl 2a-(2-ethoxy-2-oxoethyl)-4-oxo-2a,3,4,5-tetrahydropyrrolo[4,3,2-de]quinolin-1(2H)-carboxylate, enantiomer A, from Step A (219 mg, 0.607 mmol) in $CH_2Cl_2$ (5 mL) at −78° C. was added DIBAL-H (1 M in $CH_2Cl_2$, 0.8 mL, 0.8 mmol) dropwise. After 1 h, DIBAL-H (1 M in $CH_2Cl_2$, 0.54 mL, 0.54 mmol) was added dropwise, and after an additional 1 h, more DIBAL-H (1 M in $CH_2Cl_2$, 0.65 mL, 0.65 mmol) was added dropwise. The mixture was stirred at −78° C. for 1 h, then quenched by addition of cold MeOH (1 mL), then acetone (1 mL), then saturated aqueous potassium sodium tartrate (10 mL). The mixture was allowed to warm to ambient temperature and was extracted with $CH_2Cl_2$ (3×20 mL). The combined organic extracts were washed with brine (10 mL), dried over $Na_2SO_4$, filtered, and concentrated in vacuo to give the title compound in sufficient purity for use in the next step. MS: m/z=317 (M+1).

Step C. 2a-(2-Pyrrolidin-1-ylethyl)-1,2,2a,5-tetrahydropyrrolo[4,3,2-de]quinolin-4(3H)-one, enantiomer A To a stirred solution of tert-butyl 4-oxo-2a-(2-oxoethyl)-2a,3,4,5-tetrahydropyrrolo[4,3,2-de]quinolin-1(2H)-carboxylate, enantiomer A, from Step B (100 mg, 0.316 mmol), pyrrolidine (67 mg, 0.948 mmol), and AcOH (0.09 mL, 1.58 mmol) in DCE (1 mL) was added sodium triacetoxyborohydride (80 mg, 0.38 mmol) and the mixture was stirred for 18 h. To the resulting mixture was added TFA (1 mL) and stirring was continued for 4 h. The mixture was concentrated in vacuo and purified by HPLC using a reversed phase C18 column and eluting with a gradient of $H_2O:CH_3CN:CF_3CO_2H$—90:10:0.1 to 5:95:0.1. Lyophilization provided the title compound as the trifluoroacetate salt. MS: m/z=272 (M+1).

INTERMEDIATE 30

2a-Ethyl-1,2,2a,5-tetrahydropyrrolo[4,3,2-de]quinolin-4(3H)-one, enantiomer B

Step A. (±)-Ethyl (3-ethyl-4-nitro-2-oxo-2,3-dihydro-1H-indol-3-yl)acetate

Essentially following the procedures described for Intermediate 16, but using iodoethane in place of iodomethane, the title compound was prepared. MS: m/z=293 (M+1).

2a-Ethyl-1,2,2a,5-tetrahydropyrrolo[4,3,2-de]quinolin-4(3)-one, enantiomer B

Essentially following the procedures described for Intermediate 19, but using (±)-ethyl (3-ethyl-4-nitro-2-oxo-2,3-dihydro-1H-indol-3-yl)acetate in place of (±)-ethyl (3-methyl-4-nitro-2-oxo-2,3-dihydro-1H-indol-3-yl)acetate, the racemic title compound was prepared. The enantiomers were resolved by HPLC, utilizing a ChiralPak AS column and eluting with hexane:EtOH:$Et_2NH$—20:80:0.1. The first major peak to elute was 2a-ethyl-1,2,2a,5-tetrahydropyrrolo[4,3,2-de]quinolin-4(3H)-one, enantiomer A, and the second major peak to elute was 2a-ethyl-1,2,2a,5-tetrahydropyrrolo[4,3,2-de]quinolin-4(3H)-one, enantiomer B, the title compound. MS: m/z=203 (M+1).

INTERMEDIATE 31

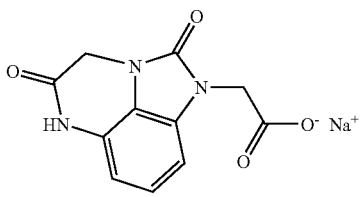

Sodium (2,5-dioxo-5,6-dihydro-4H-imidazo[1,5,4-de]quinoxalin-1 (2R)-yl)acetate

Step A. 4-Nitro-1,3-dihydro-2H-benzimidazol-2-one

Triphosgene (56 g, 188.8 mol) was added portionwise over 15 min to a solution of 3-nitro-1,2-phenylenediamine (25.5 g, 167 mol) in $CH_3CN$ (400 mL) at 0° C. and the mixture was allowed to warm to ambient temperature after 30 min. The reaction was concentrated in vacuo, diluted with toluene (100 mL) and the solid precipitate was collected by filtration to give the title compound. MS: m/z=180 (M+1).

Step B. Dimethyl 2,2'-(4-nitro-2-oxo-1H-benzimidazole-1,3-diyl)diacetate

Cesium carbonate (3.6 g, 11.1 mmol) was added to a solution of 4-nitro-1,3-dihydro-2H-benzimidazol-2-one from Step A (990 mg, 5.5 mmol) and methyl bromoacetate (1.05 mL, 11.1 mmol) in DMF (25 mL). After 1.5 h, the reaction was quenched with $H_2O$ and the solid precipitate was collected by filtration to give the title compound. MS: m/z=324 (M+1).

Step C. Methyl (2,5-dioxo-5,6-dihydro-4H-imidazo[1,5,4-de]quinoxalin-1(2H)-yl)acetate A mixture of dimethyl 2,2'-(4-nitro-2-oxo-1H-benzimidazole-1,3-diyl)diacetate from Step B (270 mg, 0.84 mmol) and 10% Pd/C (50 mg) in MeOH (10 mL) was stirred under an atmosphere of hydrogen (ca. 1 atm). After 2 h, the reaction was filtered through a Celite pad and concentrated in vacuo. The crude solid was dissolved in toluene (3 mL) and p-toluenesulfonic acid monohydrate (2 mg, 0.011 mmol) was added. The mixture was heated at reflux for 30 min and then concentrated in vacuo to give the title compound. MS: m/z=262 (M+1).

Step D. Sodium (2,5-dioxo-5,6-dihydro-4H-imidazo[1,5,4-de]quinoxalin-1(2H)-yl)acetate To a solution of methyl (2,5-dioxo-5,6-dihydro-4H-imidazo[1,5,4-de]quinoxalin-1(2H)-yl)acetate from Step C (367 mg, 1.40 mmol) in MeOH (40 mL) and $CH_3CN$ (5 mL) was added 1.0 N sodium hydroxide (2.82 mL, 2.82 mmol) and the reaction mixture was stirred at ambient temperature for 18 h. The mixture was neutralized with 1 N aqueous HCl and concentrated in vacuo to give the title compound. MS: m/z=248 (M+1).

INTERMEDIATE 32

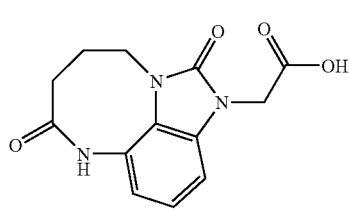

(2,7-Dioxo-5,6,7,8-tetrahydro-4H-imidazo[1,5,4-fg][1,6]benzodiazocin-1(2H)-yl)acetic acid Step A. tert-Butyl (4-nitro-2-oxo-2,3-dihydro-1H-benzimidazol-1-yl)acetate Cesium carbonate (1.75 g, 5.4 mmol) was added to a solution of 4-nitro-1,3-dihydro-2H-benzimidazol-2-one (800 mg, 4.5 mmol, described in Intermediate 31) and tert-butyl bromoacetate (0.791 mL, 5.4 mmol) in DMF (15 mL). After 18 h, the reaction was quenched with H₂O (100 mL) and the solid precipitate was collected by filtration. The crude product was purified by silica gel chromatography, eluting with CH₂Cl₂: MeOH—95:5, to give the title compound. MS: m/z=294 (M+1).

Step B. Methyl 4-[3-(2-tert-butoxy-2-oxoethyl)-7-nitro-2-oxo-2,3-dihydro-1H-benzimidazol-1-yl]butanoate Sodium hydride (26.7 mg of a 60% dispersion in mineral oil, 0.66 mmol) was added to a solution of tert-butyl (4-nitro-2-oxo-2,3-dihydro-11H-benzimidazol-1-yl)acetate from Step A (96 mg, 0.327 mmol) in DMF (5 mL). After 10 min, methyl 4-bromobutyrate (178 mg, 0.98 mmol) was added and the reaction was stirred at room temperature for 18 h. The mixture was quenched with H₂O and extracted with EtOAc. The organic extract was washed with brine, dried over Na₂SO₄, filtered, and concentrated in vacuo. The residue was purified by HPLC using a reversed phase C18 column and eluting with a gradient of H₂O:CH₃CN:CF₃CO₂H—90:10:0.1 to 5:95:0.1. Lyophilization provided the title compound. MS: m/z=394 (M+1).

Step C. Methyl 4-[7-amino-3-(2-tert-butoxy-2-oxoethyl)-2-oxo-2,3-dihydro-1H-benzimidazol-1-yl]butanoate A mixture of methyl 4-[3-(2-tert-butoxy-2-oxoethyl)-7-nitro-2-oxo-2,3-dihydro-1H-benzimidazol-1-yl]butanoate from Step B (129 mg, 0.33 mmol) and 10% Pd/C (40 mg) in EtOH (30 mL) and EtOAc (15 mL) was stirred under an atmosphere of hydrogen (ca. 1 atm). After 1 h, the reaction was filtered through a Celite pad and concentrated in vacuo to give the title compound. MS: m/z=364 (M+1).

Step D. tert-Butyl (2,7-dioxo-5,6,7,8-tetrahydro-4H-imidazo[1,5,4-fg][1,6]benzodiazocin-1(2H)-yl)acetate To a solution of methyl 4-[7-amino-3-(2-tert-butoxy-2-oxoethyl)-2-oxo-2,3-dihydro-1H-benzimidazol-1-yl]butanoate from Step C (119 mg, 0.327 mmol) in toluene (5 mL) was added p-toluenesulfonic acid monohydrate (2 mg, 0.011 mmol) and the mixture was heated at reflux. After 3 h, the reaction mixture was allowed to cool to ambient temperature and the mixture was concentrated in vacuo to give the title compound. MS: m/z=332 (M+1).

Step E. (2,7-Dioxo-5,6,7,8-tetrahydro-4H-imidazo[1,5,4-fg][1,6]-benzodiazocin-1(2H)-yl)acetic acid To a solution of tert-butyl (2,7-dioxo-5,6,7,8-tetrahydro-4H-imidazo[1,5,4-fg][1,6]benzodiazocin-1(2H)-yl)acetate from Step D (15 mg, 0.045 mmol) in CH₂Cl₂ (3 mL) was added TFA (1 mL). After 2 h, the mixture was concentrated under reduced pressure to give the title compound. MS: m/z=276 (M+1).

INTERMEDIATE 33

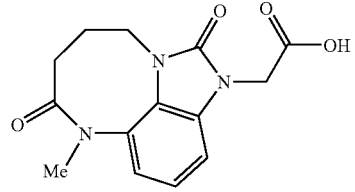

(8-Methyl-2,7-dioxo-5,6,7,8-tetrahydro-4H-imidazo[1,5,4-fg][1,6]benzodiazocin-1(2H)-yl)acetic acid Step A. tert-Butyl (8-methyl-2,7-dioxo-5,6,7,8-tetrahydro-4H-imidazo[1,5,4-fg][1,6]-benzodiazocin-1(2H)-yl)acetate Cesium carbonate (214 mg, 0.66 mmol) and iodomethane (93 mg, 0.66 mmol) were added to a solution of tert-butyl (2,7-dioxo-5,6,7,8-tetrahydro-4H-imidazo[1,5,4-fg][1,6]benzodiazocin-1(2H)-yl)acetate (109 mg, 0.33 mmol, described in Intermediate 32) in DMF (5 mL). After 18 h, the mixture was purified directly by HPLC using a reversed phase C18 column and eluting with a gradient of H₂O:CH₃CN:CF₃CO₂H—90:10:0.1 to 5:95:0.1. Lyophilization provided the title compound. MS: m/z=346 (M+1).

Step B. (8-Methyl-2,7-dioxo-5,6,7,8-tetrahydro-4H-imidazo[1,5,4-fg][1,6]benzodiazocin-1(2H)-yl)acetic acid To a solution of tert-butyl (8-methyl-2,7-dioxo-5,6,7,8-tetrahydro-4H-imidazo[1,5,4-fg][1,6]benzodiazocin-1(2H)-yl)acetate from Step A (45 mg, 0.13 mmol) in CH₂Cl₂ (6 mL) was added TFA (2 mL). After 2 h, the mixture was concentrated under reduced pressure to give the title compound. MS: m/z=290 (M+1).

INTERMEDIATE 34

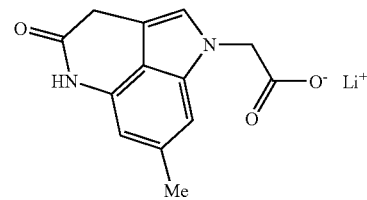

Lithium (7-methyl-4-oxo-4,5-dihydropyrrolo[4,3,12-de]quinolin-1(3H)-yl)acetate

Step A. 2,5-Dimethyl-3-nitroaniline

To a stirred solution of p-xylene (10.4 g, 97.9 mmol) in concentrated sulfuric acid (20 mL), cooled in an ice bath, was added 90% nitric acid (12.4 mL, 264 mmol) dropwise over 50 min. The resulting mixture was heated to 80° C. for 2 h, then poured onto ice and extracted with CH₂Cl₂ (2×400 mL). The combined organic extracts were washed with saturated aqueous NaHCO₃, then brine, then dried over Na₂SO₄, filtered, and concentrated in vacuo. The crude product was partially purified by silica gel chromatography, eluting with a gradient of hexane:EtOAc—90:10 to 60:40. The resulting solid was recrystallized from $CH_2Cl_2$ to yield 2,5-dimethyl-1,3-dinitrobenzene as a white solid. 2,5-Dimethyl-1,3-dinitrobenzene (3.68 g, 18.8 mmol) was dissolved in AcOH (35 mL) and iron powder (1.95 g, 34.9 mmol) was added. The mixture was heated to 110° C. for 3 h, then filtered through a pad of Celite, washing with EtOAc and $H_2O$. The filtrate was concentrated in vacuo to remove most of the solvent and the residue was partitioned between saturated aqueous $NaHCO_3$ (200 mL) and EtOAc (200 mL). The organic layer was washed with brine, then dried over $Na_2SO_4$, filtered, and concentrated in vacuo. The crude product was purified by silica gel chromatography, eluting with a gradient of hexane:EtOAc—100:0 to 60:40, to give the title compound. MS: m/z=167 (M+1).

Step B. 6-Methyl-4-nitro-1H-indole

A solution of 2,5-dimethyl-3-nitroaniline from Step A (1.21 g, 7.26 mmol) and p-toluenesulfonic acid monohydrate (2 mg, 0.011 mmol) in freshly distilled triethyl orthoformate (1.65 mL, 9.92 mmol) was heated at 120° C. for 45 min in a distillation apparatus, and about 0.4 mL of EtOH distilled over. Vacuum distillation of the residual solution yielded ethyl 2,5-dimethyl-3-nitrophenylimidoformate (b.p.=146° C., ca. 2 mm Hg) as a pale yellow solid. To a solution of diethyl oxalate (868 mg, 5.94 mmol) in DMF (2 mL), at 0° C., was added potassium ethoxide (435 mg, 5.17 mmol) and the resulting solution was added to a solution of ethyl 2,5-dimethyl-3-nitrophenylimidoformate (880 mg, 3.96 mmol) in DMSO (3 mL). The reaction mixture was heated at 40° C. for 1 h than quenched with $H_2O$ (30 mL) and extracted with EtOAc (2×50 mL). The combined organic layers were washed with brine, then dried over $Na_2SO_4$, filtered, and concentrated in vacuo. The crude product was purified by silica gel chromatography, eluting with a gradient of hexane:EtOAc—100:0 to 0:100, to give the title compound. MS: m/z=177 (M+1).

Lithium (7-methyl-4-oxo-4,5-dihydropyrrolo[4,3,2-de]quinolin-1(3H)-yl)acetate

Essentially following the procedures described for Intermediate 46, but using 6-methyl-4-nitro-1H-indole in place of 4-nitroindole, the title compound was prepared. MS: m/z=245 (M+1).

INTERMEDIATE 35

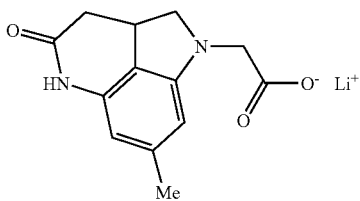

Lithium (7-methyl-4-oxo-2a,3,4,5-tetrahydropyrrolo[4,3,2-de]quinolin-1 (2H)-yl)acetate, enantiomer B Essentially following the procedures described for Intermediate 47, but using 6-methyl-4-nitro-1H-indole (described in Intermediate 34) in place of 4-nitroindole, the title compound was prepared. MS: m/z=247 (M+1).

INTERMEDIATE 36

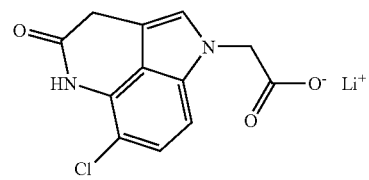

Lithium (6-chloro-4-oxo-4,5-dihydropyrrolo[4,3,2-de]quinolin-1(3H)-yl)acetate

Step A. tert-Butyl[4-amino-3-(cyanomethyl)-1H-indol-1-yl]acetate

A mixture of tert-butyl[3-(cyanomethyl)-4-nitro-1H-indol-1-yl]acetate (700 mg, 2.22 mmol, described in Intermediate 46) and 10% Pd/C (65 mg) in EtOH (20 mL) was stirred under an atmosphere of hydrogen (ca. 1 atm). After 4 h, the reaction was filtered through a Celite pad and concentrated in vacuo to give the title compound. MS: m/z=286 (M+1).

Step B. tert-Butyl[4-amino-5-chloro-3-(cyanomethyl-1H-indol-1-yl]acetate

To a solution of tert-butyl[4-amino-3-(cyanomethyl)-1H-indol-1-yl]acetate from Step A (150 mg, 0.526 mmol) in $CH_2Cl_2$ (5 mL) was added N-chlorosuccinimide (70 mg, 0.526 mmol). The reaction mixture was stirred at ambient temperature for 30 min, then partitioned between saturated aqueous $NaHCO_3$ (5 mL) and $CHCl_3$ (15 mL). The aqueous phase was extracted further with $CHCl_3$ (15 mL) and the combined organic extracts were dried over $Na_2SO_4$, filtered, and concentrated in vacuo to give the title compound, which was of sufficient purity for use in the next step. MS: m/z=320 (M+1).

Lithium (6-chloro-4-oxo-4,5-dihydropyrrolo[4,3,2-de]quinolin-1(3H)-yl)acetate

Essentially following the procedures described for Intermediate 46, but using tert-butyl[4-amino-5-chloro-3-(cyanomethyl)-1H-indol-1-yl]acetate in place of tert-butyl[3-(cyanomethyl)-4-nitro-1H-indol-1-yl]acetate, the title compound was prepared. MS: m/z=283 (M+1).

INTERMEDIATE 37

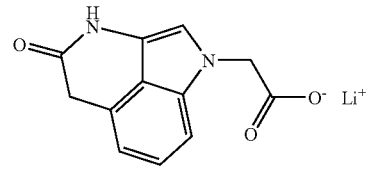

Lithium (4-oxo-4,5-dihydropyrrolo[2,3,4-ij]isoquinolin-1(3H)-yl)acetate

Step A. 4-Bromo-1-(phenylsulfonyl)-1H-indole

To a solution of 4-bromoindole (1.00 g, 5.10 mmol) in DMF (50 mL) at ambient temperature was added sodium hydride (220 mg of a 60% dispersion in mineral oil, 5.50 mmol). The reaction mixture was stirred for 5 min, then benzenesulfonyl chloride (901 mg, 5.10 mmol) was added and stirring was continued for 15 min. The reaction was quenched with saturated aqueous NaHCO$_3$ (50 mL) and extracted with CHCl$_3$ (2×75 mL). The combined organic extracts were dried over Na$_2$SO$_4$, filtered, and concentrated in vacuo. The crude product was purified by silica gel chromatography, eluting with a gradient of hexane:EtOAc—100:0 to 90:10, to give the title compound. MS: m/z=336 (M+1).

Step B. tert-Butyl[1-(phenylsulfonyl)-1H-indol-4-yl]acetate

To a mixture of 1,3-bis(2,6-diisopropylphenyl)-4,5-dihydroimidazolium tetrafluoroborate (94 mg, 0.196 mmol), tris(dibenzylideneacetone)dipalladium (180 mg, 0.196 mmol), and lithium bis(trimethylsilyl)amide (1.37 M in t-BuOMe, 11.0 mL, 15.1 mmol) were added 4-bromo-1-(phenylsulfonyl)-1H-indole from Step A (2.20 g, 6.54 mmol), tert-butyl acetate (988 mg, 8.51 mmol), and toluene (15 mL). The resulting mixture was stirred at ambient temperature for 18 h then partitioned between Et$_2$O (100 mL) and saturated aqueous NH$_4$Cl (30 mL). The organic layer was washed with brine, then dried over Na$_2$SO$_4$, filtered, and concentrated in vacuo. The crude product was purified by silica gel chromatography, eluting with a gradient of hexane:EtOAc—100:0 to 85:15, to give the title compound. MS: m/z=316 (M—C$_4$H$_7$).

Step C. tert-Butyl[3-nitro-1-(phenylsulfonyl)-1H-indol-4-yl]acetate

To acetic anhydride (5 mL) at 0° C. was added 90% nitric acid (0.183 mL, 3.90 mmol) and the resulting mixture was aged for 10 min, then added dropwise to a solution of tert-butyl[1-(phenylsulfonyl)-1H-indol-4-yl]acetate from Step B (1.00 g, 2.69 mmol) in acetic anhydride (5 mL) at −78° C. The reaction mixture was stirred at −78° C. for 6 h, then aged at −20° C. for 16 h, then quenched with H$_2$O and extracted with EtOAc (2×10 mL). The combined organic extracts were dried over Na$_2$SO$_4$, filtered, and concentrated in vacuo. The crude product was purified by silica gel chromatography, eluting with a gradient of hexane:EtOAc—100:0 to 70:30, to give the title compound. MS: m/z=361 (M—C$_4$H$_7$).

Step D. tert-Butyl[3-nitro-1H-indol-4-yl]acetate

To a solution of tert-butyl[3-nitro-1-(phenylsulfonyl)-1H-indol-4-yl]acetate from Step C (730 mg, 1.75 mmol) in THF (5 mL) was added tetrabutylammonium fluoride (1.0 M in THF, 5.25 mL, 5.25 mmol) and the reaction mixture was stirred at ambient temperature for 10 min, then concentrated in vacuo. The residue was partitioned between saturated aqueous NaHCO$_3$ (5 mL) and extracted with CHCl$_3$ (15 mL). The organic extract was dried over Na$_2$SO$_4$, filtered, and concentrated in vacuo. The crude product was purified by silica gel chromatography, eluting with a gradient of CHCl$_3$:EtOAc 90:10 to 50:50, to give the title compound. MS: m/z=221 (M—C$_4$H$_7$).

Step E. tert-Butyl[1-(2-ethoxy-2-oxoethyl)-3-nitro-1H-indol-4-yl]acetate

To a solution of tert-butyl[3-nitro-1H-indol-4-yl]acetate from Step D (385 mg, 1.39 mmol) in DMF (5 mL) at ambient temperature was added sodium hydride (60 mg of a 60% dispersion in mineral oil, 1.50 mmol). The reaction mixture was stirred for 5 min, then ethyl bromoacetate (256 mg, 1.53 mmol) was added and stirring was continued for 10 min. The reaction was quenched with saturated aqueous NaHCO$_3$ (5 mL) and extracted with CHCl$_3$ (2×25 mL). The combined organic extracts were dried over Na$_2$SO$_4$, filtered, and concentrated in vacuo. The crude product was purified by silica gel chromatography, eluting with a gradient of hexane:EtOAc—90:10 to 40:60, to give the title compound. MS: m/z=307 (M—C$_4$H$_7$).

Step F. [1-(2-Ethoxy-2-oxoethyl)-3-nitro-1H-indol-4-yl]acetic acid

To a solution of tert-butyl[1-(2-ethoxy-2-oxoethyl)-3-nitro-1H-indol-4-yl]acetate from Step E (300 mg, 0.828 mmol) in CH$_2$Cl$_2$ (1 mL) was added TFA (0.63 mL, 8.28 mmol). The mixture was stirred at ambient temperature for 1 h then concentrated in vacuo to give the title compound. MS: m/z=307 (M+1).

Step G. Ethyl (4-oxo-4,5-dihydropyrrolo[2,3,4-ij]isoquinolin-1(3H)-yl)acetate

To a solution of [1-(2-ethoxy-2-oxoethyl)-3-nitro-1H-indol-4-yl]acetic acid from Step F (250 mg, 0.816 mmol) in AcOH (18 mL) and H$_2$O (2 mL) was added iron powder (456 mg, 8.16 mmol) and the reaction mixture was heated at 80° C. for 18 h. The mixture was concentrated in vacuo to remove most of the solvent and the residue was partitioned between saturated aqueous NaHCO$_3$ (5 mL) and EtOAc (25 mL). The organic layer was washed with brine, then dried over Na$_2$SO$_4$, filtered, and concentrated in vacuo to give the title compound, which was of sufficient purity for use in the next step. MS: m/z=259 (M+1).

Step H. Lithium (4-oxo-4,5-dihydropyrrolo[2,3,4-ij]isoquinolin-1(3H)-yl)acetate

To a solution of ethyl (4-oxo-4,5-dihydropyrrolo[2,3,4-#]isoquinolin-1(3H)-yl)acetate from Step G (200 mg, 0.77 mmol) in THF (1 mL), EtOH (1 mL) and H$_2$O (1 mL) was added 1.0 N lithium hydroxide (0.85 mL, 0.85 mmol). After 15 min, 1 N aqueous HCl was added to adjust the solution to pH 7 and the mixture was concentrated in vacuo to give the title compound. MS: m/z=231 (M+1).

INTERMEDIATE 38

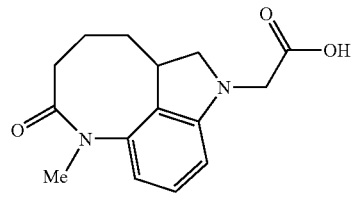

(7-Methyl-6-oxo-2a,3,4,5,6,7-hexahydroazocino[4,3,2-cd]indol-1(2H)-yl)acetic acid, enantiomer A Step A. Ethyl 4-(4-nitro-1H-indol-3-yl)-4-oxobutanoate To a stirred solution of 4-nitroindole (2.00 g, 12.3 mmol) in CH$_2$Cl$_2$ (60 mL) at 0° C. was added dimethylaluminum chloride (1 M in hexanes, 14.8 mL, 14.8 mmol) and the mixture was stirred for 30 min. Ethyl 4-chloro-4-oxobutyrate (2.44 g, 14.8 mmol) was added dropwise and the resulting mixture was allowed to warm slowly to ambient temperature and stirred for 18 h. The reaction mixture was carefully quenched with 10% aqueous citric acid (150 mL) and extracted with $CH_2Cl_2$ (3×150 mL). The combined organic extracts were dried over $Na_2SO_4$, filtered, and concentrated in vacuo. The residue was partially purified by silica gel chromatography, eluting with a gradient of $CH_2Cl_2$:EtOAc—100:0 to 65:35, and the resulting crude product was recrystallized from $CH_2Cl_2$:MeOH to give the title compound. MS: m/z=291 (M+1).

Step B. Ethyl 4-(4-nitro-2,3-dihydro-1H-indol-3-yl)butanoate

Triethylsilane (11 mL, 68 mmol) was added to a solution of ethyl 4-(4-nitro-1H-indol-3-yl)-4-oxobutanoate from Step A (960 mg, 3.31 mmol) in TFA (15 mL). After 3 h, the reaction mixture was concentrated in vacuo and the residue was purified by silica gel chromatography, eluting with a gradient of $CHCl_3$:MeOH—100:0 to 94:6, to give the title compound. MS: m/z=279 (M+1).

Step C. Ethyl 4-[1-(2-tert-butoxy-2-oxoethyl)-4-nitro-2,3-dihydro-1H-indol-3-yl]butanoate To a solution of ethyl 4-(4-nitro-2,3-dihydro-1H-indol-3-yl)butanoate from Step B (1.10 g, 3.95 mmol), sodium carbonate (628 mg, 5.93 mmol), and potassium iodide (131 mg, 0.79 mmol) in acetone (10 mL) was added tert-butyl bromoacetate (17.5 mL, 119 mmol). The mixture was heated at reflux for 18 h, then cooled to ambient temperature and concentrated in vacuo. The residue was partitioned between $H_2O$ (30 mL) and EtOAc (2×60 mL) and the organic extracts were dried over $Na_2SO_4$, filtered, and concentrated in vacuo. The crude product was purified by silica gel chromatography, eluting with a gradient of hexane:EtOAc—90:10 to 65:35, to give the title compound. MS: m/z=365 (M+1).

Step D. Ethyl 4-[4-amino-1-(2-tert-butoxy-2-oxoethyl)-2,3-dihydro-1H-indol-3-yl]butanoate A mixture of ethyl 4-[1-(2-tert-butoxy-2-oxoethyl)-4-nitro-2,3-dihydro-1H-indol-3-yl]butanoate from Step C (1.10 g, 2.80 mmol) and 10% Pd/C (150 mg) in EtOH (50 mL) was stirred under an atmosphere of hydrogen (ca. 1 atm). After 18 b, the reaction was filtered through a Celite pad and concentrated in vacuo to give the title compound. MS: m/z/z 363 (M+1).

Step E. Lithium 4-[4-amino-1-(2-tert-butoxy-2-oxoethyl)-2,3-dihydro-1H-indol-3-yl]butanoate To a solution of ethyl 4-[4-amino-1-(2-tert-butoxy-2-oxoethyl)-2,3-dihydro-1H-indol-3-yl]butanoate from Step D (1.00 g, 2.76 mmol) in THF (30 mL), EtOH (15 mL) and $H_2O$ (15 mL) was added 1.0 N lithium hydroxide (2.76 mL, 2.76 mmol). After 15 min, 1 N aqueous HCl was added to adjust the solution to pH 7 and the mixture was concentrated in vacuo to give the title compound, which was of sufficient purity for use in the next step. MS: m/z=335 (M+1).

Step F. tert-Butyl (6-oxo-2a,3,4,5,6,7-hexahydroazocino[4,3,2-cd]indol-1(2H)-yl)acetate, enantiomer A A mixture of lithium 4-[4-amino-1-(2-tert-butoxy-2-oxoethyl)-2,3-dihydro-1H-indol-3-yl]butanoate from Step E (900 mg, 2.69 mmol), EDC (1.29 g, 6.73 mmol), HOAT (916 mg, 6.73 mmol), and N,N-diisopropylethylamine (0.94 mL, 5.38 mmol) was stirred in DMF (10 mL) at ambient temperature for 4 h, then concentrated under reduced pressure. The residue was partitioned between saturated aqueous $NaHCO_3$ (5 mL) and EtOAc (50 mL). The organic layer was washed with $H_2O$ (5 mL), then 10% aqueous citric acid (5 mL), then dried over $Na_2SO_4$, filtered, and concentrated in vacuo. The crude product was purified by silica gel chromatography, eluting with a gradient of hexane:EtOAc—80:20 to 0:100, to give the racemic product. The enantiomers were resolved by HPLC, utilizing a Chiralpak AS column and eluting with $CH_3CN$:MeOH—25:75. The first major peak to elute was tert-butyl (6-oxo-2a,3,4,5,6,7-hexahydroazocino[4,3,2-cd]indol-1(2H)-yl)acetate, enantiomer A, the title compound, and the second major peak to elute was tert-butyl (6-oxo-2a,3,4,5,6,7-hexahydroazocino[4,3,2-cd]indol-1(2B)-yl)acetate, enantiomer B. MS: m/z=317 (M+1).

Step G. tert-Butyl (7-methyl-6-oxo-2a,3,4,5,6,7-hexahydroazocino[4,3,2-cd]indol-1(2H)-yl)acetic acid, enantiomer A To a solution of tert-butyl (6-oxo-2a,3,4,5,6,7-hexahydroazocino[4,3,2-cd]indol-1(2H)-yl)acetate, enantiomer A, from Step F (20 mg, 0.063 mmol) in DMF (0.5 mL) at ambient temperature was added sodium hydride (3 mg of a 60% dispersion in mineral oil, 0.075 mmol). The reaction mixture was stirred for 5 min, then iodomethane (10 mg, 0.070 mmol) was added and stirring was continued for 10 min. The reaction was quenched with saturated aqueous $NaHCO_3$ (1 mL) and extracted with EtOAc (2×3 mL). The combined organic extracts were dried over $Na_2SO_4$, filtered, and concentrated in vacuo to give the title compound. MS: m/z=331 (M+1).

Step H. (7-Methyl-6-oxo-2a,3,4,5,6,7-hexahydroazocino[4,3,2-cd]indol-1(2H)-yl)acetic acid, enantiomer A A solution of tert-butyl (7-methyl-6-oxo-2a,3,4,5,6,7-hexahydroazocino[4,3,2-cd]indol-1(2H)-yl)acetate, enantiomer A, from Step G (18 mg, 0.057 mmol) in EtOAc (1 mL) was saturated with HCl (g), aged at ambient temperature for 10 min, then resaturated with HCl (g). After a further 10 min, the mixture was concentrated in vacuo to give the title compound. MS: m/z=275 (M+1).

INTERMEDIATE 39

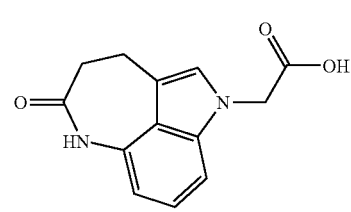

(5-Oxo-3,4,5,6-tetrahydro-1H-azepino[4,3,2-cd]indol-1-yl)acetic acid

Step A. Ethyl 4-(4-nitro-1H-indol-3-yl)propanoate

A mixture of 4-nitroindole (1.00 g, 6.17 mmol), Meldrum's acid (889 mg, 6.17 mmol), proline (36 mg, 0.31 mmol), and formaldehyde (37% in $H_2O$, 0.50 mL, 6.17 mmol) was stirred in CH₃CN (4 mL) at ambient temperature for 18 h. The reaction mixture was quenched with H₂O (20 mL) and extracted with EtOAc (2×20 mL). The combined organic extracts were dried over Na₂SO₄, filtered, and concentrated in vacuo. After drying under high vacuum, the solid residue was dissolved in pyridine (16 mL) and EtOH (4 mL). To the resulting solution was added copper powder (50 mg, 0.79 mmol) and the mixture was heated at reflux for 2 h then allowed to cool. The solvent was removed in vacuo, and the residue was partitioned between saturated aqueous NaHCO₃ (25 mL) and EtOAc (50 mL). The organic extract was dried over Na₂SO₄, filtered, and concentrated in vacuo. The crude product was purified by silica gel chromatography, eluting with a gradient of hexane:CH₂Cl₂—20:80 to 0:100, to give the title compound. MS: m/z=263 (M+1).

Step B. Ethyl 3-[1-(2-tert-butoxy-2-oxoethyl)-4-nitro-1H-indol-3-yl]propanoate

To a solution of ethyl 4-(4-nitro-1H-indol-3-yl)propanoate from Step A (860 mg, 3.28 mmol) in DMF (15 mL), was added sodium hydride (142 mg of a 60% dispersion in mineral oil, 3.55 mmol). After 5 min, tert-butyl bromoacetate (0.581 mL, 3.94 mmol) was added dropwise and the reaction mixture was stirred at room temperature for 10 min then quenched with H₂O and extracted with CHCl₃ (3×35 mL). The combined organic extracts were dried over Na₂SO₄, filtered, and concentrated in vacuo. The crude product was purified by silica gel chromatography, eluting with a gradient of hexane:EtOAc—90:10 to 30:70, to give the title compound. MS: m/z=321 (M—C₄H₇).

Step C. Ethyl 3-[4-amino-1-(2-tert-butoxy-2-oxoethyl)-1H-indol-3-yl]propanoate

A mixture of ethyl 3-[1-(2-tert-butoxy-2-oxoethyl)-4-nitro-1H-indol-3-yl]propanoate from Step B (1.20 g, 3.19 mmol) and 10% Pd/C (150 mg) in EtOH (100 mL) was stirred under an atmosphere of hydrogen (ca. 1 atm). After 1 h, the reaction mixture was filtered through a Celite pad and concentrated in vacuo to give the title compound. MS: m/z=347 (M+1).

Step D. tert-Butyl (5-oxo-3,4,5,6-tetrahydro-1H-azepino[4,3,2-cd]indol-1-yl)acetate To a solution of ethyl 3-[4-amino-1-(2-tert-butoxy-2-oxoethyl)-1H-indol-3-yl]propanoate from Step C (1.00 g, 2.89 mmol) in toluene (50 mL) was added p-toluenesulfonic acid monohydrate (5 mg, 0.026 mmol) and the mixture was heated at reflux. After 2 h, the reaction was allowed to cool to ambient temperature and the mixture was washed with saturated aqueous NaHCO₃ (10 mL). The organic layer was dried over Na₂SO₄, filtered, and concentrated in vacuo. The crude product was purified by silica gel chromatography, eluting with a gradient of CH₂Cl₂:MeOH—100:0 to 92:8, to give the title compound. MS: m/z=301 (M+1).

Step E. (5-Oxo-3,4,5,6-tetrahydro-1H-azepino[4,3,2-cd]indol-1-yl)acetic acid

To a solution of tert-butyl (5-oxo-3,4,5,6-tetrahydro-1H-azepino[4,3,2-cd]indol-1-yl)acetate from Step D (100 mg, 0.33 mmol) in (1 mL) was added TFA (0.25 mL, 3.3 mmol) and the resulting mixture was stirred at ambient temperature for 1 h. The mixture was concentrated in vacuo to give the title compound. MS: m/z=245 (M+1).

INTERMEDIATE 40

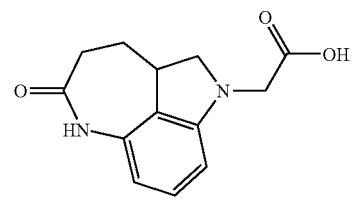

(5-Oxo-2,2a,3,4,5,6-hexahydro-1H-azepino[4,3,2-cd]indol-1-yl)acetic acid, enantiomer A Step A. (±)-Ethyl 3-(4-nitro-2,3-dihydro-1H-indol-3-yl)propanoate Triethylsilane (16 mL, 99 mmol) was added to a solution of ethyl 4-(4-nitro-1H-indol-3-yl)propanoate (1.30 g, 4.96 mmol, described in Intermediate 39) in TFA (25 mL). After 1 h, the reaction mixture was concentrated in vacuo and the residue was purified by silica gel chromatography, eluting with a gradient of CHCl₃:MeOH—100:0 to 94:6, to give the title compound. MS: m/z=265 (M+1).

Step B. (±)-Ethyl 3-[1-(2-tert-butoxy-2-oxoethyl)-4-nitro-2,3-dihydro-1H-indol-3-yl]propanoate To a solution of (±)-ethyl 3-(4-nitro-2,3-dihydro-1H-indol-3-yl)propanoate from Step A (980 mg, 3.71 mmol), sodium carbonate (590 mg, 5.56 mmol), and potassium iodide (123 mg, 0.74 mmol) in acetone (10 mL) was added tert-butyl bromoacetate (16.4 mL, 111 mmol). The mixture was heated at reflux for 18 h, then cooled to ambient temperature and concentrated in vacuo. The residue was partitioned between H₂O (30 mL) and EtOAc (2×60 mL) and the organic extracts were dried over Na₂SO₄, filtered, and concentrated in vacuo. The crude product was purified by silica gel chromatography, eluting with a gradient of hexane:EtOAc—100:0 to 65:35, to give the title compound. MS: m/z=379 (M+1).

(5-Oxo-2,2a,3,4,5,6-hexahydro-1H-azepino[4,3,2-cd]indol-1-yl)acetic acid, enantiomer A Essentially following the procedures described for Intermediate 39, but using (±)-ethyl 3-[1-(2-tert-butoxy-2-oxoethyl)-4-nitro-2,3-dihydro-1H-indol-3-yl]propanoate in place of ethyl 3-[1-(2-tert-butoxy-2-oxoethyl)-4-nitro-1H-indol-3-yl]propanoate, and resolving the racemate into pure enantiomers in analogy with Intermediate 47, the title compound was prepared. MS: m/z=303 (M+1).

INTERMEDIATE 41

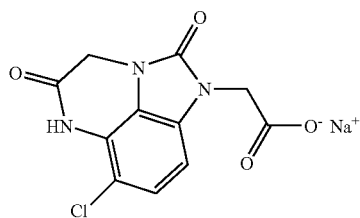

Sodium (7-chloro-2,5-dioxo-5,6-dihydro-4H-imidazo[1,5,4-de]quinoxalin-1(2H)-yl)acetate

Step A. 5-Chloro-2,1,3-benzoselenadiazole

A solution of 4-chlorobenzene-1,2-diamine (1.50 g, 10.5 mmol) in EtOH (15 mL) was heated to reflux and selenium dioxide (1.28 g, 11.5 mmol) was added. The reaction was refluxed for 30 min and cooled to ambient temperature. The precipitated solid was filtered, washed thoroughly with $H_2O$ and dried under high vacuum to give the title compound. MS: m/z=219 (M+1).

Step B. 5-Chloro-4-nitro-2,1,3-benzoselenadiazole

A solution of 5-chloro-2,1,3-benzoselenadiazole from Step A (800 mg, 1.80 mmol) in conc. $H_2SO_4$ (12 mL) was cooled to 0° C. and 90% $HNO_3$ (0.8 mL) was added. After 30 min the reaction was cooled to 0° C. and diluted with $H_2O$ (10 mL). The solid was filtered off and washed with cold $H_2O$ to yield the title compound. MS: m/z=263 (M+1).

Step C. 5-Chloro-4-nitro-1,3-dihydro-2H-benzimidazol-2-one

A solution of 5-chloro-4-nitro-2,1,3-benzoselenadiazole from Step B (650 mg, 2.47 mmol) in conc. HCl (4 mL) and 48% aqueous HI (2 mL) was stirred at ambient temperature for 2 h. The reaction was diluted with a 1:1 saturated aqueous solution of $NaHSO_4$ and $Na_2CO_3$ (20 mL) and then adjusted to pH 10 using 10 M aqueous NaOH. The mixture was extracted with EtOAc (3×110 mL) and the organic extracts dried over $Na_2SO_4$, filtered, and concentrated in vacuo. The resulting dark red solid was dissolved in $CH_3CN$ (4 mL) and phosgene was added (20% solution in toluene, 1.5 mL, 3.2 mmol). The reaction mixture was stirred for 1 h, then diluted with toluene. Filtration of the resultant solid gave the title compound. MS: m/z=214 (M+1).

Step D. Dimethyl 2,2'-(5-chloro-4-nitro-2-oxo-1H-benzimidazole-1,3-diyl)diacetate Cesium carbonate (1.16 g, 3.60 mmol) was added to a solution of 5-chloro-4-nitro-1,3-dihydro-2H-benzimidazol-2-one from Step A (255 mg, 1.20 mmol) and methyl bromoacetate (0.23 mL, 2.40 mmol) in DMF (5 mL). After 1.5 h, the reaction was quenched with $H_2O$ (30 mL) and the solid precipitate was collected by filtration to give the title compound. MS: m/z=359 (M+1).

Step E. Methyl (7-chloro-2,5-dioxo-5,6-dihydro-4H-imidazo[1,5,4-de]quinoxalin-1(2H)-yl)acetate To a solution of dimethyl 2,2'-(5-chloro-4-nitro-2-oxo-1H-benzimidazole-1,3-diyl)diacetate (100 mg, 0.28 mmol) from Step D in AcOH (1.0 mL) and water (0.11 mL) was added fine granular iron (78 mg, 1.4 mmol) and the slurry was heated at 70° C. for 1 h. The reaction was cooled, filtered, concentrated and dissolved in DMF (4 mL). The DMF solution was added dropwise to $H_2O$ (30 mL) with stirring and the precipitate was isolated by filtration to give the title compound. MS: m/z 296 (M+1).

Step F. Sodium (7-chloro-2,5-dioxo-5,6-dihydro-4H-imidazo[1,5,4-de]quinoxalin-1(2H)-yl)acetate Essentially following the procedures described for Intermediate 45, but using methyl (7-chloro-2,5-dioxo-5,6-dihydro-4H-imidazo[1,5,4-de]quinoxalin-1(2R)-yl)acetate in place of methyl (6-methyl-2,5-dioxo-5,6-dihydro-4H-imidazo[1,5,4-de]quinoxalin-1(2H)-yl)acetate, the title compound was prepared MS: m/z=282 (M+1).

INTERMEDIATE 42

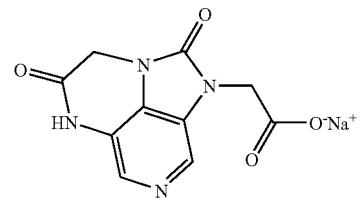

Sodium (2,4-dioxo-4,5-dihydro-3H-1,2a,5,7-tetraazaacenaphthylen-1(2H)-yl)acetate

Step A. 2,6-Dichloro-3-nitro-pyridin-4-amine

To a solution of 2,6-dichloro-4-aminopyridine (5.0 g, 30.6 mmol) in conc. $H_2SO_4$ (25 mL) at 0° C. in an ice-acetone bath was added 90% $HNO_3$ (10 mL) dropwise. The reaction mixture was warmed to ambient temperature and stirred for 1 h then poured onto ice (100 g). The solid precipitate was isolated by filtration, washed with cold $H_2O$ and dried under high vacuum. The resulting solid was dissolved in conc. $H_2SO_4$ (50 mL) and heated at 100° C. for 20 min. The reaction mixture was poured onto ice (150 g) and neutralized with conc. $NH_4OH$ while maintaining the temperature below 20° C. The precipitate was isolated by filtration, washed with cold $H_2O$, and dried to yield the title compound. MS: m/z=209 (M+1).

Step B. 2,6-Dichloro-pyridine-3,4-diamine

To a solution of 2,6-dichloro-3-nitro-pyridin-4-amine (2.6 g, 14.4 mmol) from Step A in MeOH (150 mL) was added Raney Nickel catalyst (2 g) and the reaction agitated under a hydrogen atmosphere in a Parr apparatus (35 p.s.i.) for 2 h. The reaction mixture was filtered through a pad of Celite and concentrated to yield the title compound. MS: w/z=179 (M+1).

Step C. 4,6-Dichloro-1,3-dihydro-2H-imidazo[4,5-c]pyridin-2-one

A mixture of 2,6-dichloro-3,4-dihydropyridine-3,4-diamine (500 mg, 2.8 mmol) from Step B and urea (1.0 g, 16.8 mmol) was stirred as a melt at 165° C. for 4 h, then cooled and $H_2O$ (100 mL) was added. The aqueous mixture was heated at reflux until all solid dissolved and the solution was allowed to cool and aged for 18 h. The precipitate was isolated by filtration to give the title compound. MS: m/z=205 (M+1).

Step D. 4,6-Dichloro-7-nitro-1,3-dihydro-2H-imidazo[4,5-c]pyridin-2-one

To a solution of 4,6-dichloro-1,3-dihydro-2H-imidazo[4,5-c]pyridin-2-one (0.6 g, 2.94 mmol) from Step C in conc. $H_2SO_4$ (15 mL) was added $KNO_3$ (2.97 g, 29.4 mmol) and the reaction mixture was heated at 125° C. for 2 h. After cooling, the reaction was mixed with ice and the solid precipitate was isolated by filtration and washed with cold 1420 to give the title compound. MS: m/z=250 (M+1).

Step E. Dimethyl 22'-(4,6-dichloro-7-nitro-2-oxo-1H-imidazo[4,5-c]pyridine-1,3-diyl)diacetate Cesium carbonate (2.39 g, 7.33 mmol) was added to a solution of 4,6-dichloro-7-nitro-1,3-dihydro-2H-imidazo[4,5-c]pyridin-2-one from Step D (610 mg, 2.45 mmol) and methyl bromoacetate (0.47 mL, 5.02 mmol) in DMF (5 mL). After 1.5 h, the reaction was quenched with $H_2O$ (30 mL) and the solid precipitate was collected by filtration to give the title compound. MS: m/z=394 (M+1).

Step F. Methyl (2,4-dioxo-4,5-dihydro-3H-1,2a,5,7-tetraazaacenaphthylen-1(2T)-yl)acetate A mixture of dimethyl 2,2'-(4,6-dichloro-7-nitro-2-oxo-1H-imidazo[4,5-c]pyridine-1,3-diyl)diacetate (40 mg, 0.10 mmol) from Step E and 10% Pd/C (12 mg) in MeOH (2 mL) was stirred under an atmosphere of hydrogen (ca. 1 atm) for 6 h. The reaction mixture was filtered through a pad of Celite and concentrated in vacuo. The crude material was heated at 80° C. for 2 h in toluene (2 mL) and AcOH (2 mL) then concentrated to give the title compound. MS: m/z=263 (M+1).

Step G. Sodium (2,4-dioxo-4,5-dihydro-3H-1,2a,5,7-tetraazaacenaphthylen-1(2H)-yl)acetate Essentially following the same procedures described for Intermediate 31, but using methyl (2,4-dioxo-4,5-dihydro-3H-1,2a,5,7-tetraazaacenaphthylen-1(2H)-yl)acetate in place of methyl (2,5-dioxo-5,6-dihydro-4H-imidazo[1,5,4-de]quinoxalin-1(2H)-yl)acetate, the title compound was prepared. MS: m/z=249 (M+1).

INTERMEDIATE 43

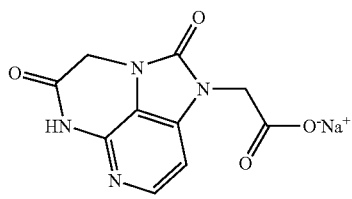

Sodium (2,4-dioxo-4,5-dihydro-3H-1,2a,5,6-tetraazaacenaphthylen-1(2H)-yl)acetate Step A.
1,3-Dihydro-2H-imidazo[4,5-c]pyridin-2-one A combination of pyridine-3,4-diamine (1.0 g, 9.16 mmol) and urea (3.3 g, 54.9 mmol) were stirred as a melt at 165° C. for 4 h, then cooled and $H_2O$ (100 mL) was added. The aqueous mixture was heated at reflux until all solid dissolved and the solution was allowed to cool and aged for 18 h. The precipitate was isolated by filtration to give the title compound. MS: m/z=136 (M+1).

Step B. Sodium (2,4-dioxo-4,5-dihydro-3H-1,2a,5,6-tetraazaacenaphthylen-1(2H)-yl)acetate Essentially following the procedures described for Intermediate 42, but using 1,3-dihydro-2H-imidazo[4,5-c]pyridin-2-one in place of 4,6-dichloro-1,3-dihydro-2H-imidazo[4,5-c]pyridin-2-one, the title compound was prepared. MS: m/z=249 (M+1).

INTERMEDIATE 44

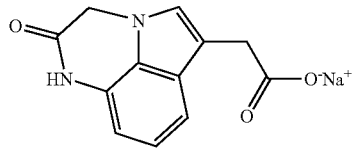

Sodium (2-oxo-2,3-dihydro-1H-pyrrolo[2,3-de]quinoxalin-6-yl)acetate

Step A.
N,N-Dimethyl-1-(7-nitro-1H-indol-3-yl)methanamine

A mixture of 7-nitro-1H-indole (3 g, 18.5 mmol), 40% aqueous dimethylamine (3.12 mL, 27.7 mmol) and 37% aqueous formaldehyde (1.57 mL, 19.3 mmol) was stirred for three days at ambient temperature. The reaction mixture was diluted with $H_2O$ (20 mL) followed 15% aqueous NaOH (200 mL) and extracted with $CHCl_3$ (3×200 mL). The combined organic extracts were dried over $Na_2SO_4$, filtered, and concentrated in vacuo to give the title compound in sufficient purity for use in the next step. MS: m/z=181 (M+1).

Step B. Methyl (7-nitro-1H-indol-3-yl)acetate

A solution of N,N-dimethyl-1-(7-nitro-1H-indol-3-yl)methanamine from Step A (3.3 g, 18.5 mmol) in DMF (3 mL), $H_2O$ (3 mL), THF (150 mL) and iodomethane (2.85 mL, 45.7 mmol) was heated at reflux for 15 min as a white precipitate formed. Potassium cyanide (6.0 g, 92.1 mmol) was added and reflux was continued for 2 h. The cooled solution was filtered and concentrated under reduced pressure and the residue was triturated with MeOH to give (7-nitro-1H-indol-3-yl)acetonitrile as a yellow solid. A suspension of this solid in MeOH (10 mL) was cooled to 0° C. and HCl (g) was bubbled in slowly for 30 min. The reaction mixture was aged for 1 h, then concentrated in vacuo. To the residue was added 6 M aqueous HCl (20 mL) and the mixture was extracted with EtOAc (3×20 mL). The combined organic extracts were washed with saturated aqueous $NaHCO_3$ (50 mL), then brine (20 mL), dried over $Na_2SO_4$, filtered, and concentrated to give the title compound. MS: m/z=235 (M+1).

Step C. Dimethyl 2,2'-(7-nitro-1H-indole-1,3-diyl)diacetate

To a solution of methyl (7-nitro-1H-indol-3-yl)acetate from Step B (545 mg, 2.71 mmol) was added cesium carbonate (927 mg, 2.85 mmol) and methyl bromoacetate (0.26 mL, 2.84 mmol) in DMF (10 mL). The reaction mixture was stirred at ambient temperature for 18 h, then quenched with $H_2O$ (50 mL). The solid precipitate was collected by filtration to give the title compound. MS: m/z=274 (M+1).

Step D. Sodium (2-oxo-2,3-dihydro-1H-pyrrolo[1,2,3-de]quinoxalin-6-yl)acetate

Essentially following the procedures described for Intermediate 31, but using dimethyl 2,2'-(7-nitro-1H-indole-1,3-diyl)diacetate in place of dimethyl 2,2'-(4-nitro-2-oxo-1H-benzimidazole-1,3-diyl)diacetate, the title compound was prepared. MS: m/z=231 (M+1).

INTERMEDIATE 45

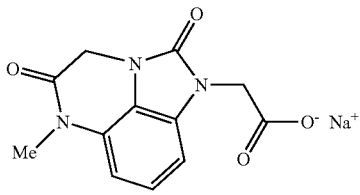

Sodium (6-methyl-2,5-dioxo-5,6-dihydro-4H-imidazo[1,5,4-de]quinoxalin-1(2H)-yl)acetate

Step A. Methyl (6-methyl-2,5-dioxo-5,6-dihydro-4H-imidazo[1,5,4-de]quinoxalin-1(2H)-yl)acetate To a solution of methyl (2,5-dioxo-5,6-dihydro-4H-imidazo[1,5,4-de]quinoxalin-1(2B)-yl)acetate (300 mg, 1.15 mmol, described in Intermediate 31) in DMF (5 mL) were added cesium carbonate (748 mg, 2.3 mmol) and iodomethane (326 mg, 2.3 mmol). After 16 h, the reaction mixture was quenched with brine (20 mL) and extracted with EtOAc (50 mL). The organic layer was dried over $Na_2SO_4$, filtered, and concentrated in vacuo to give the title compound. MS: m/z=276 (M+1).

Step B. Sodium (6-methyl-2,5-dioxo-5,6-dihydro-4H-imidazo[1,5,4-de]quinoxalin-1(2H)-yl)acetate To a solution of methyl (6-methyl-2,5-dioxo-5,6-dihydro-4H-imidazo[1,5,4-de]quinoxalin-1(2H)-yl)acetate from Step A (225 mg, 0.817 mol) in MeOH (10 mL) was added 1.0 N sodium hydroxide (1.2 mL, 1.2 mmol). After 3 h, the reaction mixture was neutralized with 1 N aqueous HCl and concentrated to give the title compound. MS: m/z=262 (M+1).

INTERMEDIATE 46

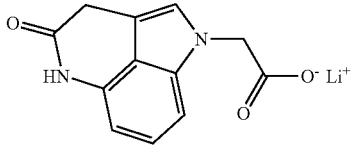

Lithium (4-oxo-4,5-dihydropyrrolo[4,3,2-de]quinolin-1(3H)-yl)acetate

Step A. N,N-Dimethyl-1-(4-nitro-1H-indol-3-yl)methanamine

N,N,N',N'-Tetramethyldiaminomethane (2.2 mL, 15.6 mol) in acetic acid (30 mL) was added dropwise over 60 min to a solution of 4-nitroindole (2.30 g, 14.2 mol) in acetic acid (30 mL). After 3.5 h, the reaction was cooled to 0° C., and 20% aqueous sodium hydroxide was added to adjust the pH to 11. The mixture was extracted with $CHCl_3$ (3×300 mL) and the combined organic extracts were dried over $Na_2SO_4$, filtered, and concentrated in vacuo to give the title compound. MS: m/z=220 (M+1).

Step B. (4-Nitro-1H-indol-3-yl)acetonitrile

Potassium cyanide (9.20 g, 141 mmol) in $H_2O$ (80 mL) was added to a solution of N,N-dimethyl-1-(4-nitro-1H-indol-3-yl)methanamine from Step A (3.10 g, 14.1 mmol) in DMF (80 mL) and the mixture was heated at reflux for 1 h, then cooled to ambient temperature and partitioned between $H_2O$ (200 mL) and EtOAc (400 mL). The organic layer was dried over $Na_2SO_4$, filtered, and concentrated in vacuo. The crude product was purified by silica gel chromatography, eluting with a gradient of hexane:EtOAc—100:0 to 0:100, to give the title compound. MS: m/z=265 (M+Na+$CH_3CN$).

Step C. tert-Butyl[3-(cyanomethyl)-4-nitro-1H-indol-1-yl]acetate

Sodium hydride (198 mg of a 60% dispersion in mineral oil, 5.0 mmol) was added to a solution of (4-nitro-1H-indol-3-yl)acetonitrile from Step B (910 mg, 4.52 mmol) in DMF (15 mL). After 10 min, tert-butyl bromoacetate (0.801 mL, 5.4 mmol) was added dropwise and the reaction mixture was stirred at ambient temperature for 1.5 h. The mixture was partitioned between $H_2O$ (50 mL) and EtOAc (100 mL) and the organic extract was washed with brine, dried over $Na_2SO_4$, filtered, and concentrated in vacuo. The crude product was purified by silica gel chromatography, eluting with a gradient of hexane:EtOAc—100:0 to 0:100, to give the title compound. MS: m/z=316 (M+1).

Step D. 2,2'-(4-Nitro-1H-indole-1,3-diyl)diacetic acid

To a solution of tert-butyl[3-(cyanomethyl)-4-nitro-1H-indol-1-yl]acetate from Step C (920 mg, 2.92 mol) in ethanol (50 mL) was added 1.0 N aqueous sodium hydroxide (14.6 mL, 14.6 mmol) and the mixture was heated at reflux for 18 h. An additional amount of 1.0 N sodium hydroxide (15 mL, 15 mmol) was added to the reaction, most of the EtOH was distilled out of the flask, and the mixture was heated at reflux for a further 21 h. The reaction mixture was cooled to 0° C. and concentrated HCl was added to adjust the pH to 1-2. The mixture was extracted with EtOAc (2×150 mL) and the combined organic extracts were dried over $Na_2SO_4$, filtered, and concentrated in vacuo to give the title compound. MS: m/z=279 (M+1).

Step E. Diethyl 2,2'-(4-nitro-1H-indole-1,3-diyl)diacetate

Concentrated sulfuric acid (0.02 mL) was added to a solution of 2,2'-(4-nitro-1H-indole-1,3-diyl)diacetic acid from Step D (742 mg, 2.67 mol) in EtOH (100 mL) and the mixture was heated at reflux for 9 h. The reaction mixture was allowed to cool to ambient temperature and was concentrated to a volume of 30 mL in vacuo. The solution was partitioned between EtOAc (300 mL) and aqueous $NaHCO_3$ (100 mL) and the organic layer was dried over $Na_2SO_4$, filtered, and concentrated in vacuo to give the title compound. MS: m/z=335 (M+1).

Step F. Diethyl 2,2'-(4-amino-1H-indole-1,3-diyl)diacetate

A mixture of diethyl 2,2'-(4-nitro-1H-indole-1,3-diyl)diacetate from Step E (140 mg, 0.419 mmol) and 10% Pd/C (20 mg) in EtOH (20 mL) was stirred under an atmosphere of hydrogen (ca-1 atm). After 1.5 h, the reaction mixture was filtered through a Celite pad and concentrated in vacuo to give the title compound. MS: m/z=305 (M+1).

Step G. Ethyl (4-oxo-4,5-dihydropyrrolo[4,3,2-de]quinolin-1(3H)-yl)acetate

To a solution of diethyl 2,2'-(4-amino-1H-indole-1,3-diyl)diacetate from Step F (83 mg, 0.273 mmol) in toluene (8 mL) was added p-toluenesulfonic acid monohydrate (5 mg, 0-026 mmol) and the mixture was heated at reflux. After 2 h, the reaction was allowed to cool to ambient temperature and the mixture was partitioned between EtOAc (40 mL) and aqueous $NaHCO_3$ (15 mL). The organic layer was washed with brine, dried over $Na_2SO_4$, filtered, and concentrated in vacuo. The crude product was purified by silica gel chromatography, eluting with a gradient of $CH_2Cl_2$:MeOH—100:0 to 92:8, to give the title compound. MS: m/z=259 (M+1).

Step H. Lithium (4-oxo-4,5-dihydropyrrolo[4,3,2-de]quinolin-1(3H)-yl)acetate To a solution of ethyl (4-oxo-4,5-dihydropyrrolo[4,3,2-de]quinolin-1(3B)-yl)acetate from Step G (79 mg, 0.306 mmol) in ethanol (3 mL) and water (0.5 mL) was added dropwise 1.0 N aqueous lithium hydroxide (0.34 mL, 0.34 mmol). After 5 min, 1 N aqueous HCl was added to adjust the mixture to pH 7 and the solution was concentrated in vacuo to give the title compound. MS: m/z=231 (M+1).

INTERMEDIATE 47

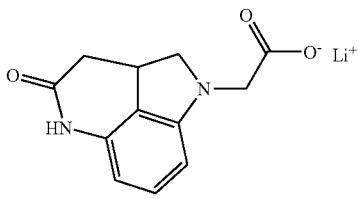

Lithium (4-oxo-2a,3,4,5-tetrahydropyrrolo[4,3,2-de]quinolin-1(2H-yl)acetate, enantiomer B

Step A. Methyl (4-nitro-1H-indol-3-yl)(oxo)acetate

Diphosphoryl chloride (0.938 mL, 6.80 mmol) was added dropwise to a solution of 4-nitroindole (1.00 g, 6.17 mmol) and methylpyrrolidinyl glyoxylate (Downie et al., *Tetrahedron*, 1993, 49, 4015-4034) (1.10 g, 6.80 mmol) at 0° C. and the mixture was allowed to warm to ambient temperature over 3 h. MeOH, then saturated aqueous $NaHCO_3$ were added to the reaction at 0° C. and the solution was extracted with $CH_2Cl_2$ (3×50 mL). The combined organic extracts were dried over $Na_2SO_4$, filtered, and concentrated in vacuo until crystals formed. The crystals were collected by vacuum filtration and two more crops were isolated from the filtrate to give the title compound. MS: m/z=249 (M+1).

Step B. (±)-Methyl (4-nitro-2,3-dihydro-1H-indol-3-yl)acetate

Triethylsilane (13 mL, 80.6 mmol) was added to a solution of methyl (4-nitro-1H-indol-3-yl)(oxo)acetate from Step A (1.00 g, 4.03 mmol) in TFA (15 mL). After 3 h, the reaction mixture was concentrated in vacuo and the residue was purified by silica gel chromatography, eluting with a gradient of $CHCl_3$:MeOH—100:0 to 98:2, to give the title compound. MS: m/z=237 (M+1).

Step C. (±)-Ethyl methyl 2,2'-(4-nitro-2,3-dihydro-1H-indole-1,3-diyl)diacetate To a solution of (±)-methyl (4-nitro-2,3-dihydro-1H-indol-3-yl)acetate from Step B (700 mg, 2.97 mmol), sodium carbonate (471 mg, 4.44 mmol), and potassium iodide (98 mg, 0.59 mmol) in acetone (15 mL) was added ethyl bromoacetate (9.9 mL, 88.9 mmol). The mixture was heated at reflux for 18 h, then cooled to ambient temperature and concentrated in vacuo. The residue was partitioned between $H_2O$ (15 mL) and EtOAc (2×40 mL) and the organic extracts were washed with brine, dried over $Na_2SO_4$, filtered, and concentrated in vacuo to a volume of 50 mL. Hexane was added to the EtOAc solution and a precipitate formed. The desired crystals were collected by vacuum filtration to give the title compound. MS: m/z=323 (M+1).

Step D. (±)-Ethyl methyl 2,2'-(4-amino-2,3-dihydro-1H-indole-1,3-diyl)diacetate A mixture of (±)-ethyl methyl 2,2'-(4-nitro-2,3-dihydro-1H-indole-1,3-diyl)diacetate from Step C (550 mg, 1.71 mmol) and 10% Pd/C (40 mg) in EtOH (10 mL) was stirred under an atmosphere of hydrogen (ca. 1 atm). After 3 h, the reaction was filtered through a Celite pad and concentrated in vacuo to give the title compound. MS: m/z=293 (M+1).

Step E. Ethyl (4-oxo-2a,3,4,5-tetrahydropyrrolo[4,3,2-de]quinolin-1(2H)-yl)acetate, enantiomer B To a solution of (±)-ethyl methyl 2,2'-(4-amino-2,3-dihydro-1H-indole-1,3-diyl)diacetate from Step D (490 mg, 1.70 mmol) in toluene (35 mL) was added p-toluenesulfonic acid monohydrate (5 mg, 0.026 mmol) and the mixture was heated at reflux for 48 h. The mixture was cooled to ambient temperature and was partitioned between saturated aqueous $NaHCO_3$ (5 mL) and EtOAc (40 mL). The organic layer was dried over $Na_2SO_4$, filtered, and concentrated in vacuo. The crude product was purified by silica gel chromatography, eluting with a gradient of $CHCl_3$:EtOAc—90:10 to 40:60, to give the racemic product. The enantiomers were resolved by HPLC, utilizing a Chiralpak AS column and eluting with MeOH. The first major peak to elute was ethyl (4-oxo-2a,3,4,5-tetrahydropyrrolo[4,3,2-de]quinolin-1(2H)-yl)acetate, enantiomer A, and the second major peak to elute was ethyl (4-oxo-2a,3,4,5-tetrahydropyrrolo[4,3,2-de]quinolin-1(2H)-yl)acetate, enantiomer B, the title compound. MS: m/z=261 (M+1).

Step F. Lithium (4-oxo-2a,3,4,5-tetrahydropyrrolo[4,3,2-de]quinolin-1(2H)-yl)acetate, enantiomer B To a solution of ethyl (4-oxo-2a,3,4,5-tetrahydropyrrolo[4,3,2-de]quinolin-1(2B)-yl)acetate, enantiomer B, from Step E (55 mg, 0.211 mmol) in THF (1 mL), EtOH (1 mL) and $H_2O$ (1 mL) was added 1.0 N lithium hydroxide (0.232 mL, 0.232 mmol). After 15 min, 1 N aqueous HCl was added to adjust the solution to pH 7 and the mixture was concentrated in vacuo to give the title compound. MS: m/z=233 (M+1).

INTERMEDIATE 48

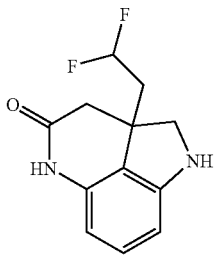

2a-(2,2-Difluoroethyl)-1,2,2a,5-tetrahydropyrrolo[4,3,2-de]quinolin-4(3)-one, enantiomer A Step A. 2a-(2,2-Difluoroethyl)-1.22a,5-tetrahydropyrrolo[4,3,2-de]quinolin-4(3H)-one, enantiomer A To a stirred solution of tert-butyl 4-oxo-2a-(2-oxoethyl)-2a,3,4,5-tetrahydropyrrolo[4,3,2-de]quinolin-1(2B)-carboxylate, enantiomer A, (150 mg, 0.474 mmol, described in Intermediate 29) in CH$_2$Cl$_2$ (2 mL) at 0° C. was added DAST (0.125 mL, 0.948 mmol) and the mixture was stirred for 1 h. Additional DAST (0.066 mL) was added and the mixture was stirred for 1 h. To the resulting mixture was added TFA (2 mL) and stirring was continued for 1 h. The mixture was concentrated in vacuo and partitioned between saturated aqueous NaHCO$_3$ (10 mL) and CH$_2$Cl$_2$ (10 mL). The layers were separated and the aqueous layer further extracted with CH$_2$Cl$_2$ (2×10 mL). The combined organic layers were dried over Na$_2$SO$_4$, filtered, and concentrated in vacuo. The crude product was purified by silica gel chromatography, eluting with a gradient of CH$_2$Cl$_2$:MeOH—100:0 to 95:5, to give the title compound. MS: m/z=239 (M+1).

INTERMEDIATE 49

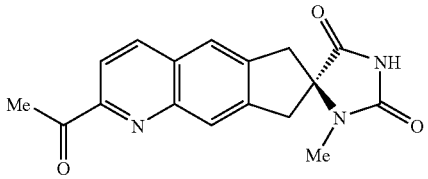

(7R)-2-Acetyl-3'-methyl-6,8-dihydro-2'H,5'H-spiro[cyclopenta[g]quinoline-7,4'-imidazolidine]-2',5'-dione Step A. (7R)-2-(1-Hydroethyl)-3'-methyl-6,8-dihydro-2'H,5'H-spiro[cyclopenta[g]quinoline-7,4-imidazolidine]-2',5'-dione To a suspension of (7R)-3'-methyl-2',5'-dioxo-6,8-dihydrospiro[cyclopenta[g]quinoline-7,4'-imidazolidine]-2-carbaldehyde (90 mg, 0.305 mmol, described in Intermediate 13) in THF (20 mL) at −78° C. was added methyl magnesium bromide (0.31 mL of a 3 M solution in Et$_2$O, 0.93 mmol). The reaction mixture was stirred for 30 min at −78° C. and 2 h at ambient temperature. The reaction was quenched by the addition of water and partitioned between water (20 mL) and EtOAc (20 mL). The layers were separated and the aqueous layer was further extracted with EtOAc (2×20 mL). The combined organic layers were dried over Na$_2$SO$_4$, filtered, and concentrated in vacuo to yield the title compound, which was used without further purification. MS: m/z=312 (M+1).

Step B. (7R)-2-Acetyl-3'-methyl-6,8-dihydro-2'H,5'H-spiro[cyclopenta[g]quinoline-7,4'-imidazolidine]-2',5'-dione A mixture of (7R)-2-(1-hydroxyethyl)-3'-methyl-6,8-dihydro-2'H,5'H-spiro[cyclopenta[g]quinoline-7,4'-imidazolidine]-2',5'-dione from Step A (95 mg, 0.305 mmol) and manganese dioxide (255 mg, 9.06 mmol) in dioxane (5 mL) and CHCl$_3$ (5 mL) was heated at reflux for 48b. The reaction mixture was filtered through a pad of Celite, washing with CH$_2$Cl$_2$-MeOH, and the filtrate was concentrated under reduced pressure. The crude product was purified by silica gel chromatography, eluting with a gradient of CH$_2$Cl$_2$:MeOH—100:0 to 95:5, to give the title compound. MS: m/z=310 (M+1).

INTERMEDIATE 50

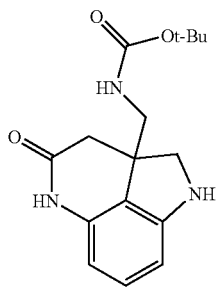

tert-Butyl[(4-oxo-1,2,4,5-tetrahydropyrrolo[4,3,2-de]quinolin-2a(3H)-yl)methyl]carbamate, enantiomer A Step A. (±)-2a-[(1,3-Dioxo-1,3-dihydro-2H-isoindol-2-yl)methyl]-2a,5-dihydropyrrolo[4,3,2-de]quinoline-2,4(1H,3H)-dione To a stirred solution of (±)-2a,5-dihydropyrrolo[4,3,2-de]quinoline-2,4(1H,3H)-dione (2.00 g, 10.6 mmol, described in Intermediate 17) in degassed DMF (30 mL) at 0° C. was added sodium hydride (468 mg of a 60% dispersion in mineral oil, 11.7 mmol). The mixture was stirred for 10 min, then N-(bromomethyl)phthalimide (2.55 g, 10.6 mmol) was added and stirring was continued for 2 h. An additional portion of N-(bromomethyl)phthalimide (500 mg) was added and stirring was continued for 1 h. The reaction mixture was quenched with saturated aqueous NaHCO$_3$ (100 mL) and extracted with EtOAc (3×50 mL). The combined organic extracts were dried over Na$_2$SO$_4$, filtered, and concentrated in vacuo. The crude product was purified by silica gel chromatography, eluting with a gradient of CH$_2$Cl$_2$:MeOH—100:0 to 90:10, to give the title compound. MS: m/z=348 (M+1).

Step B. (±)-2a-(Aminomethyl)-2a,5-dihydropyrrolo[4,3,2-de]quinoline-2,4(1H,3R)-dione A solution of (A)-2a-[(1,3-dioxo-1,3-dihydro-2H-isoindol-2-yl)methyl]-2a,5-dihydropyrrolo[4,3,2-de]quinoline-2,4(1H,3H)-dione from Step A (2.30 g, 6.62 mmol) and hydrazine (1.05 mL, 33.1 mmol) in EtOH (30 mL) was heated at 70° C. for 2 h, then cooled to ambient temperature and filtered. The filtrate was concentrated in vacuo. The crude product was purified by silica gel chromatography, eluting with a gradient of $CH_2Cl_2$:MeOH:$NH_4OH$—100:0:0 to 90:9:1, to give the title compound. MS: m/z=218 (M+1).

Step C. (+A-tert-Butyl (2,4-dioxo-1,2,4,5-tetrahydropyrrolo[4,3,2-de]quinolin-2a(3H)-yl)methylcarbamate To a solution of (±)-2a-(aminomethyl)-2a,5-dihydropyrrolo[4,3,2-de]quinoline-2,4(1H,3H)-dione from Step B (1.08 g, 4.97 mmol) and di-tert-butyl dicarbonate (1.30 g, 5.97 mmol) in $CH_2Cl_2$ (20 mL) and EtOH (10 mL) was added triethylamine (1.39 mL, 9.94 mmol). The reaction mixture was stirred for 16 h and then concentrated in vacuo. The crude product was purified by silica gel chromatography, eluting with a gradient of $CH_2Cl_2$:MeOH:$NH_4OH$—100:0:0 to 95:5:1, to give the title compound. MS: m/z=318 (M+1).

Step D. tert-Butyl[(4-oxo-1,2,4,5-tetrahydropyrrolo [4,3,2-de]quinolin-2a(3H)-yl)methyl]carbamate enantiomer A To a solution of (±)-tert-butyl (2,4-dioxo-1,2,4,5-tetrahydropyrrolo[4,3,2-de]quinolin-2a(3H)-yl)methylcarbamate from Step C (1.20 g, 3.78 mmol) in THF (20 mL) at 0° C. was added DIBAL-H (18.9 mL of a 1 M solution in toluene, 18.9 mmol). The reaction mixture was stirred for 2 h and then quenched by the slow addition of saturated aqueous sodium potassium tartrate (100 mL) and extracted with EtOAc (3×50 mL). The combined organic extracts were dried over $Na_2SO_4$, filtered, and concentrated in vacuo. The crude product was purified by silica gel chromatography, eluting with a gradient of $CH_2Cl_2$:MeOH:$NH_4OH$—100:0:0 to 95:5:1, to give (±)-tert-butyl[(2-oxo-1,2,4,5-tetrahydropyrrolo[4,3,2-de]quinolin-2a(3H)-yl)methyl]carbamate, which eluted first, and the racemic title compound, which eluted second. The enantiomers were resolved by HPLC, utilizing a ChiralPak AD column and eluting with hexane:EtOH:$Et_2NH$—60:40:0.1. The first major peak to elute was tert-butyl [(4-oxo-1,2,4,5-tetrahydropyrrolo[4,3,2-de]quinolin-2a(3H)-yl)methyl]carbamate, enantiomer A, the title compound, and the second major peak to elute was tert-butyl[(4-oxo-1,2,4,5-tetrahydropyrrolo[4,3,2-de]quinolin-2a(3H)-yl)methyl]carbamate, enantiomer B. MS: m/z=304 (M+1).

INTERMEDIATE 51

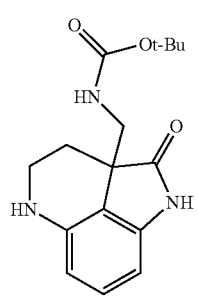

(±)-tert-Butyl[(2-oxo-1,2,4,5-tetrahydropyrrolo[4,3, 2-de]quinolin-2a(3)-yl)methyl]carbamate Step A. (±)-tert-Butyl[(2-oxo-1,2,4,5-tetrahydropyrrolo[4,3,2-de]quinolin-2a(3H)-yl)methyl]carbamate The title compound was obtained from the same reaction as Intermediate 50. The crude product was purified by silica gel chromatography, eluting with a gradient of $CH_2Cl_2$:MeOH: NOH—100:0:0 to 95:5:1, to give the title compound, which eluted first, and (±)-tert-butyl[(4-oxo-1,2,4,5-tetrahydropyrrolo[4,3,2-de]quinolin-2a(3B)-yl)methyl]carbamate, which eluted second. MS: m/z=304 (M+1).

INTERMEDIATE 52

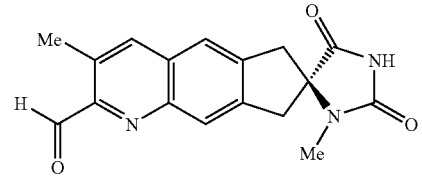

(7R)-3,3'-Dimethyl-2',5'-dioxo-6,8-dihydrospiro[cyclopenta[g]quinoline-7,4'-imidazolidine]-2-carbaldehyde Step A. (7R)-3,3'-Dimethyl-2',5'-dioxo-6,8-dihydrospiro[cyclopenta[g]quinoline-7,4'-imidazolidine]-2-carbaldehyde Essentially following the procedures described for Intermediate 13, but using trans-2-methyl-2-butenal in place of crotonaldehyde, the title compound was prepared. MS: m/z=327 (M+1+$H_2O$).

INTERMEDIATE 53

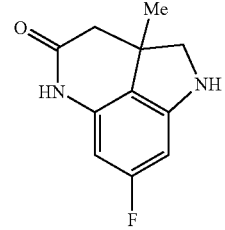

7-Fluoro-2a-methyl-1,2,2a,5-tetrahydropyrrolo[4,3, 2-de]quinolin-4(3L)-one, enantiomer A Step A. Dimethyl 2-(4-fluoro-2,6-dinitrophenyl)malonate To a solution of dimethyl malonate (16.3 mL, 143 mmol) in DMA (100 mL) at ambient temperature was added potassium tert-butoxide (15.3 g, 136 mmol). The reaction mixture was heated to 70° C. for 30 min, then removed from the oil bath. A solution of 2-chloro-5-fluoro-1,3-dinitrobenzene (14.3 g, 64.9 mmol) in dioxane (70 mL) was added drop wise over 30 min. The reaction mixture was stirred for 10 min, then cooled and poured onto saturated aqueous $NH_4Cl$ (500 mL). The aqueous layer was extracted with EtOAc (250 mL) and $Et_2O$ (2×250 mL). The combined organic extracts were washed with $H_2O$ (100 mL), dried over $Na_2SO_4$, and concentrated in vacuo to give the title compound, which was used without further purification. MS: m/z=317 (M+1).

Step B. Methyl (4-fluoro-2,6-dinitrophenyl)acetate

A solution of dimethyl 2-(4-fluoro-2,6-dinitrophenyl)malonate from Step A (20.5 g, 64.9 mmol) and lithium chloride (5.50 g, 130 mmol) in DMSO (120 mL) and water (2.34 mL) was heated at 90° C. for 3 h, then cooled and poured onto H₂O (400 mL). The aqueous layer was extracted with Et₂O (3×250 mL). The combined organic layers were washed with brine (100 mL), dried over Na₂SO₄, and concentrated in vacuo. The crude product was purified by silica gel chromatography, eluting with a gradient of hexanes:EtOAc—100:0 to 80:20, to give the title compound. MS: m/z=259 (M+1).

Step C. (±)-4-Ethyl 1-methyl 2-(4-fluoro-2,6-dinitrophenyl)succinate

To a solution of methyl (4-fluoro-2,6-dinitrophenyl)acetate from Step B (9.51 g, 36.8 mmol) and ethyl bromoacetate (8.17 mL, 73.6 mmol) in DMF (100 mL) was added cesium carbonate (18.0 g, 55.2 mmol). The reaction mixture was stirred for 16 h and then poured onto H₂O (500 mL). The aqueous layer was extracted with EtOAc (3×250 mL). The combined organic layers were washed with H₂O (100 mL), dried over Na₂SO₄, and concentrated in vacuo. The crude product was purified by silica gel chromatography, eluting with a gradient of hexanes:EtOAc—100:0 to 80:20, to give the title compound. MS: m/z=345 (M+1).

Step D. (±)-Ethyl (4-amino-6-fluoro-2-oxo-2,3-dihydro-1H-indol-3-yl)acetate

A solution of (±)-4-ethyl 1-methyl 2-(4-fluoro-2,6-dinitrophenyl)succinate from Step C (7.23 g, 21.0 mmol) and iron powder (5.86 g, 105 mmol) in EtOH (60 mL) and saturated aqueous NH₄Cl (15 mL) was stirred at reflux for 4.5 h. The warm reaction mixture was filtered through Celite, rinsing the filter cake with ethyl acetate. The crude product solution was washed with saturated aqueous NaHCO₃ (300 mL). The layers were separated and the aqueous layer was further extracted with EtOAc (2×200 mL). The combined organic layers were dried over Na₂SO₄, and concentrated in vacuo. The crude product was purified by silica gel chromatography, eluting with a gradient of hexanes:EtOAc—100:0 to 50:50, to give the title compound. MS: m/z=253 (M+1).

Step E. (±)-7-Fluoro-2a,5-dihydropolo[4,3,2-de]quinoline-2,4(1H,3)-dione

A solution of (±)-ethyl (4-amino-6-fluoro-2-oxo-2,3-dihydro-1H-indol-3-yl)acetate from Step D (3.28 g, 13.0 mmol) in degassed xylenes (100 mL) and AcOH (5 mL) was heated at reflux for 4.5 days, then allowed to slowly cool to ambient temperature. The resulting precipitate was filtered, washing with hexanes, to give the title compound. MS: m/z=207 (M+1).

Step F. (±)-7-Fluoro-2a-methyl-2a,5-dihydropyrrolo[4,3,2-de]quinoline-2,4(1H,3H)-dione To a stirred solution of (±)-7-fluoro-2a,5-dihydropyrrolo[4,3,2-de]quinoline-2,4(1H,3B)-dione from Step E (608 mg, 2.95 mmol) in degassed DMF (10 mL) at 0° C. was added sodium hydride (142 mg of a 60% dispersion in mineral oil, 3.54 mmol). The mixture was stirred for 15 min, then iodomethane (0.184 mL, 2.95 mmol) was added and stirring was continued for 1 h. The reaction mixture was poured onto H₂O (100 mL) and extracted with EtOAc (3×50 mL). The combined organic extracts were washed with H₂O (20 mL), dried over Na₂SO₄, filtered, and concentrated in vacuo. The crude product was purified by silica gel chromatography, eluting with a gradient of CH₂Cl₂:EtOAc—100:0 to 0:100, to give the title compound. MS: m/z=221 (M+1).

Step G. 7-Fluoro-2a-methyl-1,2,2a,5-tetrahydropyrrolo[4,3,2-de]quinolin-4(3-H)-one enantiomer A To a solution of (±)-7-fluoro-2a-methyl-2a,5-dihydropyrrolo[4,3,2-de]quinoline-2,4(1H,3B)-dione from Step F (340 mg, 1.54 mmol) in THF (10 mL) at 0° C. was added DIBAL-H (7.72 mL of a 1 M solution in toluene, 7.72 mmol). The reaction mixture was stirred for 2 h and then quenched by the slow addition of saturated aqueous sodium potassium tartrate (100 mL) and extracted with EtOAc (3×50 mL). The combined organic extracts were washed with brine (20 mL), dried over Na₂SO₄, filtered, and concentrated in vacuo. The crude product was purified by silica gel chromatography, eluting with a gradient of CH₂Cl₂:MeOH:NH₄OH—100:0:0 to 95:5:1, to give the racemic title compound. The enantiomers were resolved by HPLC, utilizing a ChiralPak AD column and eluting with MeOH. The first major peak to elute was 7-fluoro-2a-methyl-1,2,2a,5-tetrahydropyrrolo[4,3,2-de]quinolin-4(3H)-one, enantiomer A, the title compound, and the second major peak to elute was 7-fluoro-2a-methyl-1,2,2a,5-tetrahydropyrrolo[4,3,2-de]quinolin-4(3)-one, enantiomer B. MS: m/z=207 (M+1).

INTERMEDIATE 54

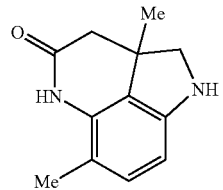

(±)-2a,6-Dimethyl-1,2,2a,5-tetrahydropyrrolo[4,3,2-de]quinolin-4(3H)-one

Step A. (±)-2a-Methyl-1,2,2a,5-tetrahydropyrrolo[4,3,2-de]quinolin-4(3H)-one

Essentially following the procedures described for Intermediate 53 but using 2-chloro-1,3-dinitrobenzene in place of 2-chloro-5-fluoro-1,3-dinitrobenzene, the title compound was obtained. MS: m/z=189(M+1).

Step B. (±)-6-Bromo-2a-methyl-1,2,2a,5-tetrahydropyrrolo[4,3,2-de]quinolin-4(3H)-one To a solution of (±)-2a-methyl-1,2,2a,5-tetrahydropyrrolo[4,3,2-de]quinolin-4(3H)-one from Step A (525 mg, 2.79 mmol) in CH₂Cl₂ (15 mL) at 0° C. was added N-bromosuccinimide (496 mg, 2.79 mmol) and the mixture was allowed to warm slowly to ambient temperature. After 5 h, the reaction mixture was quenched with saturated aqueous NaHCO₃ (10 mL) and extracted with EtOAc (150 mL). The organic layer was washed with brine, dried over Na₂SO₄, filtered, and concentrated in vacuo. The crude product was purified by silica gel chromatography, eluting with a gradient of CH₂Cl₂:CH₃CN—100:0 to 75:25, to give the title compound. MS: m/z=267 (M+1).

Step C. (±)-2a,6-Dimethyl-1,2,2a,5-tetrahydropyrrolo[4,3,2-de]quinolin-4(3H)-one A mixture of (±)-6-bromo-2a-methyl-1,2,2a,5-tetrahydropyrrolo[4,3,2-de]quinolin-4(3H)-one from Step B (48 mg, 0.18 mmol), tetrakis(triphenylphosphine)palladium(0) (22 mg, 0.019 mmol), potassium carbonate (75 mg, 0.54 mmol), and trimethylboroxine (0.126 mL of a 50 wt. % solution in THF, 0.50 mmol) in 1,4-dioxane (0.9 mL) and $H_2O$ (0.1 mL) was heated at 120° C. in a microwave reactor for 40 min. The cooled reaction mixture was quenched with $H_2O$ (5 mL) and extracted with EtOAc (20 mL). The organic layer was washed with brine, dried over $Na_2SO_4$, filtered, and concentrated in vacuo. The crude product was purified by silica gel chromatography, eluting with a gradient of $CH_2Cl_2$:MeOH—100:0 to 90:10, to give the title compound. MS: m/z=203 (M+1).

INTERMEDIATE 55

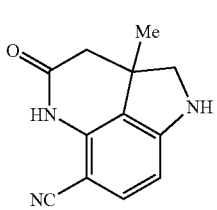

(±)-2a-Methyl-4-oxo-1,2,2a,3,4,5-hexahydropyrrolo[4,3,2-de]quinoline-6-carbonitrile Step A. (±)-2a-Methyl-4-oxo-1,2,2a,3,45-hexahydropyrrolo[4,3,2-de]quinoline-6-carbonitrile A mixture of (±)-6-bromo-2a-methyl-1,2,2a,5-tetrahydropyrrolo[4,3,2-de]quinolin-4(30 mL)-one (53 mg, 0.20 mmol, described in Intermediate 54), tetrakis(triphenylphosphine)palladium(0) (48 mg, 0.042 mmol), and copper(I) cyanide (27 mg, 0.30 mmol) in DMF (2 mL) was heated at 150° C. for 3 h. The cooled reaction mixture was quenched with aqueous $NaHCO_3$ (10 mL) and extracted with EtOAc (30 mL). The organic layer was washed with brine, dried over $Na_2SO_4$, filtered, and concentrated in vacuo. The crude product was purified by silica gel chromatography, eluting with a gradient of hexane:EtOAc—60:40 to 0:100, to give the title compound in sufficient purity for use in the next step. MS: m/z=214 (M+1).

Example 1

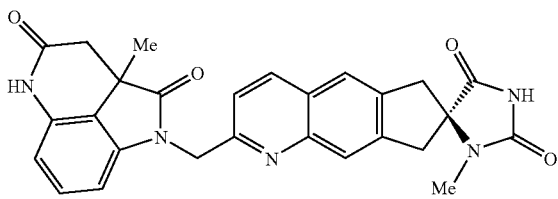

(7R)-3'-Methyl-2-[(2a-methyl-2,4-dioxo-2a,3,4,5-tetrahydropyrrolo[4,3,2-de]quinolin-1(2H)-yl-methyl]-6,8-dihydro-2'H,5'H-spiro[cylopenta[g]quinoline-7,4'-imidazolidine]-2',5'-dione, diastereomer B To a solution of 2a-methyl-2a,5-dihydropyrrolo[4,3,2-de]quinoline-2,4(1H,3B)-dione, enantiomer B, (128 mg, 0.63 mmol, described in Intermediate 16) in DMF (1 mL), at 0° C., was added sodium hydride (60% dispersion in mineral oil; 28 mg, 0.70 mmol) and the resulting mixture was stirred for 30 min. A solution of (7R)-2-(chloromethyl)-3'-methyl-6,8-dihydro-2'H,5'H-spiro[cyclopenta[g]quinoline-7,4'-imidazolidine]-2',5'-dione (100 mg, 0.32 mmol, described in Intermediate 14) in DMF (1 mL) was added dropwise and the resulting mixture was stirred at ambient temperature for 2 h. The reaction mixture was quenched with a few drops of TFA and purified directly by HPLC using a reversed phase C18 column and eluting with a gradient of $H_2O$:$CH_3CN$:$CF_3CO_2H$—90:10:0.1 to 5:95:0.1. The pure, product-containing fractions were combined and poured into saturated aqueous $NaHCO_3$ (10 mL). The mixture was extracted with $CH_2Cl_2$ (3×10 mL). A precipitate was isolated from the organic layers by filtration. The combined organic extracts were dried over $Na_2SO_4$, filtered, and concentrated in vacuo to give a residue. This residue was combined with the filtered solid to give the title compound. MS: m/z=482 (M+1). HRMS: m/z=482.1824; calculated m/z=482.1823 for $C_{27}H_{24}NSO_4$.

Example 2

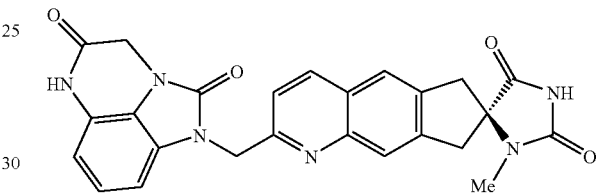

(7R)-2-[(2,5-Dioxo-5,6-dihydro-4H-imidazo[1,5,4-de]quinoxalin-1(2H)-yl)methyl]-3'-methyl-6,8-dihydro-2'H,5'H-spiro[cyclopenta[g]quinoline-7,4'-imidazolidine]-2',5'-dione Step A. Methyl (3-{[(7R)-3'-methyl-2',5'-dioxo-6,8-dihydrospiro[cyclopenta[g]quinoline-7,4-imidazolidin]-2-yl]methyl}-7-nitro-2-oxo-2,3-dihydro-1H-benzimidazol-1-yl)acetate To a solution of methyl (7-nitro-2-oxo-2,3-dihydro-1H-benzimidazol-1-yl)acetate (68 mg, 0.27 mmol, described in Intermediate 15) in DMF (1 mL), at 0° C., was added sodium hydride (60% dispersion in mineral oil; 13 mg, 0.33 mmol) and the resulting mixture was stirred for 30 min. To the resulting mixture was added (7R)-2-(chloromethyl)-3'-methyl-6,8-dihydro-2'H,5'H-spiro[cyclopenta[g]quinoline-7,4'-imidazolidine]-2',5'-dione (86 mg, 0.27 mmol, described in Intermediate 14) and stirring was continued at ambient temperature for 18 h. The reaction mixture was quenched with a few drops of TFA and concentrated in vacuo to give the title compound in sufficient purity for use in the next step. MS: m/z=531 (M+1).

Step B. Methyl (7-amino-3-{[(7R)-3'-methyl-2',5'-dioxo-6,8-dihydrospiro[cyclopenta[g]quinoline-7,4'-imidazolidin]-2-yl]methyl}-2-oxo-2,3-dihydro-1H-benzimidazol-1-yl)acetate A mixture of methyl (3-{[(7R)-3'-methyl-2',5'-dioxo-6,8-dihydrospiro[cyclopenta[g]quinoline-7,4'-imidazolidin]-2-yl]methyl}-7-nitro-2-oxo-2,3-dihydro-1H-benzimidazol-1-yl)acetate from Step A (143 mg, 0.27 mmol) and 10% Pd/C (20 mg) was stirred vigorously in MeOH (3 mL) and EtOAc (5 mL) under an atmosphere of hydrogen (ca. 1 atm). Additional amounts of 10% Pd/C (20 mg) were added after 16 h and 24 h. After a total reaction time of 96 h, the mixture was filtered through a pad of Celite, washing with MeOH, and the filtrate was concentrated in vacuo to give the title compound in sufficient purity for use in the next step. MS: m/z 501 (M+1).

Step C. (7R)-2-[(2,5-Dioxo-5,6-dihydro-4H-imidazo[1,5,4-de]quinoxalin-1(2H)-yl)methyl]-3'-methyl-6,8-dihydro-2'H,5'H-spiro[cyclopenta[g]quinoline-7,4'-imidazolidine]-2',5'-dione A mixture of methyl (7-amino-3-{[(7R)-3'-methyl-2',5'-dioxo-6,8-dihydrospiro[cyclopenta[g]quinoline-7,4'-imidazolidin]-2-yl]methyl}-2-oxo-2,3-dihydro-1H-benzimidazol-1-yl)acetate from Step B (135 mg, 0.27 mmol) and AcOH (1 mL) was heated in xylenes (5 mL) at reflux for 3 h, then concentrated to dryness under reduced pressure. The crude product was partially purified by silica gel chromatography, eluting with a gradient of $CH_2Cl_2$:MeOH—100:0 to 90:10, to give a crude sample of the title compound. Further purification was achieved by HPLC using a reversed phase C18 column and eluting with a gradient of $H_2O$:$CH_3CN$:$CF_3CO_2H$—90:10:0.1 to 5:95:0.1. The pure, product-containing fractions were combined and concentrated to give the title compound. MS: m/z=469 (M+1). HRMS: m/z=469.1624; calculated m/z=469.1619 for $C_{25}H_{21}N_6O_4$.

Example 3

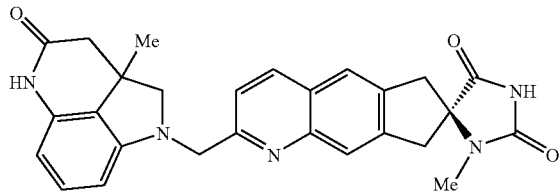

(7R)-3'-Methyl-2-[(2a-methyl-4-oxo-2a,3,4,5-tetrahydropyrrolo[4,3,2-de]quinolin-1(2H)-yl)methyl]-6,8-dihydro-2'H,5'H-spiro[cyclopenta[g]quinoline-7,4'-imidazolidine]-2',5'-dione diastereomer A To a stirred solution of (7R)-3'-methyl-2',5'-dioxo-6,8-dihydrospiro[cyclopenta[g]quinoline-7,4'-imidazolidine]-2-carbaldehyde (612 mg, 2.07 mmol, described in Intermediate 13), 2a-methyl-1,2,2a,5-tetrahydropyrrolo[4,3,2-de]quinolin-4(3H)-one, enantiomer A, (300 mg, 1.59 mmol, described in Intermediate 19), and AcOH (0.46 mL, 7.97 mmol) in DCE (5 mL) was added sodium triacetoxyborohydride (507 mg, 2.39 mmol) and the mixture was stirred for 90 min at ambient temperature. The reaction mixture was partitioned between saturated aqueous $NaHCO_3$ (30 mL) and $CH_2Cl_2$ (30 mL). The organic layer was removed and the aqueous layer was extracted further with $CH_2Cl_2$ (3×30 mL). The combined organic extracts were dried over $Na_2SO_4$, filtered, and concentrated in vacuo. The crude product was purified by silica gel chromatography, eluting with a gradient of $CH_2Cl_2$:MeOH—100:0 to 95:5, to give the title compound. MS: m/z=468 (M+1). HRMS: m/z=468.2032; calculated m/z=468.2030 for $C_{27}H_{26}N_5O_3$.

Example 4

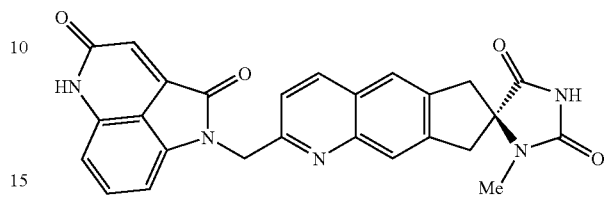

(7R)-2-[(2,4-Dioxo-4,5-dihydropyrrolo[4,3,2-de]quinolin-1(2H)-yl)methyl]-3'-methyl-6,8-dihydro-2'H,5'H-spiro[cyclopenta[g]quinoline-7,4'-imidazolidine]-2',5'-dione Essentially following the procedures described for Example 1, but using pyrrolo[4,3,2-de]quinoline-2,4(1H,5B)-dione (described in Intermediate 17) in place of 2a-methyl-2a,5-dihydropyrrolo[4,3,2-de]quinoline-2,4(1H,3H)-dione, enantiomer B, the title compound and its isomer were prepared. The crude product was purified by HPLC using a reversed phase C18 column and eluting with a gradient of $H_2O$:$CH_3CN$:$CF_3CO_2H$—90:10:0.1 to 5:95:0.1 to give a mixture of the two isomeric products. Further purification was achieved by silica gel chromatography, eluting with a gradient of $CH_2Cl_2$:acetone—100:0 to 50:50, to give (7R)-2-[(2,4-dioxo-2,4-dihydropyrrolo[4,3,2-de]quinolin-5(1H)-yl(methyl]-3'-methyl-6,8-dihydro-2'H,5'H-spiro[cyclopenta[g]quinoline-7,4'-imidazolidine]-2',5'-dione, which eluted first, and (7R)-2-[(2,4-dioxo-4,5-dihydropyrrolo[4,3,2-de]quinolin-1(2H)-yl)methyl]-3'-methyl-6,8-dihydro-2'H,5'H-spiro[cyclopenta[g]quinoline-7,4'-imidazolidine]-2',5'-dione, the title compound, which eluted second. MS: m/z=466 (M+1). HRMS: m/z=466.1508; calculated m/z 466.1510 for $C_{26}H_{20}N_5O_4$.

Example 5

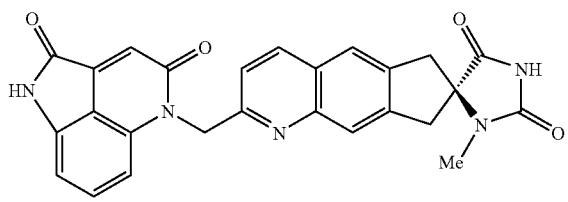

117

(7R)-2-[(2,4-Dioxo-2,4-dihydropyrrolo[4,3,2-de]
quinolin-5(1H)-yl)methyl]-3'-methyl-6,8-dihydro-
2'H,5'H-spiro[cyclopenta[g]quinoline-7,4'-imidazolidine]-2',5'-dione The title compound was isolated from the same reaction mixture as the product in Example 4. MS: m/z=466 (M+1). HRMS: m/z=466.1512; calculated m/z=466.1510 for $C_{26}H_{20}N_5O_4$.

Example 6

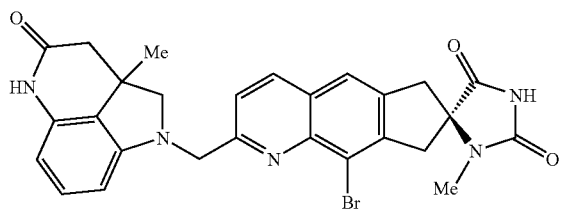

(7R)-3'-Methyl-2-[(2a-methyl-4-oxo-2a,3,4,5-tetrahydropyrrolo[4,3,2-de]quinolin-1(2H)-yl)methyl]-9-bromo-6,8-dihydro-2'H,5'H-spiro[cyclopenta[g]quinoline-7,4'-imidazolidine]-2',5'-dione, diastereomer A Essentially following the procedures described for Example 3, but using (7R)-9-bromo-3'-methyl-2',5'-dioxo-6,8-dihydrospiro[cyclopenta[g]quinoline-7,4'-imidazolidine]-2-carbaldehyde (described in Intermediate 21) in place of (7R)-3'-methyl-2',5'-dioxo-6,8-dihydrospiro[cyclopenta[g]quinoline-7,4'-imidazolidine]-2-carbaldehyde, the title compound was prepared. MS: m/z=546 (M+1). HRMS: m/z=546.1176; calculated m/z=546.1136 for $C_{27}H_{25}{}^{79}BrN_5O_3$.

Examples 7-8

Essentially following the procedures outlined for Example 1 the compounds listed in Table 1 were prepared. The requisite amines were commercially available, described in the literature, synthesized according to methodology described herein (vide supra), or readily synthesized by one skilled in the art of organic synthesis. In some cases, straightforward protecting group strategies were applied.

118

TABLE 1

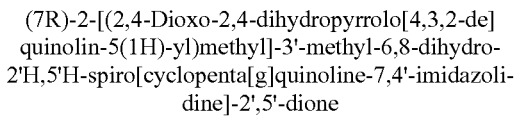

| Example | $R^b$ | MS (M + 1) |
|---|---|---|
| 7 | | 483 |
| 8 | | 551 |

Examples 9-32

Essentially following the procedures outlined for Example 3 the compounds listed in Table 2 were prepared. The requisite amines were commercially available, described in the literature, synthesized according to methodology described herein (vide supra), or readily synthesized by one skilled in the art of organic synthesis. In some cases, straightforward protecting group strategies were applied. The product of the reductive alkylation was manipulated further using known methodology to afford some of the compounds in Table 2.

TABLE 2

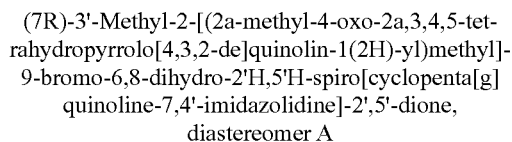

| Example | $R^b$ | MS (M +1) |
|---|---|---|
| 9 | | 454 |

TABLE 2-continued

| Example | R$^b$ | MS (M+1) |
|---|---|---|
| 10 | (ethyl ester acetic acid substituted pyrrolo-quinolinone) | 540 |
| 11 | (carboxylic acid substituted pyrrolo-quinolinone) | 512 |
| 12 | (N,N-dimethyl acetamide substituted pyrrolo-quinolinone) | 539 |
| 13 | (pyrrolidinyl ketone substituted pyrrolo-quinolinone) | 565 |
| 14 | (difluoroethyl substituted pyrrolo-quinolinone) | 518 |
| 15 | (dimethyl substituted pyrrolo-quinolinone) | 482 |
| 16 | (methyl, chloro substituted pyrrolo-quinolinone) | 502 |
| 17 | (ethyl substituted pyrrolo-quinolinone) | 482 |
| 18 | (cyclopropylmethyl substituted pyrrolo-quinolinone) | 508 |
| 19 | (fluoroethyl substituted pyrrolo-quinolinone) | 500 |
| 20 | (methoxyethyl substituted pyrrolo-quinolinone) | 512 |

TABLE 2-continued

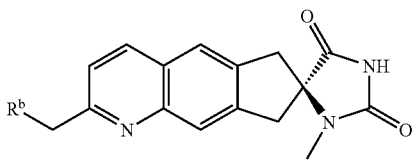

| Example | $R^b$ | MS (M +1) |
|---|---|---|
| 21 | (oxazol-2-ylmethyl-substituted pyrrolo-quinolinone) | 535 |
| 22 | (Me, CF3-substituted pyrrolo-quinolinone) | 536 |
| 23 | (Me, CN-substituted pyrrolo-quinolinone) | 493 |
| 24 | (Me, Br-substituted pyrrolo-quinolinone) | 546 |
| 25 | (Me, Me-substituted pyrrolo-quinolinone) | 482 |
| 26 | (NH-C(O)-Ot-Bu methyl-substituted pyrrolo-quinolinone) | 583 |

TABLE 2-continued

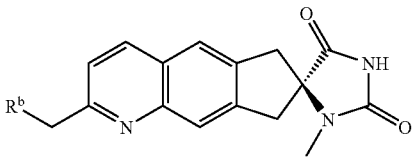

| Example | $R^b$ | MS (M +1) |
|---|---|---|
| 27 | (H2N-methyl-substituted pyrrolo-quinolinone) | 483 |
| 28 | (NH-C(O)-CF3 methyl-substituted pyrrolo-quinolinone) | 579 |
| 29 | (NH-C(O)-NMe2 methyl-substituted pyrrolo-quinolinone) | 554 |
| 30 | (NH-C(O)-cyclopropyl methyl-substituted pyrrolo-quinolinone) | 551 |
| 31 | (NH-C(O)-t-Bu methyl-substituted pyrrolo-quinolinone) | 567 |

TABLE 2-continued

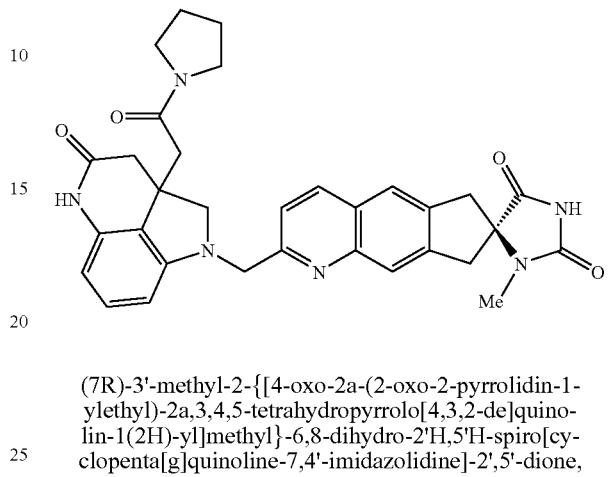

| Example | $R^b$ | MS (M +1) |
|---|---|---|
| 32 | 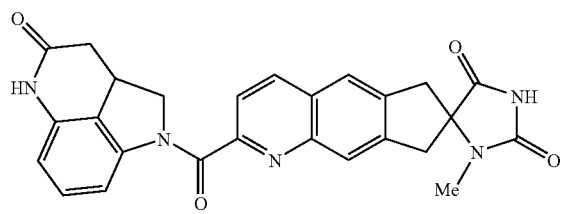 | 583 |

Example 33

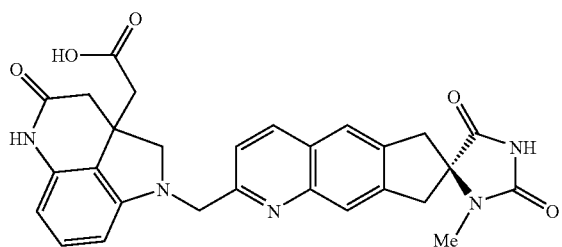

[1-{[(7R-3'-Methyl-2',5'-dioxo-6,8-dihydrospiro[cyclopenta[g]quinoline-7,4'-imidazolidin]-2-yl]methyl}-4-oxo-1,2,4,5-tetrahydropyrrolo[4,3,2-de]quinolin-2a(3H)-yl]acetic acid, diastereomer A To a stirred solution of ethyl[1-{[(7R)-3'-methyl-2',5'-dioxo-6,8-dihydrospiro[cyclopenta[g]quinoline-7,4'-imidazolidin]-2-yl]methyl}-4-oxo-1,2,4,5-tetrahydropyrrolo[4,3,2-de]quinolin-2a(3H)-yl]acetate, diastereomer A (200 mg, 0.371 mmol, described in Example 10) in THF (7 mL) and H₂O (7 mL) was added 1 N LiOH (0.93 mL, 0.93 mmol) and the mixture was stirred at ambient temperature for 18 h. The mixture was adjusted to ca. pH 3 by addition of 10% aqueous citric acid and extracted with EtOAc (50 mL). The organic layer was dried over Na₂SO₄, filtered, and concentrated to dryness in vacuo to give the title compound. MS: m/z=512 (M+1). HRMS: m/z=512.1899; calculated m/z=512.1929 for $C_{28}H_{26}N_5O_5$.

Example 34

(7R)-3'-methyl-2-{[4-oxo-2a-(2-oxo-2-pyrrolidin-1-ylethyl)-2a,3,4,5-tetrahydropyrrolo[4,3,2-de]quinolin-1(2H)-yl]methyl}-6,8-dihydro-2'H,5'H-spiro[cyclopenta[g]quinoline-7,4'-imidazolidine]-2',5'-dione, diastereomer A A mixture of [1-{[(7R)-3'-methyl-2',5'-dioxo-6,8-dihydrospiro[cyclopenta[g]quinoline-7,4'-imidazolidin]-2-yl]methyl}-4-oxo-1,2,4,5-tetrahydropyrrolo[4,3,2-de]quinolin-2a(3H)-yl]acetic acid, diastereomer A (50 mg, 0.098 mmol, described in Example 33), pyrrolidine (20 mg, 0.282 mmol), EDC (28 mg, 0.147 mmol), HOBT (22 mg, 0.147 mmol), and N,N-diisopropylethylamine (0.051 mL, 0.293 mmol) was stirred in DMF (0.5 mL) at ambient temperature for 18 h. The reaction mixture was partitioned between saturated aqueous NaHCO₃ (20 mL) and CH₂Cl₂ (10 mL). The organic layer was removed and the aqueous layer was extracted further with CH₂Cl₂ (2×10 mL). The combined organic extracts were washed with brine (10 mL), dried over Na₂SO₄, filtered, and concentrated in vacuo. The crude product was purified by silica gel chromatography, eluting with a gradient of CH₂Cl₂: MeOH—100:0 to 90:10, to give the title compound. MS: m/z=565 (M+1). HRMS: m/z=565.2578; calculated m/z=565.2558 for $C_{32}H_{33}N_6O_4$.

Example 35

(±)-3'-Methyl-2-[(4-oxo-2a,3,4,5-tetrahydropyrrolo[4,3,2-de]quinolin-1 (2H)-yl)carbonyl]-6,8-dihydro-2'H,5'H-spiro[cyclopenta[g]quinoline-7,4'-imidazolidine]-2',5'-dione, diastereomer B A mixture of (±)-3'-methyl-2',5'-dioxo-6,8-dihydrospiro[cyclopenta[g]quinoline-7,4'-imidazolidine]-2-carboxylic acid (14 mg, 0.045 mmol, described in Intermediate 25), 1,2,2a,5-tetrahydropyrrolo[4,3,2-de]quinolin-4(3H)-one, enantiomer B (8 mg, 0.045 mmol, described in Intermediate 18), EDC (13 mg, 0.068 mmol), HOBT (9 mg, 0.068 mmol), and NAN-diisopropylethylamine (0.039 mL, 0.226 mmol) is stirred in DMF (0.7 mL) at ambient temperature for 18 h. The reaction mixture is purified directly by HPLC using a reversed phase C18 column and eluting with a gradient of $H_2O:CH_3CN:CF_3CO_2H$—90:10:0.1 to 5:95:0.1. The pure, product-containing fractions are combined and concentrated to give the title compound.

Example 36

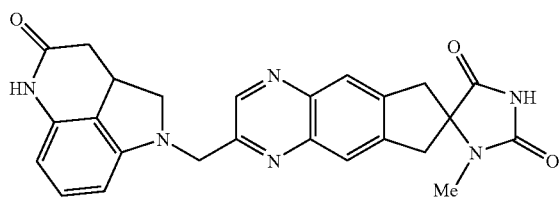

3'-Methyl-2-[(4-oxo-2a,3,4,5-tetrahydropyrrolo[4,3,2-de]quinolin-1(2H)-yl)methyl]-6,8-dihydro-2'H5'H-spiro[cyclopenta[g]quinoxaline-7,4'-imidazolidine]-2',5'-dione, diastereomers A & B Step A. (±)-2-(Hydroxymethyl)-3'-methyl-6,8-dihydro-2'H5'H-spiro[cyclopenta[g]quinoxaline-7,4'-imidazolidine]-2',5'-dione To a stirred solution of 5',6'-diamino-3-methyl-spiro[imidazolidine-4,2'-indane]-2,5-dione (295 mg, 1.20 mmol, described in Intermediate 22) and $MgSO_4$ (1.06 g, 8.81 mmol) in $CH_2Cl_2$ (15 mL) and $CH_3OH$ (15 mL) is added the ethanolate of hydroxypyruvic aldehyde trimer [Evans et al., *J. Am. Chem. Soc.* 1938, 60, 1628-1629] (320 mg, 1.0 mmol). After 4 h, more of the ethanolate of hydroxypyruvic aldehyde trimer (340 mg, 1.1 mmol) is added and the mixture is heated to reflux for 2 h. The reaction mixture is partitioned between brine (50 mL) and EtOAc (150 mL). The organic layer is removed and the aqueous layer is extracted further with EtOAc (2×100 mL). The combined organic extracts are dried over $Na_2SO_4$, filtered, and concentrated in vacuo. The crude product is purified by silica gel chromatography, eluting with a gradient of $CH_2Cl_2$:MeOH—100:0 to 90:10, to give the title compound.

Step B. (±)-3'-Methyl-2',5-dioxo-6,8-dihydrospiro[cyclopenta[g]quinoxaline-7,4'-imidazolidine]-2-carbaldehyde A mixture of (±)-2-(hydroxymethyl)-3'-methyl-6,8-dihydro-2'H,5'H-spiro[cyclopenta[g]quinoxaline-7,4'-imidazolidine]-2',5'-dione from Step A (33 mg, 0.11 mmol) and manganese (IV) oxide (158 mg, 1.82 mmol) in $CHCl_3$ (5 mL) and MeOH (0.1 mL) is heated at reflux for 18 h. The cooled mixture is filtered through a pad of Celite, washing with $CH_2Cl_2$ and MeOH, and the filtrate is concentrated in vacuo to give the title compound.

Step C. 3'-Methyl-2-[(4-oxo-2a,3,4,5-tetrahydropyrrolo[4,3,2-de]quinolin-1(2B)-yl)methyl]-6,8-dihydro-2'H,5'H-spiro[cyclopenta[g]quinoxaline-7,4'-imidazolidine]-2',5'-dione, diastereomers A & B To a stirred solution of (±)-3'-methyl-2',5'-dioxo-6,8-dihydrospiro[cyclopenta[g]quinoxaline-7,4'-imidazolidine]-2-carbaldehyde from Step B (15 mg, 0.051 mmol), 1,2,2a,5-tetrahydropyrrolo[4,3,2-de]quinolin-4(3H)-one, enantiomer B (11 mg, 0.061 mmol, described in Intermediate 18), and AcOH (0.029 mL, 0.51 mmol) in DCE (0.4 mL) is added sodium triacetoxyborohydride (16 mg, 0.076 mmol) and the mixture is stirred for 4 h at ambient temperature. The solvent is removed in vacuo and the residue is purified by HPLC using a reversed phase C18 column and eluting with a gradient of $H_2O:CH_3CN:CF_3CO_2H$—90:10:0.1 to 5:95:0.1. Saturated aqueous $NaHCO_3$ (1 mL) is added to the tubes in the fraction collector in order to rapidly neutralize to eluted solvent. The pure, product-containing fractions are combined and extracted with $CH_2Cl_2$, and the organic extract is dried ($Na_2SO_4$), filtered, and concentrated in vacuo to give the title compound.

Example 37

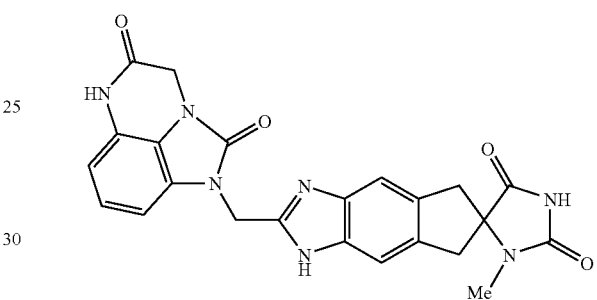

2'-[(2,5-Dioxo-5,6-dihydro-4H-imidazo[1,5,4-de]quinoxalin-1(2H)-yl)methyl]-3-methyl-5',7'-dihydro-1'H,2'H,5'H-spiro[imidazolidine-4,6'-indeno[5,6-d]imidazole]-2,5-dione A mixture of 5',6'-diamino-3-methyl-spiro[imidazolidine-4,2'-indane]-2,5-dione (27 mg, 0.11 mmol, described in Intermediate 22), sodium (2,5-dioxo-5,6-dihydro-4H-imidazo[1,5,4-de]quinoxalin-1(2H)-yl)acetate (27 mg, 0.10 mmol, described in Intermediate 31), BOP (50 mg, 0.11 mmol), and N,N-diisopropylethylamine (0.019 mL, 0.1 mmol) is stirred in DMF (0.4 mL) at ambient temperature for 2 h, then AcOH (0.4 mL) is added and the resulting mixture is heated to 60° C. for 18 h. The mixture is allowed to cool and the precipitate is isolated by filtration. This solid is washed with $H_2O$, then MeOH, then $CH_2Cl_2$, then dried in vacuo to give the title compound.

Example 38

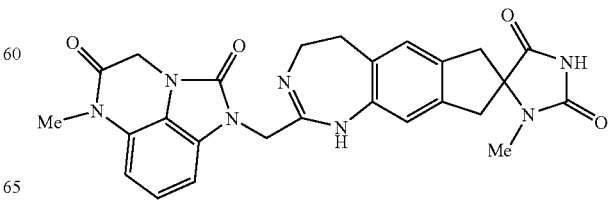

(±)-3-Methyl-2'-[(6-methyl-2,5-dioxo-5,6-dihydro-4H-imidazo[1,5,4-de]quinoxalin-1(2H)-yl)methyl]-4',5',7',9'-tetrahydro-1'H,2'H,5'H-spiro[imidazolidine-4,8'-indeno[5,6-d][1,3]diazepine]-2,5-dione Step A. (6-Methyl-2,5-dioxo-5,6-dihydro-4H-imidazo[1,5,4-de]quinoxalin-1(2H)-yl)acetonitrile To a stirred solution of 6-methyl-4H-imidazo[1,5,4-de]quinoxaline-2,5(1H,6H)-dione (296 mg, 1.46 mmol, described in Intermediate 28) in DMF (5 mL) at 0° C. was added sodium hydride (60% dispersion in mineral oil; 78 mg, 1.96 mmol) and the resulting mixture was stirred for 5 min. Bromoacetonitrile (0.122 mL, 1.75 mmol) in was added dropwise and the reaction mixture was allowed to warm to ambient temperature and was stirred for 3 h, then quenched with $H_2O$ (20 mL). The mixture was extracted with EtOAc (2×30 mL) and the combined organic extracts were washed with brine (10 mL), then dried over $Na_2SO_4$, filtered, and concentrated in vacuo. The crude product was partially purified by silica gel chromatography, eluting with a gradient of $CH_2Cl_2$:MeOH—100:0 to 95:5, followed by trituration with $CH_2Cl_2$ to give the title compound. MS: m/z=243 (M+1).

Step B. 1-Ethoxy-2-(6-methyl-2,5-dioxo-5,6-dihydro-4H-imidazo[1,5,4-de]quinoxalin-1(2H)-yl)ethaniminium chloride A suspension of (6-methyl-2,5-dioxo-5,6-dihydro-4H-imidazo[1,5,4-de]quinoxalin-1(2B)-yl)acetonitrile from Step A (54 mg, 0.223 mmol) in EtOH (5 mL) was cooled to 0° C., then HCl (g) was bubbled in slowly for 1 min. The resulting solution was aged for 30 min, then concentrated to dryness in vacuo to give the title compound in sufficient purity for use in the next step. MS: m/z=290 (M+2).

Step C. (±)-3-Methyl-2'-[(6-methyl-2,5-dioxo-5,6-dihydro-4H-imidazo[1,5,4-de]quinoxalin-1(2H)-yl)methyl]-4',5',7',9'-tetrahydro-1'H,2'H,5'H-spiro[imidazolidine-4,8'-indeno[5,6-d][1,3]diazepine]-2,5-dione A mixture of 1-ethoxy-2-(6-methyl-2,5-dioxo-5,6-dihydro-4H-imidazo[1,5,4-de]quinoxalin-1(2H)-yl)ethaniminium chloride from Step B (72 mg, 0.22 mmol) and (±)-5'-amino-6'-(2-aminoethyl)-3-methyl-1',3'-dihydro-2H,5H-spiro[imidazolidine-4,2'-indene]-2,5-dione (68 mg, 0.25 mmol, described in Intermediate 27) in EtOH (7 mL) is heated to 100° C. for 5 min then allowed to cool. The reaction is poured into dilute aqueous $NaHCO_3$ (50 mL) and the mixture is extracted with EtOAc (100 mL). The organic layer is washed with brine, dried over $Na_2SO_4$, filtered, and concentrated under reduced pressure. The crude product is purified by silica gel chromatography, eluting with a gradient of $CH_2Cl_2$:MeOH—100:0 to 80:20, to give the title compound.

Examples 39-40

Essentially following the procedures outlined for Example 3 the compounds listed in Table 3 are prepared. The requisite amines are commercially available, described in the literature, synthesized according to methodology described herein (vide supra), or readily synthesized by one skilled in the art of organic synthesis. In some cases, straightforward protecting group strategies are applied.

TABLE 3

| Example | $R^b$ |
|---|---|
| 39 | (pyrrolidinylethyl-substituted structure) |
| 40 | (N-methylpiperazinyl-carbonylmethyl-substituted structure) |

Examples 41-53

Essentially following the procedures outlined for Example 37 the compounds listed in Table 4 are prepared. The requisite acids are commercially available, described in the literature, synthesized according to methodology described herein (vide supra), or readily synthesized by one skilled in the art of organic synthesis. In some cases, straightforward protecting group strategies are applied.

TABLE 4

| Example | $R^c$ |
|---|---|
| 41 | (fused tricyclic imidazo structure) |

TABLE 4-continued

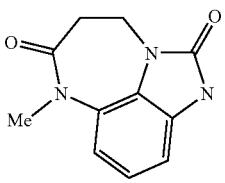

| Example | R<sup>c</sup> |
|---|---|
| 42 | 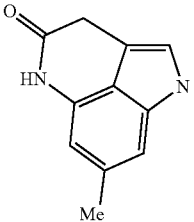 |
| 43 | 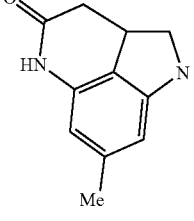 |
| 44 | 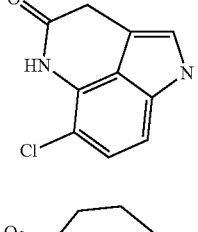 |
| 45 | 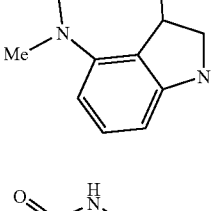 |
| 46 | 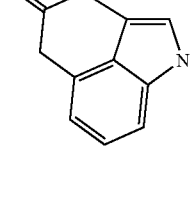 |
| 47 | 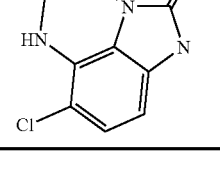 |

TABLE 4-continued

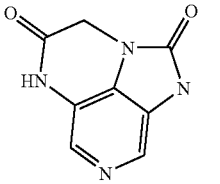

| Example | R<sup>c</sup> |
|---|---|
| 48 | 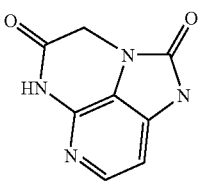 |
| 49 | 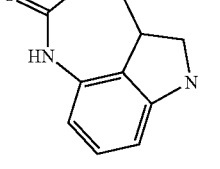 |
| 50 | 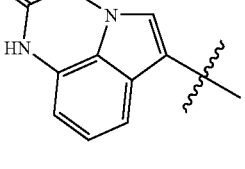 |
| 51 | |
| 52 | |
| 53 | |

Examples 54-57

Essentially following the procedures outlined for Example 3 the compounds listed in Table 5 were prepared. The requisite amines were commercially available, described in the literature, synthesized according to methodology described herein (vide supra), or readily synthesized by one skilled in the art of organic synthesis. In some cases, straightforward protecting group strategies were applied. The product of the reductive alkylation was manipulated further using known methodology to afford some of the compounds in Table 5.

TABLE 5

| Example | $R^b$ | MS (M + 1) |
|---|---|---|
| 54 | —C(=O)NH—Oi-Pr | 569 |
| 55 | —C(=O)NH—OEt | 555 |
| 56 | —C(=O)NH—NHt-Bu | 582 |
| 57 | MeO— | 498 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

I wherein
$A^1$, $A^2$ and $A^3$ are each independently selected from:
 (1) a bond,
 (2) —$CR^{13}R^{14}$—, wherein $R^{13}$ and $R^{14}$ are each independently selected from:
  (a) hydrogen,
  (b) $C_{1-6}$ alkyl, which is unsubstituted or substituted with 1-5 substituents each independently selected from:
   (i) —$C_{3-6}$cycloalkyl,
   (ii) —O—$C_{1-6}$alkyl,
   (iii) halo,
   (iv) hydroxy, or
   (v) phenyl,
  (c) hydroxy, or
  (d) halo,
 (3) —$NR^{10}$—,
 (4) —$CR^{13}R^{14}$—$NR^{10}$—,
 (5) —$CR^{13}R^{14}$—$CH_2$—,
 (6) —$CH_2$—$CR^{13}R^{14}$—,
 (7) —O—$CR^{13}R^{14}$—,
 (8) —$CR^{13}R^{14}$—O—,
 (9) —C≡C—,
 (10) —$C(R^{13})$=$C(R^{14})$—, or
 (11) —C(=O)—,
0-1 of $A^4$, $A^5$, $A^6$ and $A^7$ is:
 —C(=O)—,
where the remainder of $A^4$, $A^5$, $A^6$ and $A^7$ are each independently selected from:
 B (1) a bond, or
 (2) —$CR^{13}R^{14}$—,
$B^1$ are each independently selected from:
 (1)

=C—, (2)

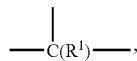

or (3)

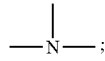

B⁴ is

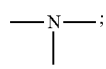

B² and B³ are each independently selected from:
(1) a bond
(2) =C(R¹)—,
(3) —CR¹R²—,
(4) —C(=O)—,
(5) —C(=S)—, or
(6) —C(=NR¹)—;
D¹ and D² are each independently selected from:
(1) =C(R¹)—,
(2) —CR¹R²—,
(3) —C(=O)—,
(4) —C(=S)—,
(5) =N—,
(6) —N(R¹)—, or
(7) —C(=NR¹)—;
E¹ and E⁵ are each independently selected from:
(1) =C(R⁴)—,
(2) —CR⁴R⁵—,
(3) —C(=O)—,
(4) —C(=S)—,
(5) =N—,
(6) =N⁺(O⁻)—; or
(7) —N(R⁴)—,
E³ and E⁴ are each independently selected from:
(1) a bond,
(2) =C(R⁴)—,
(3) —CR⁴R⁵—,
(4) —C(=O)—,
(5) =N—,
(6) =N⁺(O⁻)—,
(7) —N(R⁴)—; or
E² is selected from:
(1)

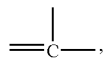

(2)

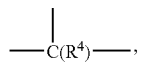

or (3)

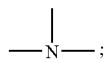

G¹ and G² are independently defined as:
(1) =C(R⁴)—;
T, U and V are each independently selected from:
=C(R¹)—;
W, X, Y, and Z are each independently selected from:
(1) a bond
(2) =C(R¹)—,
(3) —CR¹R²—,
(4) —C(=O)—,
(5) —C(=S)—; or
R¹ and R² are each independently selected from:
(1) hydrogen;
(2) —$C_{1-6}$alkyl, which is unsubstituted or substituted with 1-7 substituents each independently selected from:
(a) halo,
(b) hydroxy,
(c) —O—$C_{1-6}$alkyl, which is unsubstituted or substituted with 1-5 halo,
(d) —$C_{3-6}$cycloalkyl,
(e) phenyl or heterocycle, wherein heterocycle is selected from: azetidinyl, azepanyl, imidazolyl, oxazolyl, pyridinyl, pyrimidinyl, pyrazinyl, pyridazinyl, piperidinyl, azepinyl, piperazinyl, pyrazolyl, pyrrolidinyl, thiazolyl, thienyl, triazolyl, tetrazolyl, tetrahydrofuryl, or morpholinyl,
which phenyl or heterocycle is unsubstituted or substituted with 1-5 substituents each independently selected from:
(i) —$C_{1-6}$alkyl, which is unsubstituted or substituted with 1-5 halo,
(ii) —O—$C_{1-6}$alkyl, which is unsubstituted or substituted with 1-5 halo,
(iii) halo,
(iv) hydroxy,
(v) oxo,
(vi) amino,
(vii) phenyl, or
(viii) benzyl
(f) —$CO_2R^9$, wherein $R^9$ is independently selected from:
(i) hydrogen,
(ii) —$C_{1-6}$alkyl, which is unsubstituted or substituted with 1-6 substituents, substituents each independently selected from:
(I) halo,
(II) hydroxy,
(III) —O—$C_{1-6}$alkyl, which is unsubstituted or substituted with 1-5 halo,
(IV) —$C_{3-6}$cycloalkyl,
(V) phenyl, which is unsubstituted or substituted with 1-5 substituents each independently selected from:
(1) —$C_{1-4}$alkyl,
(2) —O—$C_{1-6}$alkyl,
(3) halo,
(4) trifluoromethyl, or
(5) —$OCF_3$,
(iii) —$C_{3-6}$cycloalkyl, which is unsubstituted or substituted with 1-5 halo, and
(iv) phenyl or heterocycle, wherein heterocycle is selected from: pyridinyl, pyrimidinyl, pyrazinyl, pyridazinyl, thienyl, pyrrolidinyl, thiazolyl, oxazolyl, imidazolyl, triazolyl, tetrazolyl, benzimidazolyl, benzothiazolyl, benzoxazolyl, imidazolinyl, indolinyl, indolyl, quinolinyl, isoquinolinyl, tetrahydroquinolinyl, isoindolinyl, tetrahydroisoquinolinyl, tetrahydrofuryl, quinoxalinyl, piperidinyl, piperazinyl, or morpholinyl, which phenyl or heterocycle is unsubstituted or substituted with 1-5 substituents each independently selected from:
  (I) halo,
  (II) —$C_{1-6}$alkyl, which is unsubstituted or substituted with 1-5 halo
  (III) —O—$C_{1-6}$alkyl, which is unsubstituted or substituted with 1-5 halo
  (IV) —$C_{3-6}$cycloalkyl,
  (V) oxo,
  (VI) —CN,
  (VII) hydroxy, or
  (VIII) phenyl,
(g) —$NR^{10}R^{11}$, wherein $R^{10}$ and $R^{11}$ are each independently selected from:
  (i) hydrogen,
  (ii) —$C_{1-6}$alkyl, which is unsubstituted or substituted with 1-6 substituents each independently selected from:
    (I) —O—$C_{1-6}$alkyl,
    (II) halo,
    (III) hydroxy,
    (IV) —$OCF_3$,
    (V) —$C_{3-6}$cycloalkyl, or
    (VI) phenyl,
  (iii) —$C_{4-6}$cycloalkyl,
  (iv) phenyl, which is unsubstituted or substituted with 1-5 substituents where the substituents are independently selected from:
    (I) —$C_{1-6}$alkyl,
    (II) —O—$C_{1-6}$alkyl,
    (III) halo,
    (IV) hydroxy,
    (V) trifluoromethyl,
    (VI) —$OCF_3$, or
    (VII) CN, or
  (v) benzyl, which is unsubstituted or substituted with 1-5 substituents where the substituents are independently selected from:
    (I) —$C_{1-6}$alkyl,
    (II) —O—$C_{1-6}$alkyl,
    (III) halo, or
    (IV) trifluoromethyl,
  (vi) —$COR^9$, or
  (vii) —$SO_2R^{12}$,
(h) —$SO_2R^{12}$, wherein $R^{12}$ is selected from:
  (i) —$C_{1-6}$alkyl, which is unsubstituted or substituted with 1-6 fluoro,
  (ii) —$C_{3-6}$cycloalkyl,
  (iii) phenyl or heterocycle, wherein heterocycle is selected from: pyridinyl, pyrimidinyl, pyrazinyl, pyridazinyl, piperidinyl, piperazinyl, pyrrolidinyl, thienyl, or morpholinyl,
    which phenyl or heterocycle is unsubstituted or substituted with 1-5 substituents independently selected from:
    (I) —$C_{1-6}$alkyl,
    (II) —O—$C_{1-6}$alkyl,
    (III) halo,
    (IV) hydroxy,
    (V) trifluoromethyl,
    (VI) —$OCF_3$, or
    (VII) CN, or
  (iv) benzyl, which is unsubstituted or substituted with 1-5 substituents independently selected from:
    (I) —$C_{1-6}$alkyl,
    (II) —O—$C_{1-6}$alkyl,
    (III) halo, or
    (IV) trifluoromethyl,
(i) —$CONR^{10a}R^{11a}$, wherein $R^{10a}$ and $R^{11a}$ are each independently selected from:
  (i) hydrogen,
  (ii) —$C_{1-6}$alkyl, which is unsubstituted or substituted with 1-6 substituents each independently selected from:
    (I) —O—$C_{1-6}$alkyl, which is unsubstituted or substituted with 1-5 halo,
    (II) halo,
    (III) hydroxy,
    (IV) —$OCF_3$,
    (V) —$C_{3-6}$cycloalkyl, or
    (VI) phenyl,
  (iii) —$C_{5-6}$cycloalkyl,
  (iv) phenyl, which is unsubstituted or substituted with 1-5 substituents where the substituents are independently selected from:
    (I) —$C_{1-6}$alkyl, which is unsubstituted or substituted with 1-5 halo,
    (II) —O—$C_{1-6}$alkyl, which is unsubstituted or substituted with 1-5 halo,
    (III) halo,
    (IV) hydroxy,
    (V) trifluoromethyl,
    (VI) —$OCF_3$, or
    (VII) CN, or
  (v) benzyl, which is unsubstituted or substituted with 1-5 substituents where the substituents are independently selected from:
    (I) —$C_{1-6}$alkyl, which is unsubstituted or substituted with 1-5 halo,
    (II) —O—$C_{1-6}$alkyl, which is unsubstituted or substituted with 1-5 halo,
    (III) halo, or
    (IV) trifluoromethyl,
  or where $R^{10a}$ and $R^{11a}$ join to form a ring selected from azetidinyl, pyrrolidinyl, piperidinyl, azepanyl, piperazinyl, or morpholinyl, which ring is unsubstituted or substituted with 1-5 substituents each independently selected from:
    (I) —$C_{1-6}$alkyl, which is unsubstituted or substituted with 1-5 halo,
    (II) —O—$C_{1-6}$alkyl, which is unsubstituted or substituted with 1-5 halo,
    (III) halo,
    (IV) hydroxy,
    (V) phenyl,
    (VI) benzyl,
    (VII) —$COR^9$, or
    (VIII) —$SO_2R^{12}$
(j) trifluoromethyl,
(k) —$OCO_2R^9$,
(l) —$(NR^{10a})CO_2R^9$,
(m) —$O(CO)NR^{10a}R^{11a}$,
(n) —$(NR^9)(CO)NR^{10a}R^{11a}$,
(o) —O—$C_{3-6}$cycloalkyl,
(p) —$SO_2NR^{10a}R^{11a}$, or
(q) —CN,
(3) —$C_{3-6}$cycloalkyl, which is unsubstituted or substituted with 1-7 substituents each independently selected from:

(a) halo,
(b) hydroxy,
(c) —O—$C_{1-6}$alkyl, which is unsubstituted or substituted with 1-5 halo,
(d) —$C_{1-6}$alkyl, which is unsubstituted or substituted with 1-5 halo,
(e) phenyl, which is unsubstituted or substituted with 1-5 substituents each independently selected from:
  (i) —$C_{1-6}$alkyl,
  (ii) —O—$C_{1-6}$alkyl,
  (iii) halo,
  (iv) hydroxy, or
  (v) trifluoromethyl,
(4) phenyl or heterocycle, wherein heterocycle is selected from: pyridinyl, pyrimidinyl, pyrazinyl, thienyl, pyridazinyl, pyrrolidinyl, azetidinyl, azepanyl, thiazolyl, isothiazolyl, oxazolyl, isoxazolyl, imidazolyl, triazolyl, tetrazolyl, azepinyl, benzimidazolyl, benzopyranyl, benzofuryl, benzothiazolyl, benzoxazolyl, chromanyl, furyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, pyrazolidinyl, pyrazolyl, pyrrolyl, quinazolinyl, tetrahydrofuryl, thiazolinyl, purinyl, naphthyridinyl, quinoxalinyl, 1,3-dioxolanyl, oxadiazolyl, piperidinyl, tetrahydropyranyl, tetrahydrothienyl, tetrahydrothiopyranyl, or morpholinyl, which phenyl or heterocycle is unsubstituted or substituted with 1-5 substituents each independently selected from:
  (a) —$C_{1-6}$alkyl, which is unsubstituted or substituted with 1-5 substituents where the substituents are each independently selected from:
    (i) halo,
    (ii) hydroxy,
    (iii) —O—$C_{1-6}$alkyl, which is unsubstituted or substituted with 1-5 halo,
    (iv) —$C_{3-6}$cycloalkyl,
    (v) phenyl, or
    (vi) —$CO_2R^9$, or
    (vii) —$NR^{10}R^{11}$,
  (b) halo,
  (c) hydroxy,
  (d) —O—$C_{1-6}$alkyl, which is unsubstituted or substituted with 1-6 fluoro,
  (e) —$C_{3-6}$cycloalkyl,
  (f) phenyl or heterocycle, wherein heterocycle is selected from: pyrrolidinyl, piperidinyl, piperazinyl, pyridinyl, pyrimidinyl, pyrazinyl, thienyl, or morpholinyl, which phenyl or heterocycle is unsubstituted or substituted with 1-substituents each independently selected from:
    (i) —$C_{1-6}$alkyl, which is unsubstituted or substituted with 1-5 halo,
    (ii) —O—$C_{1-6}$alkyl, which is unsubstituted or substituted with 1-5 halo,
    (iii) halo,
    (iv) hydroxy, or
    (v) trifluoromethyl,
  (g) —$CO_2R^9$,
  (h) —$(CO)R^9$,
  (i) —$NR^{10}R^{11}$,
  (j) —$CONR^{10a}R^{11a}$,
  (k) oxo
  (l) —$SR^{12}$,
  (m) —$S(O)R^{12}$,
  (n) —$SO_2R^{12}$,
  (o) —CN or
  (p) —$SO_2NR^{10a}R^{11a}$,
(5) halo,
(6) oxo,
(7) hydroxy,
(8) —O—$C_{1-6}$alkyl, which is unsubstituted or substituted with 1-5 substituents where the substituents are each independently selected from:
  (a) halo,
  (b) hydroxy,
  (c) —$C_{3-6}$cycloalkyl,
  (d) phenyl,
  (e) —$CO_2R^9$, or
  (f) —$NR^{10}R^{11}$,
(9) —CN,
(10) —$CO_2R^9$,
(11) —$NR^{10}R^{11}$,
(12) —$SR^{12}$,
(13) —$S(O)R^{12}$,
(14) —$SO_2R^{12}$,
(15) —$SO_2NR^{10a}R^{11a}$,
(16) —$CONR^{10a}R^{11a}$,
(17) —$OCO_2R^9$,
(18) —$(NR^{10a})CO_2R^9$,
(19) —$O(CO)NR^{10a}R^{11a}$,
(20) —$(NR^9)(CO)NR^{10a}R^{11a}$,
(21) —(CO)—$(CO)NR^{10a}R^{11a}$, or
(22) —(CO)—$(CO)OR^9$;
$R^4$ and $R^5$ are each independently selected from:
(1) hydrogen;
(2) —$C_{1-4}$alkyl, which is unsubstituted or substituted with 1-5 substituents each independently selected from:
  (a) halo,
  (b) hydroxy,
  (c) —O—$C_{1-6}$alkyl, which is unsubstituted or substituted with 1-5 halo,
  (d) —$C_{3-6}$cycloalkyl,
  (e) phenyl,
  (f) —$CO_2R^9$,
  (g) —$NR^{10}R^{11}$, or
  (h) —$CONR^{10a}R^{11a}$
(3) —$C_{3-6}$cycloalkyl,
(4) phenyl, which is unsubstituted or substituted with 1-3 substituents where the substituents are each independently selected from:
  (a) —$C_{1-4}$alkyl, which is unsubstituted or substituted with 1-3 halo,
  (b) halo,
  (c) hydroxy, or
  (d) —O—$C_{1-4}$alkyl, which is unsubstituted or substituted with 1-6 halo,
(5) halo,
(6) hydroxy,
(7) —O—$C_{1-6}$alkyl, which is unsubstituted or substituted with 1-5 halo,
(8) —CN,
(9) —$CO_2R^9$,
(10) —$NR^{10}R^{11}$,
(11) —$SO_2R^{12}$,
(12) —$CONR^{10a}R^{11a}$,
(13) —$OCO_2R^9$, or
(14) —$(NR^{10a})CO_2R^9$;
$R^6$ is selected from:
(1) hydrogen,
(2) —$C_{1-6}$alkyl or —$C_{3-6}$cycloalkyl which are unsubstituted or substituted with 1-7 substituents each independently selected from:

(a) halo,
(b) hydroxy,
(c) —O—$C_{1-6}$alkyl,
(d) —$C_{3-6}$cycloalkyl,
(e) phenyl, which is unsubstituted or substituted with 1-5 substituents each independently selected from:
 (i) —$C_{1-6}$alkyl,
 (ii) —O—$C_{1-6}$alkyl,
 (iii) halo,
 (iv) hydroxy, or
 (v) trifluoromethyl,
(f) —$CO_2R^9$,
(g) —$NR^{10}R^{11}$,
(h) —$CONR^{10}R^{11}$,
(i) —$SO_2R^{12}$, or
(j) trifluoromethyl
(3) phenyl or heterocycle, wherein heterocycle is selected from: pyridinyl, pyrimidinyl, pyrazinyl, thienyl, or morpholinyl, which phenyl or heterocycle is unsubstituted or substituted with 1-5 substituents each independently selected from:
 (a) —$C_{1-6}$alkyl,
 (b) —O—$C_{1-6}$alkyl,
 (c) halo,
 (d) hydroxy, or
 (e) trifluoromethyl;

or a pharmaceutically acceptable salt thereof or an individual enantiomer or diastereomer thereof.

2. The compound of claim 1 having the formula Ia:

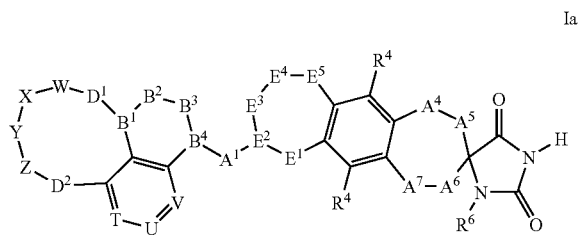

Ia or a pharmaceutically acceptable salt thereof or an individual enantiomer or diastereomer thereof.

3. The compound of claim 1 having the formula Ib:

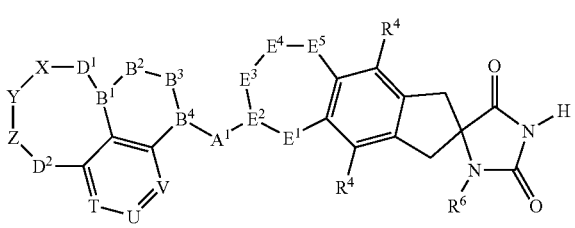

Ib or a pharmaceutically acceptable salt thereof or an individual enantiomer or diastereomer thereof.

4. The compound of claim 1 having the formula Ic:

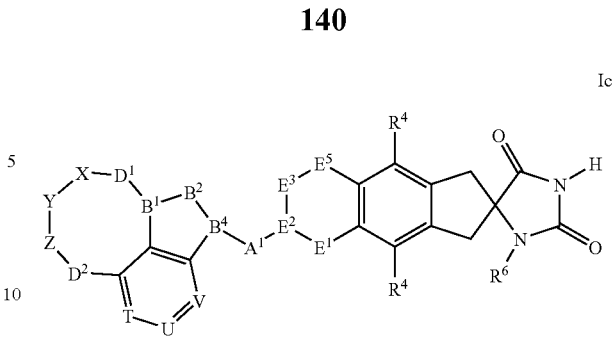

Ic or a pharmaceutically acceptable salt thereof or an individual enantiomer or diastereomer thereof.

5. The compound of claim 1 having the formula Id:

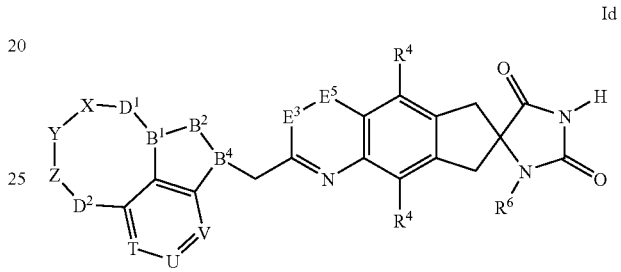

Id or a pharmaceutically acceptable salt thereof or an individual enantiomer or diastereomer thereof.

6. The compound of claim 1 having the formula Ie:

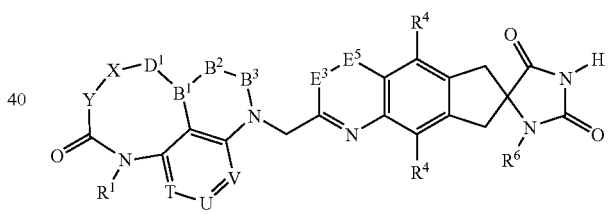

Ie or a pharmaceutically acceptable salt thereof or an individual enantiomer or diastereomer thereof.

7. The compound of claim 1 wherein $A^1$ is selected from $CH_2$ or —C(=O); $A^2$ is a bond; and $A^3$ is a bond.

8. The compound of claim 1 wherein $A^4$ is selected from $CH_2$ or a bond; $A^5$ is $CH_2$; $A^6$ is $CH_2$; and $A^7$ is selected from $CH_2$ and a bond.

9. The compound of claim 1 wherein $B^1$ is selected from

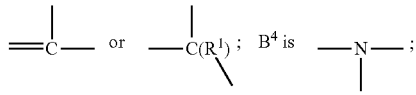

$B^2$ is selected from $C(R^1)$—, —$CR^1R^2$—, or C(=O); and $B^3$ is selected from =C(H)—, —$CH_2$—, —C(=O)—, or a bond.

10. The compound of claim 1 wherein $D^1$ is selected from =$C(R^1)$—, $CR^1R^2$—, or —$N(R^1)$—; and $D^2$ is selected from —$CR^1R^2$— or —$N(R^1)$—.

11. The compound of claim 1 wherein $E^1$ is selected from: =C($R^4$)—, —$CR^4R^5$—, =N— or —N($R^4$)—; $E^2$ is selected from

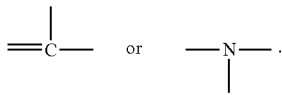

$E^3$ is selected from:
a bond, =C($R^4$)—, —$CR^4R^5$—, =N— or —N($R^4$)—; $E^4$ is selected from a bond or —$CH_2$—; and $E^5$ is selected from =C($R^4$)—, —$CR^4R^5$—, =N— and —N($R^4$)—.

12. The compound of claim 1 wherein T is =C($R^1$)—; U is =C($R^1$)— and V is =C(H)—.

13. The compound of claim 1 wherein W is selected from a bond, —$CR^1R^2$— or —C(=O)—; X is selected from a bond, —$CR^1R^2$—, or —C(=O)—; Y is selected from a B bond, —$CR^1R^2$—, or —C(=O)—; and Z is selected from a bond, —$CR^1R^2$—, or —C(=O)—.

14. The compound of claim 1 wherein $R^1$ and $R^2$ are independently selected from:
(1) hydrogen;
(2) —$C_{1-6}$alkyl, which is unsubstituted or substituted with 1-5 substituents each independently selected from:
  (a) halo,
  (b) hydroxy,
  (c) —O—$C_{1-6}$alkyl, which is unsubstituted or substituted with 1-3 fluoro,
  (d) —$C_{3-6}$cycloalkyl,
  (e) phenyl or heterocycle, wherein heterocycle is selected from: azetidinyl, imidazolyl, oxazolyl, pyridinyl, pyrimidinyl, pyrazinyl, piperidinyl, piperazinyl, pyrrolidinyl, thiazolyl, thienyl, triazolyl, tetrazolyl, tetrahydrofuryl, or morpholinyl, which phenyl or heterocycle is unsubstituted or substituted with 1-3 substituents each independently selected from:
    (i) —$C_{1-4}$alkyl, which is unsubstituted or substituted with 1-3 fluoro,
    (ii) —O—$C_{1-4}$alkyl, which is unsubstituted or substituted with 1-3 fluoro,
    (iii) halo,
    (iv) hydroxy,
    (v) trifluoromethyl, or
    (vi) —$OCF_3$,
  (f) —$CO_2R^9$,
  (g) —$NR^{10}R^{11}$,
  (h) —$CONR^{10a}R^{11a}$, or
  (i) —(NR Oa)$CO_2R^9$, or
  (j) —($NR^9$)(CO)$NR^{10a}R^{11a}$;
(3) —$C_{3-6}$cycloalkyl, which is unsubstituted or substituted with 1-3 substituents each independently selected from:
  (a) halo,
  (b) hydroxy,
  (c) —$C_{1-6}$alkyl, or
  (d) —O—$C_{1-6}$alkyl,
(4) phenyl or heterocycle, wherein heterocycle is selected from: pyridinyl, pyrimidinyl, pyrazinyl, thienyl, pyrrolidinyl, azetidinyl, thiazolyl, oxazolyl, isoxazolyl, imidazolyl, triazolyl, tetrazolyl, benzimidazolyl, benzoxazolyl, imidazolinyl, indolinyl, indolyl, quinolinyl, isoquinolinyl, tetrahydroquinolinyl, isoindolinyl, tetrahydroisoquinolinyl, 2-oxopiperazinyl, 2-oxopiperidinyl, 2-oxopyrrolidinyl, quinazolinyl, tetrahydrofuryl, naphthyridinyl, quinoxalinyl, 1,3-dioxolanyl, oxadiaz-olyl, piperidinyl, tetrahydropyranyl, and morpholinyl, which phenyl or heterocycle is unsubstituted or substituted with 1-3 substituents each independently selected from:
  (a) —$C_{1-4}$alkyl, which is unsubstituted or substituted with 1-3 fluoro,
  (b) halo,
  (c) hydroxy,
  (d) —O—$C_{1-4}$alkyl, which is unsubstituted or substituted with 1-6 fluoro,
  (e) —$C_{3-6}$cycloalkyl,
  (g) —$CO_2R^9$,
  (h) —$NR^{10}R^{11}$, or
  (i) —$CONR^{10a}R^{11a}$,
(5) halo,
(6) hydroxy,
(7) —O—$C_{1-4}$alkyl, which is unsubstituted or substituted with 1-3 halo,
(8) —CN,
(9) —$CO_2R^9$,
(10) —$NR^{10}R^{11}$,
(11) —$CONR^{10a}R^{11a}$, or
(12) —($NR^{10a}$)$CO_2R^9$.

15. The compound of claim 1 wherein $R^1$ and $R^2$ are independently selected from:
(1) hydrogen;
(2) —$C_{1-4}$alkyl, which is unsubstituted or substituted with 1-3 substituents each independently selected from:
  (a) halo,
  (b) —O—$C_{1-4}$alkyl,
  (c) phenyl or heterocycle, wherein heterocycle is selected from: azetidinyl, oxazolyl, pyridinyl, pyrimidinyl, pyrazinyl, piperidinyl, piperazinyl, pyrrolidinyl, tetrahydrofuryl, or morpholinyl,
    which phenyl or heterocycle is unsubstituted or substituted with 1-3 substituents each independently selected from:
    (i) —$C_{1-4}$alkyl,
    (ii) —O—$C_{1-4}$alkyl,
    (iii) halo, or
    (iv) hydroxy,
  (d) —$CO_2R^9$,
  (e) —$NR^{10}R^{11}$,
  (f) —$CONR^{10a}R^{11a}$,
(3) —$C_{3-6}$cycloalkyl,
(4) phenyl or heterocycle, wherein heterocycle is selected from: pyridinyl, pyrimidinyl, pyrazinyl, pyrrolidinyl, azetidinyl, oxazolyl, imidazolyl, 2-oxopiperazinyl, 2-oxopiperidinyl, 2-oxopyrrolidinyl, tetrahydrofuryl, oxadiazolyl, piperidinyl, or morpholinyl, which phenyl or heterocycle is unsubstituted or substituted with 1-3 substituents each independently selected from:
  (a) —$C_{1-4}$alkyl, which is unsubstituted or substituted with 1-3 fluoro,
  (b) halo,
  (c) hydroxy,
  (d) —O—$C_{1-4}$alkyl,
  (e) —$C_{3-6}$cycloalkyl,
  (f) —$NR^{10}R^{11}$, or
  (g) —$CONR^{10}R^{11}$,
(5) halo,
(6) hydroxy,
(7) —O—$C_{1-4}$alkyl, which is unsubstituted or substituted with 1-3 halo,
(8) —CN,
(9) —$CO_2R^9$,
(10) —$NR^{10}R^{11}$,

(11) —CONR$^{10a}$R$^{11a}$, or
(12) —(NR$^{10a}$)CO$_2$R$^9$.
16. A compound selected from:
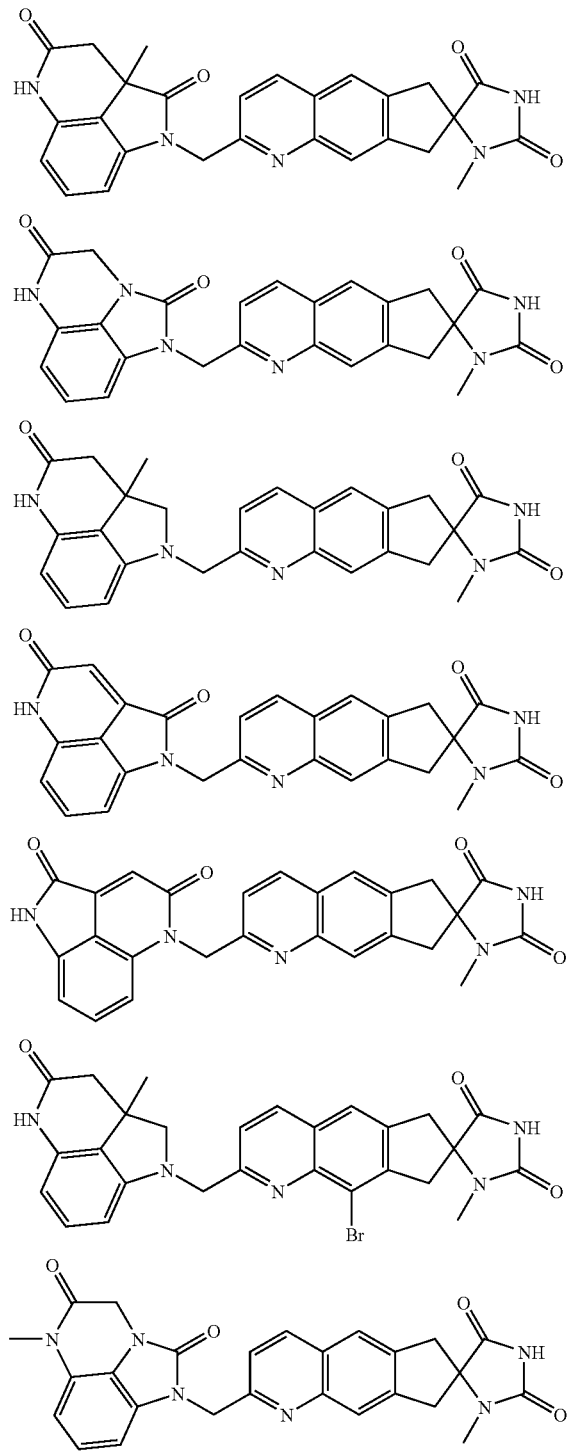
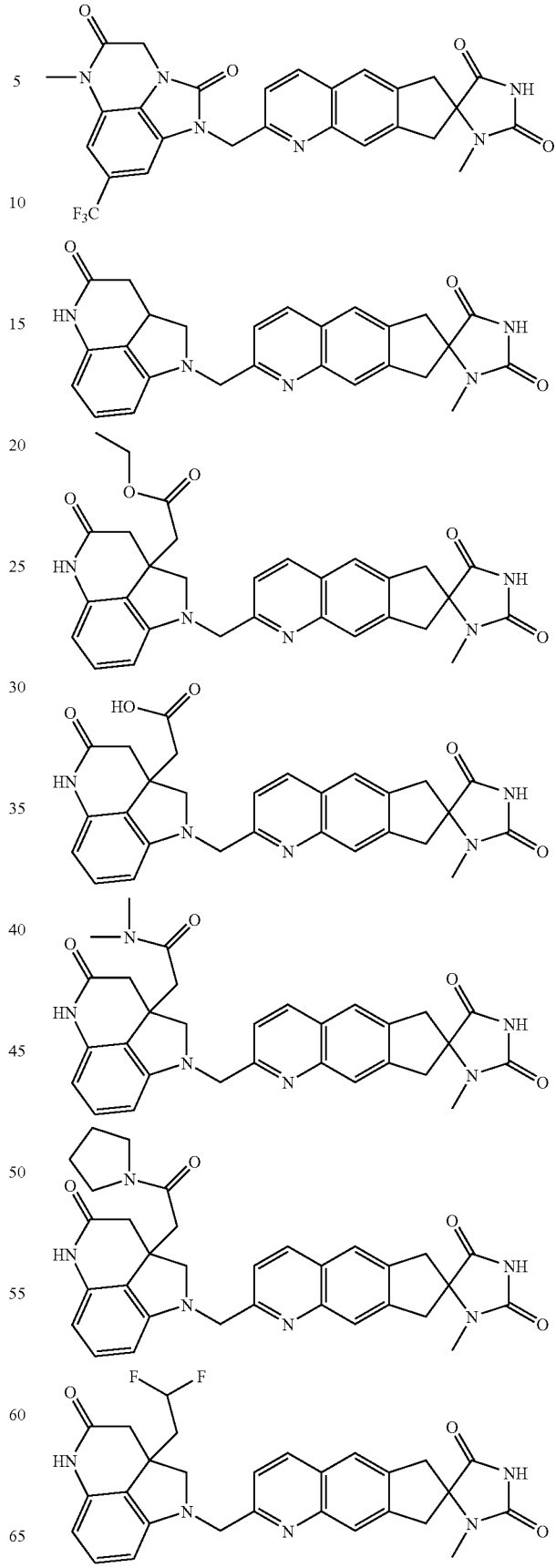

145
-continued
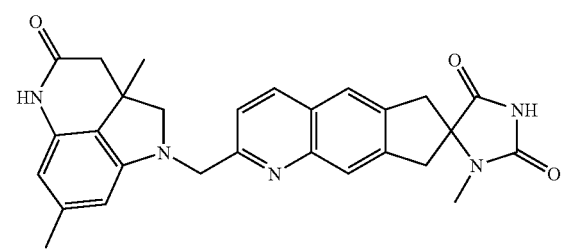
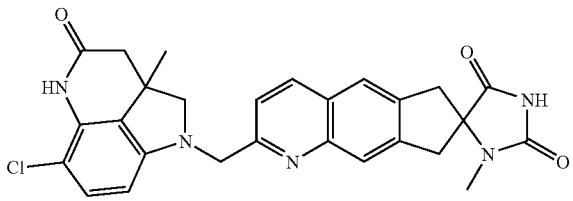
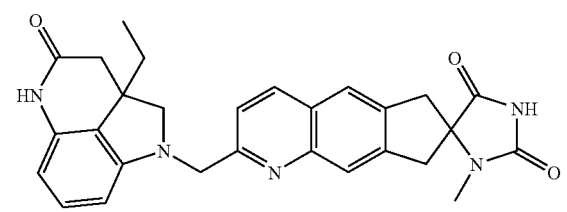
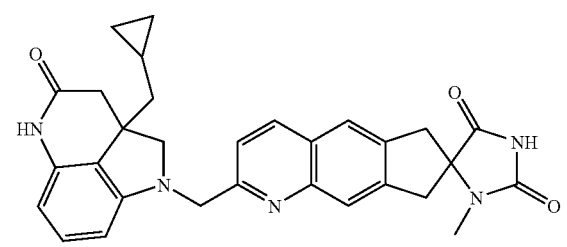
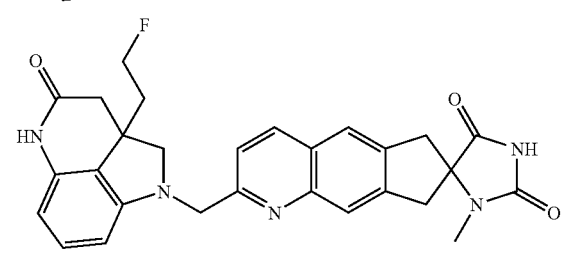
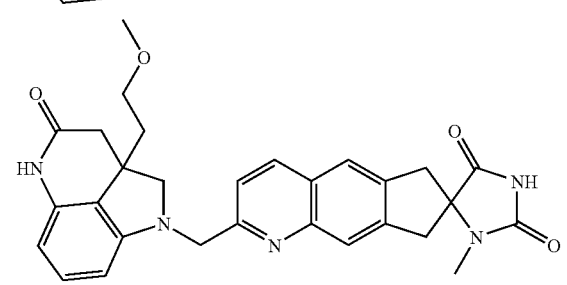
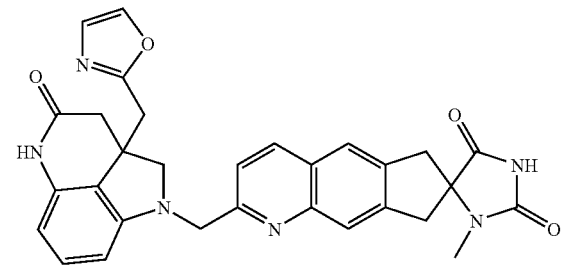
146
-continued
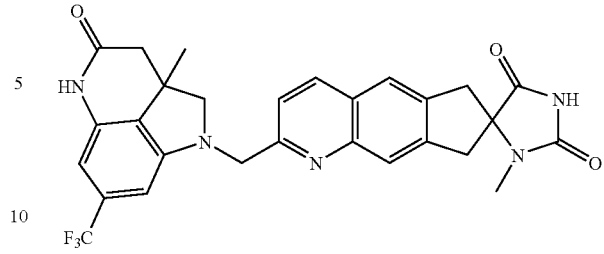
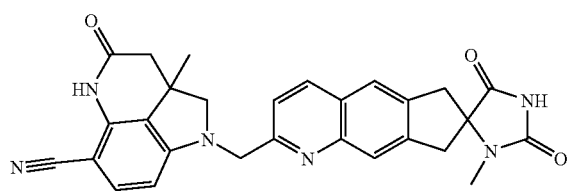
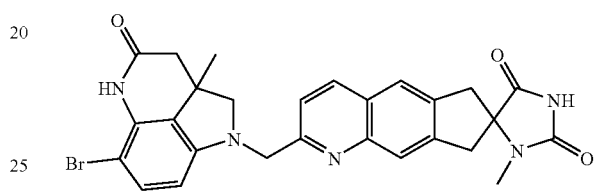
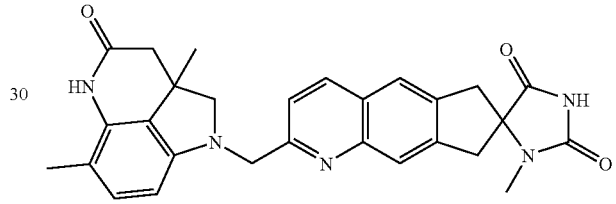
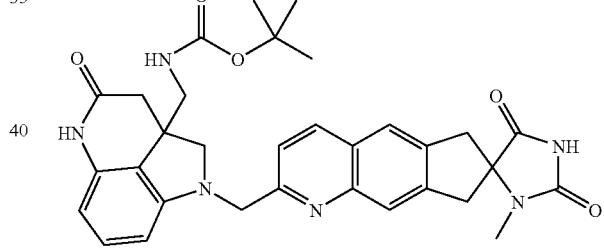
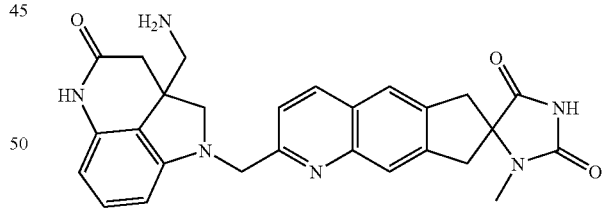
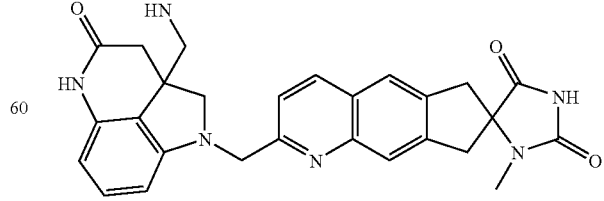

147
-continued
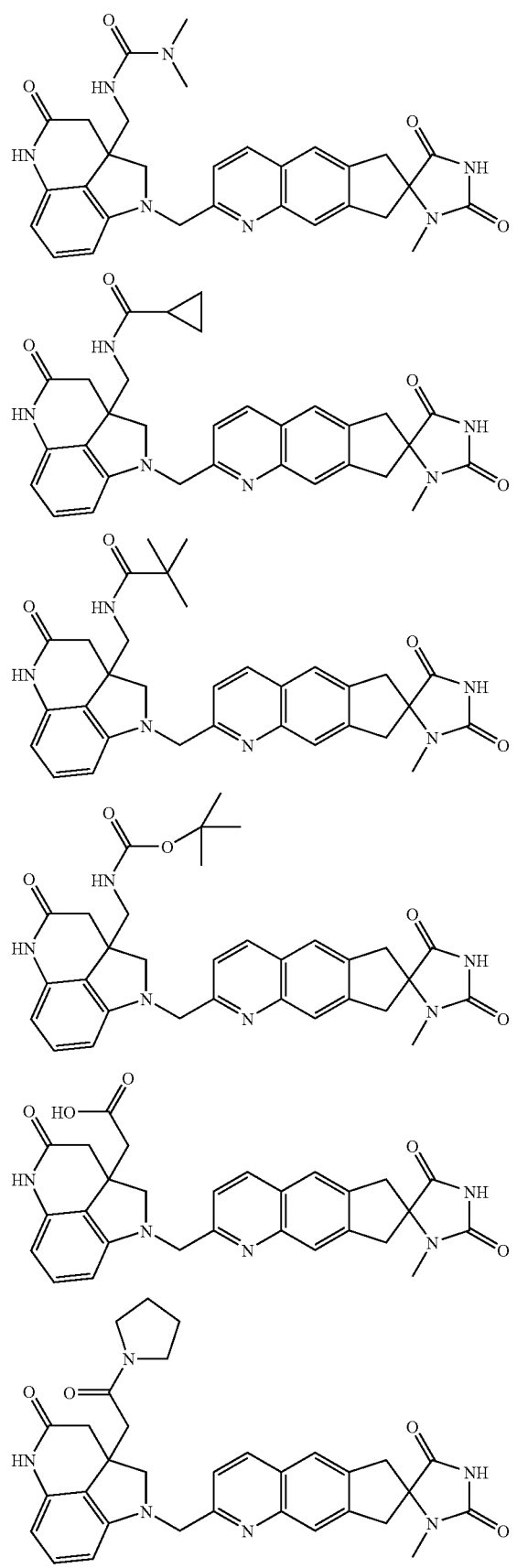
148
-continued
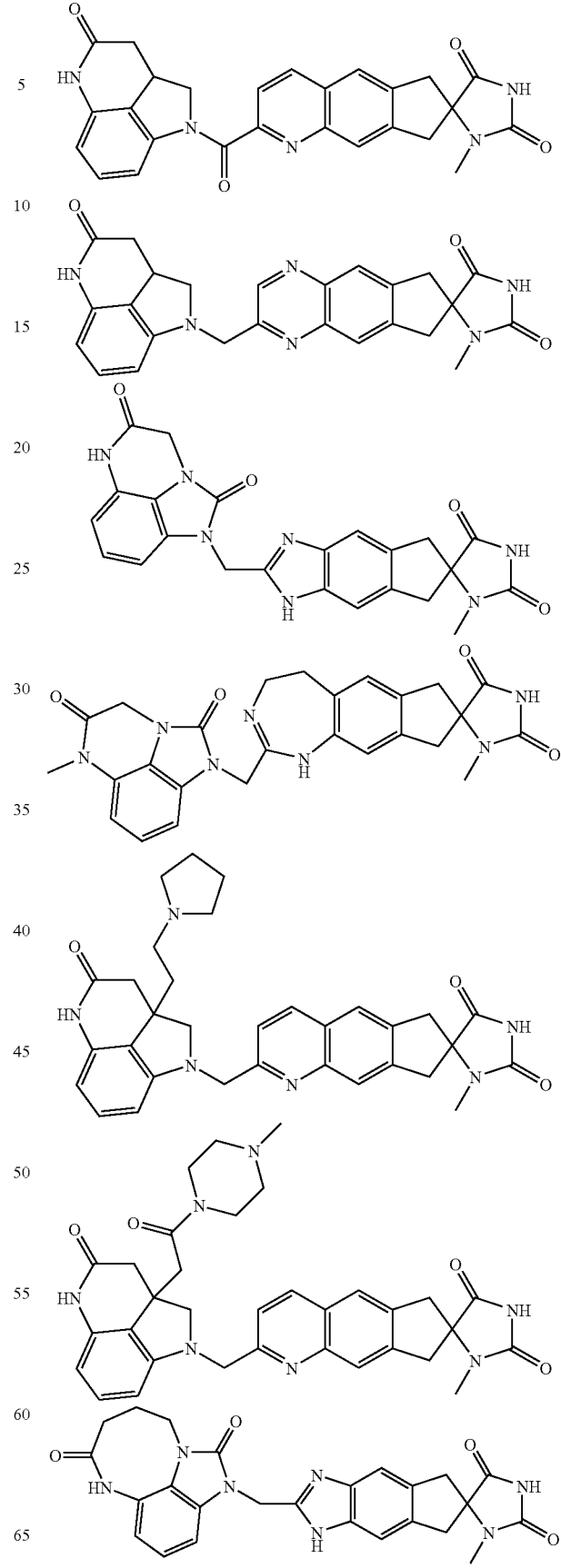

149
-continued
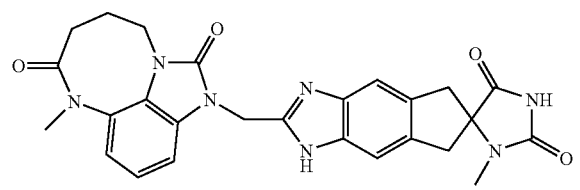
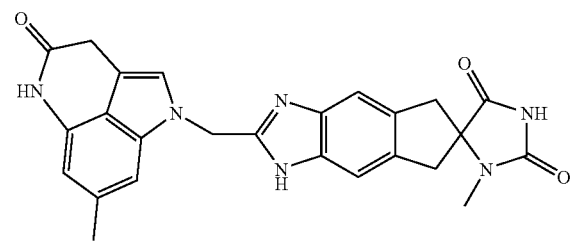
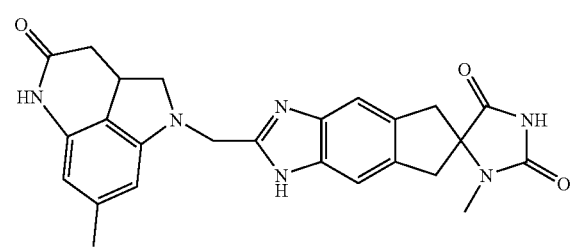
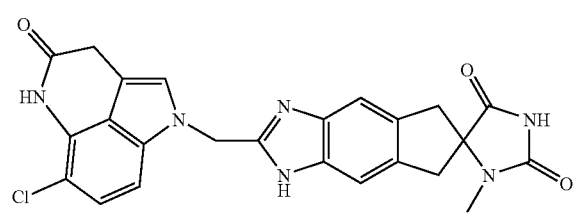
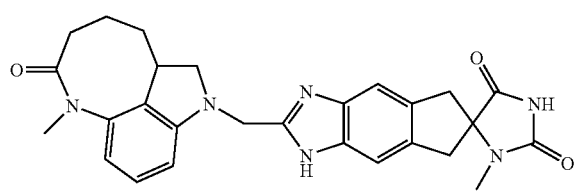
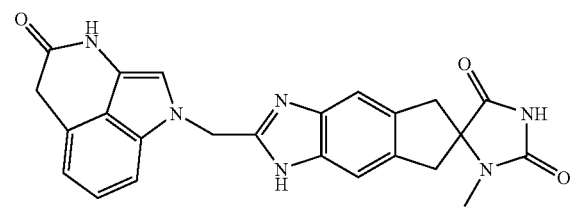
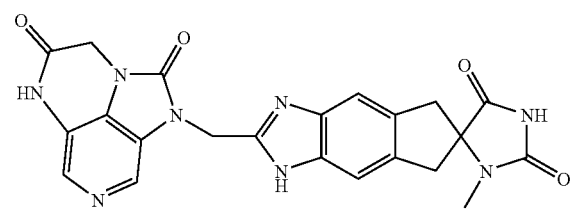
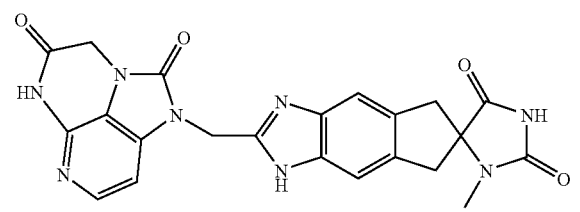
150
-continued
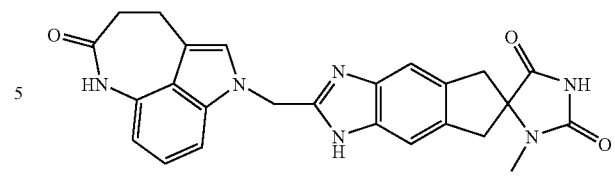
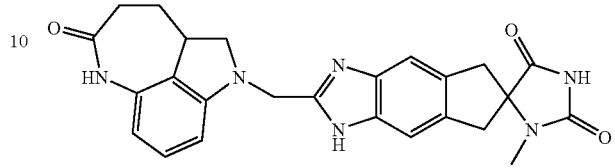
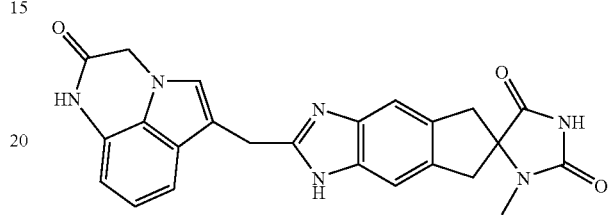
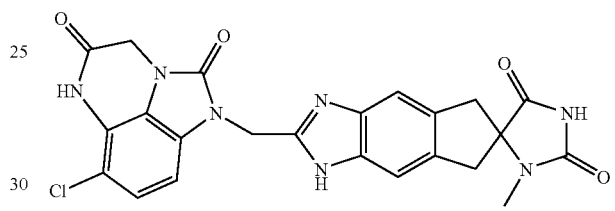
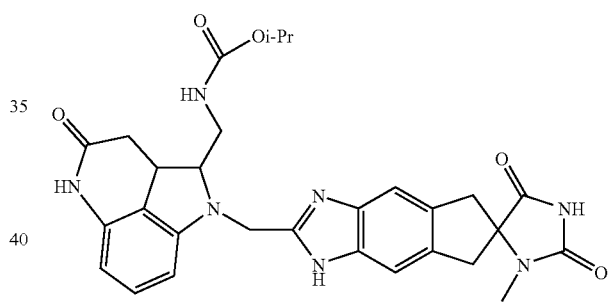
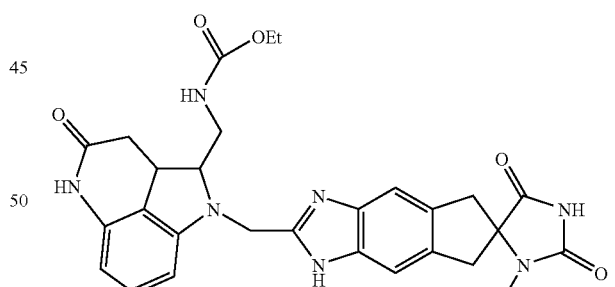
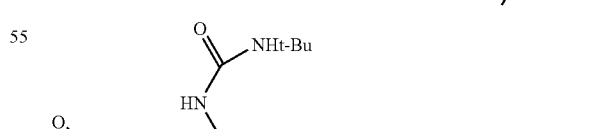
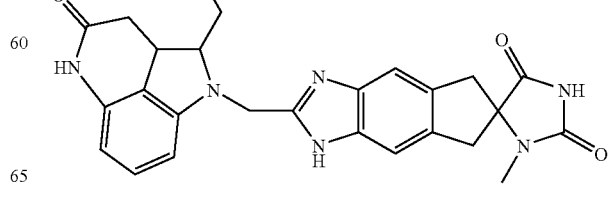

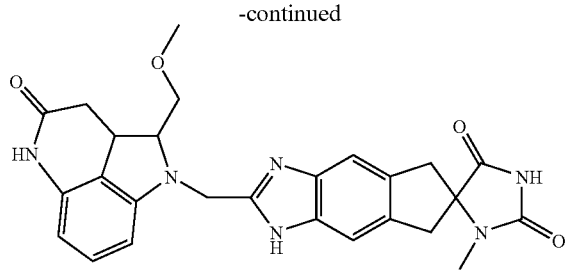

or a pharmaceutically acceptable salt thereof or an individual stereoisomer thereof.

17. A pharmaceutical composition which comprises an inert carrier and the compound of Claim 1, or a pharmaceutically acceptable salt thereof or an individual enantiomer or diastereomer thereof.

18. A method for treating headache in a mammalian patient in need of such which comprises administering to the patient a therapeutically effective amount of the compound of claim 1, or a pharmaceutically acceptable salt thereof or an individual enantiomer or diastereomer thereof.

19. A method of treating headaches, said method comprising the co-administration, to a person in need of such treatment, of:
    a therapeutically effective amount of the compound of claim 1 or a pharmaceutically acceptable salt thereof; and
    a therapeutically effective amount of a second agent selected from serotonin agonists, analgesics, anti-inflamatory agents, anti-hypertensives and anticonvulsants.

\* \* \* \* \*